US009150617B2

(12) United States Patent
McCoy et al.

(10) Patent No.: US 9,150,617 B2
(45) Date of Patent: Oct. 6, 2015

(54) IMMUNOREGULATORY PEPTIDES AND METHODS OF USE

(71) Applicant: 13 Therapeutics, Inc., Portland, OR (US)

(72) Inventors: Sharon L. McCoy, Portland, OR (US); Steven H. Hefeneider, Portland, OR (US)

(73) Assignee: 13THERAPEUTICS, INC., Portland, OR (US)

( * ) Notice: Subject to any disclaimer, the term of this patent is extended or adjusted under 35 U.S.C. 154(b) by 114 days.

(21) Appl. No.: 13/753,141

(22) Filed: Jan. 29, 2013

(65) Prior Publication Data

US 2013/0203679 A1    Aug. 8, 2013

Related U.S. Application Data

(62) Division of application No. 12/794,185, filed on Jun. 4, 2010, now Pat. No. 8,450,285.

(60) Provisional application No. 61/184,438, filed on Jun. 5, 2009, provisional application No. 61/184,455, filed on Jun. 5, 2009, provisional application No. 61/220,738, filed on Jun. 26, 2009, provisional application No. 61/220,745, filed on Jun. 26, 2009, provisional application No. 61/256,364, filed on Oct. 30, 2009.

(51) Int. Cl.
| A61K 38/10 | (2006.01) |
| C07K 7/06 | (2006.01) |
| C07K 7/08 | (2006.01) |
| C07K 14/47 | (2006.01) |
| C07K 14/07 | (2006.01) |
| C07K 14/005 | (2006.01) |
| A61K 38/00 | (2006.01) |

(52) U.S. Cl.
CPC ... *C07K 7/08* (2013.01); *C07K 7/06* (2013.01); *C07K 14/005* (2013.01); *C07K 14/07* (2013.01); *C07K 14/47* (2013.01); *A61K 38/00* (2013.01); *C07K 2319/10* (2013.01); *C12N 2710/24122* (2013.01)

(58) Field of Classification Search
None
See application file for complete search history.

(56) References Cited

U.S. PATENT DOCUMENTS

| 5,804,604 | A | 9/1998 | Frankel et al. |
| 6,093,417 | A | 7/2000 | Petrus |
| 6,306,993 | B1 | 10/2001 | Rothbard et al. |
| 6,589,503 | B1 | 7/2003 | Piwnica-Worms |
| 6,593,292 | B1 | 7/2003 | Rothbard et al. |
| 6,669,951 | B2 | 12/2003 | Rothbard et al. |
| 6,759,387 | B2 | 7/2004 | Rothbard et al. |
| 6,998,383 | B2 | 2/2006 | Aggarwal et al. |
| 7,192,930 | B2 | 3/2007 | Hefeneider et al. |
| 7,229,961 | B2 | 6/2007 | Rothbard et al. |
| 7,557,086 | B2 | 7/2009 | Hefeneider et al. |
| 8,071,553 | B2 | 12/2011 | Hefeneider et al. |
| 8,450,285 | B2 * | 5/2013 | McCoy et al. ............... 514/21.6 |
| 8,580,748 | B2 | 11/2013 | McCoy et al. |
| 2002/0127198 | A1 | 9/2002 | Rothbard et al. |
| 2002/0169279 | A1 | 11/2002 | Montelaro et al. |
| 2003/0022831 | A1 | 1/2003 | Rothbard et al. |
| 2003/0083256 | A1 | 5/2003 | Rothbard et al. |
| 2004/0186045 | A1 | 9/2004 | Rothbard et al. |
| 2005/0244430 | A1 | 11/2005 | O'Neill et al. |
| 2006/0009391 | A1 | 1/2006 | Hefeneider et al. |
| 2006/0078944 | A1 | 4/2006 | Kuai et al. |
| 2006/0211752 | A1 | 9/2006 | Kohn et al. |
| 2007/0129308 | A1 | 6/2007 | Hefeneider et al. |
| 2007/0173436 | A1 | 7/2007 | Rothbard et al. |
| 2007/0265206 | A1 | 11/2007 | Sharma et al. |
| 2008/0039395 | A1 | 2/2008 | Hefeneider et al. |
| 2009/0005339 | A1 | 1/2009 | Scholz et al. |
| 2009/0306225 | A1 | 12/2009 | Lichter et al. |
| 2009/0318364 | A1 | 12/2009 | Hefeneider et al. |
| 2010/0317564 | A1 | 12/2010 | McCoy et al. |
| 2012/0258921 | A1 | 10/2012 | McCoy et al. |
| 2013/0203683 | A1 | 8/2013 | McCoy et al. |
| 2013/0210741 | A1 | 8/2013 | McCoy et al. |
| 2014/0378395 | A1 | 12/2014 | McCoy et al. |

FOREIGN PATENT DOCUMENTS

| CA | 2094658 A1 | 10/1993 |
| CN | 1642982 | 7/2005 |
| CN | 1700930 | 11/2005 |
| EP | 0599303 A2 | 6/1994 |
| EP | 0599303 A3 | 7/1998 |
| WO | WO 79/00515 A1 | 8/1979 |
| WO | WO 92/07871 A1 | 5/1992 |
| WO | WO 97/40854 A2 | 11/1997 |
| WO | WO 97/40854 A3 | 3/1998 |

(Continued)

OTHER PUBLICATIONS

McCoy, J. Immunol., 2005; 174:3006-3014.*
Goffin, 1992, Molecular Endocrinology, 6, 1381-1392.*
Tsung, Shock, vol. 27, No. 4, pp. 364-369, 2007.*
U.S. Appl. No. 14/047,802, filed Oct. 7, 2013, McCoy et al.
Tscharke, et al. Poxvirus CD8+ T-cell determinants and cross-reactivity in BALB/c mice. J Virol. Jul. 2006;80(13):6318-23.
European search report and opinion dated Jun. 12, 2013 for EP Application No. 10784168.6.
U.S. Appl. No. 13/752,969, filed Jan. 29, 2013, McCoy et al.
U.S. Appl. No. 13/753,106, filed Jan. 29, 2013, McCoy et al.
Akira. Mammalian Toll-like receptors. Curr. Opin. Immunol 2003; 15:5-11.
Ailmawi, et al. Negative regulation of nuclear factor-kappaB activation and function by glucocorticoids. J. Mol. Endocrinol. 2002; 28:69-78.
Andreakos, et al. Cytokines and anti-cytokine biologicals in autoimmunity present and future. Cytokine Growth Factor Rev. 2002; 13:299-313.

(Continued)

Primary Examiner — Satyanarayana R Gudibande
(74) Attorney, Agent, or Firm — Wilson Sonsini Goodrich & Rosati

(57) ABSTRACT

Peptides for the treatment of inflammation, and therapeutic uses and methods of using the same are disclosed. Peptides including a transducing sequence are effective for inhibiting cytokine activity and TNF-α secretion through interaction with toll-like receptors. Experiments are described illustrating the efficacy of the compounds in treating otitis media

8 Claims, 4 Drawing Sheets

(56) References Cited

FOREIGN PATENT DOCUMENTS

| WO | WO 98/52614 A2 | 11/1998 |
|---|---|---|
| WO | WO 98/52614 A3 | 3/1999 |
| WO | WO 00/50093 A1 | 8/2000 |
| WO | WO 01/13957 A2 | 3/2001 |
| WO | WO 01/13957 A3 | 10/2001 |
| WO | WO 02/067917 A1 | 9/2002 |
| WO | WO 02/069930 A1 | 9/2002 |
| WO | WO 03/035695 A2 | 5/2003 |
| WO | WO 2004/022762 A1 | 3/2004 |
| WO | WO 2004/093897 A1 | 11/2004 |
| WO | WO 2010/055500 A1 | 5/2010 |
| WO | WO 2010/141845 A2 | 12/2010 |
| WO | WO 2010/141845 A9 | 6/2011 |
| WO | WO 2010/141845 A8 | 12/2011 |

OTHER PUBLICATIONS

Bartfai, et al. A low molecular weight mimic of the Toll/IL-1 receptor/resistance domain inhibits IL-1 receptor-mediated responses. Proc. Natl. Acad. Sci. U.S.A. 2003; 100:7971-7976.

Barton, et al. Linking Toll-like receptors to IFN-.alpha./.beta. expression. Nat. Immunol 2003; 4:432-433.

Barzilai et al.. Middle ear effusion II-6 concentration in bacterial and non-bacterial acute otitis media. Acta Paediatr 2000; 89:1068-1071.

Basu, et al. Toll-like receptors: function and roles in lung disease. Am. J. Physiol. Lung Cell Mol. Physiol. 2004; 286:L887-892.

Bellows, et al. Vaccinia virus-induced inhibition of nitric oxide production. J. Surg. Res. 2003; 111:127-135.

Bone, et al., "Definitions for sepsis and organ failure and guidelines for the use of innovative therapies in sepsis," Chest, 101:1644-1655, (1992).

Bowie, et al. A46R and A52R from vaccinia virus are antagonists of host IL-1 and toll-like receptor signaling. Proc. Natl. Acad. Sci. U.S.A. 2000; 97:10162-10167.

Brint, et al. ST2 is an inhibitor of interleukin 1 receptor and Toll-like receptor 4 signaling and maintains endotoxin tolerance. Nat. Immunol. 2004; 5:373-379.

Chuang, et al. Triad3A, and E3 ubiquitin-protein ligase regulating Toll-like receptors. Nat. Immunol. 2004; 5:495-502.

Daly, et al. Chronic Otitis Media with Effusion. Pediatrics in Review 1999; 20:85-93.

Daun, et al. Interleukin-1/Toll receptor family members: receptor structure and signal transduction pathways. J. Interferon Cytokine Res. 2000; 20:843-855.

Delgado, et al. PACAP in immunity and inflammation. Ann. N. Y. Acad. Sci. 2003; 992:141-157.

Fan, et al. Toll-like receptor-4(TLR4) signaling augments chemokine-induced neutrophil migration by modulating cell surface expression of chemokine receptors. Nat. Med. 2003; 9:315-321.

Granucci, et al. Inducible Il-2 production by dendritic cells revealed by global gene expression analysis. Nat. Immunol. 2001; 2:882-888.

Harte, et al. The poxvirus protein A52R targets Toll-like receptor signaling complexes to suppress host defense. J. Exp. Med. 2003; 197:343-351.

Hayashi, et al. The innate immune response to bacterial flagellin is mediated by Toll-like receptor 5. Nature 2001; 410:1099-1103.

Hemmi, et al. A Toll-like receptor recognizes bacterial DNA. Nature 2000; 408:740-745.

Hoshino, et al. Cutting Edge: Toll-like receptor 4(TLR4)-deficient mice are hyporesponsive to lipopolysaccharide: evidence for TLR4 as the Lps gene product. J. Immunol 1999; 162:3749-3752.

Ikezoe, et al. PC-SPES: A potent inhibitor of nuclear factor-.kappa.B rescues mice from lipopolysaccharide-induced septic shock. Mol. Pharmacol. 2003; 64:1521-1529.

International search report and written opinion dated Oct. 2, 2012 for PCT Application No. US2012/32353.

Janssens, et al. Functional diversity and regulation of different interleukin-1 receptor-associated kinase (IRAK) family members. Mol. Cell 2003; 11:293-302.

Karasen, et al. Effect of web 2170 BS, platelet activating factor receptor inhibitor, in the guinea pig model of middle ear inflammation. Ann Otol Rhinol Laryngol 2000; 109:549-553.

Kopp, et al. Inhibition of NF-kappa B by sodium salicylate and aspirin. Science 1994; 265:956-959.

Krieg. CpG motifs in bacterial DNA and their immune effects. Ann. Rev. Immunol. 2002; 20:709-760.

Kubba, et al. The aetiology of otitis media with effusion: a review. Clin Otolaryngol 2000; 25:181-194.

McCoy, et al. Activation of RAW264.7 macrophages by bacterial DNA and Lipopolysaccharide increases cell surface DNA binding and internalization. J. Biol. Chem. 2004; 279:17217-17223.

McCoy, et al. Identification of a Peptide Derived form Vaccinia Virus A52R Protein That Inhibits Cytokine Secretion in Response to TLR-Dependent Signaling and Reduces In Vivo Bacterial-Induced Inflammation. The Journal of Immunology, 2005, 174:3006-3014.

Meng, et al. Antagonistic antibody prevents Toll-like receptor 2-driven lethal shock-like syndromes. J. Clin. Invest. 2004; 113:1473-1481.

Nemoto, et al. *Escherichia coli* LPS-induced LV dysfunction: role of toll-like receptor-4 in the adult heart. Am J Physiol Heart Circ Physiol 282:H2316-H2323, 2002.

Ng, et al. "Predicting Deleterious Amino Acid Substitutions," Genome Research, 11:863-874, (2001).

O'Brien, et al. "SEPSIS," The American Journal of Medicine, 120:1012-1022, (2007).

Office action dated Jan. 24, 2006 for U.S. Appl. No. 11/178,316.
Office action dated Feb. 26, 2010 for U.S. Appl. No. 11/834,506.
Office action dated Mar. 20, 2008 for U.S. Appl. No. 11/834,506.
Office action dated Jun. 3, 2010 for U.S. Appl. No. 11/834,506.
Office action dated Jun. 29, 2006 for U.S. Appl. No. 11/178,316.
Office action dated Jul. 31, 2009 for U.S. Appl. No. 11/834,506.
Office action dated Aug. 10, 2009 for U.S. Appl. No. 11/834,506.
Office action dated Nov. 26, 2008 for U.S. Appl. No. 11/834,506.
Office action dated Dec. 7, 2012 for U.S. Appl. No. 13/440,591.

O'Neill. The Toll/interleukin-1 receptor domain: a molecular switch for inflammation and host defence. Biochem. Soc. Trans. 2000; 28:557-563.

O'Neill. Therapeutic targeting of Toll-like receptors for inflammatory and infectious diseases. Curr. Opin. Pharm. 2003, 3:396-403.

Ozato, et al. Toll-like receptor signaling and regulation of cytokine gene expression in the immune system BioTechniques 2002; Oct. Suppl:66-75.

Peterson, et al. Polyamino acid enhancement of bacterial phagocytosis by human polymorphonuclear leukocytes and peritoneal macrophages. Infect Immun. Feb. 1984;43(2):561-6.

Rittirsch et al., "The disconnect between animal models of species and human sepsis," The Journal of Leukocyte Biology, 81:137-143, (2007).

Schnare, et al. Toll-like receptor control activation of adaptive immune responses. Nat. Immuno 2001; 2:947-950.

Sela, et al. Different roles of D-amino acids in immune phenomena. FASEB J. May 1997;11(6):449-56.

Sweet, et al. A novel pathway regulating lipopolysaccharide-induced shock by ST2/T1 via inhibition of Toll-like receptor 4 expression. J. Immunol 2001; 166:6633-6639.

Takeda et al. TLR signaling pathways. Semin Immunol. 2004; 16:3-9.

Takeda, et al. Toll-like receptors. Ann. Rev. Immunol. 2003; 21:335-378.

Trinchieri. Interleukin-12: a cytokine at the interface of inflammation and immunity Adv. Immunol 1998; 70:83-243.

Tsung et al., "A novel inhibitory peptide of toll-like receptor signaling limits lipolysaccharide-induced produced of inflammatory mediators and enhances survival in mice," Shock, 27(4):364-369, (2007).

Voet, et al. Abnormal hemoglobins. Biochemistry. 1994; 2:235-241.
Wender, et al. The design, synthesis, and evaluation of molecules that enable or enhance cellular uptake: Peptoid molecular transporters. Proc. Natl. Acad. Sci. 2000; U.S.A. 97:13003-13008.

Yi, et al. Cutting Edge: Rapid induction of mitogen-activated protein kinases by immune stimulatory CpG DNA. J. Immunol. 1999; 161:4493-4497.

(56) References Cited

OTHER PUBLICATIONS

Yi, et al. Role of mitogen-activated protein kinases in CpG DNA-mediated IL-10 and IL-12 production: central role of extracellular signal-regulated kinase in the negative feedback loop of the CpG DNA-mediated Th1 response. J. Immunol 2002; 168:4711-4720.

Zuany-Amorim, et al. Toll-like receptors as potential therapeutic targets for multiple diseases. Nat. Rev. Drug Discov. 2002; 1:797-807.

National Laboratory Animal Center. Central Institute of experimental animal; Japan 1999. Source: http://www.nlac.mahidol.ac.th/nlacmuEN/p_animal_BALB_cMlac.htm.

Notice of allowance dated Mar. 6, 2009 for U.S. Appl. No. 11/656,512.

Notice of allowance dated Jul. 8, 2013 for U.S. Appl. No. 13/440,591.

Notice of allowance dated Jul. 28, 2011 for U.S. Appl. No. 12/479,645.

Notice of allowance dated Sep. 22, 2011 for U.S. Appl. No. 12/479,645.

Notice of allowance dated Oct. 31, 2012 for U.S. Appl. No. 12/794,185.

Notice of allowance dated Dec. 12, 2006 for U.S. Appl. No. 11/178,316.

Office action dated Mar. 26, 2015 for U.S. Appl. No. 14/047,802.

Tuomanen. Pathogenesis of pneumococcal inflammation: otitis media. Vaccine. Dec. 8, 2000;19 Suppl 1:S38-40.

Guide to Grammar: Capital Community College Foundation website. http://grammar.ccc.commnet.edu/grammar/marks/slash.htm. Accessed Feb. 17, 2015.

Office action dated Feb. 5, 2015 for U.S. Appl. No. 13/752,969.

Office action dated Feb. 6, 2015 for U.S. Appl. No. 13/753,106.

Notice of allowance dated May 22, 2015 for U.S. Appl. No. 13/753,106.

Notice of allowance dated Jul. 7, 2015 for U.S. Appl. No. 13/752,969.

Notice of allowance dated Jul. 28, 2015 for U.S. Appl. No. 13/752,969.

\* cited by examiner

Panel A

Panel B

Panel A: Hearing thresholds

Panel B: Number of animals with hearing loss

|  | Day 5 | Day 13 |
|---|---|---|
| PBS | 75% (6/8) | 63% (5/8) |
| P13 | 25% (2/8) | 13% (1/8) |

IMMUNOREGULATORY PEPTIDES AND METHODS OF USE

This application is a divisional of U.S. patent application Ser. No. 12/794,185, filed Jun. 4, 2010, which claims the priority benefit of U.S. Provisional Application No. 61/184,438, filed Jun. 5, 2009, U.S. Provisional Application No. 61/184,455, filed Jun. 5, 2009, U.S. Provisional Application No. 61/220,738, filed Jun. 26, 2009, U.S. Provisional Application No. 61/220,745, filed Jun. 26, 2009, and U.S. Provisional Application No. 61/256,364, filed Oct. 30, 2009, each of which is incorporated herein by reference in its entirety. This application contains a Sequence Listing which has been submitted in ASCII format via EFS-Web and is hereby incorporated by reference in its entirety. The ASCII copy, created on Jan. 23, 2013, is named 37501703402_sequence_listing.txt and is 116 kilobytes in size.

STATEMENT AS TO FEDERALLY SPONSORED RESEARCH

The work leading to the present invention was supported by SBIR AI065000, "Bacterial-Induced Sepsis: A New Treatment Strategy" and SBIR DC005882, "New Treatment for Inflammation in Middle Ear Infections." The U.S. Government may have certain rights in the invention.

BACKGROUND OF THE INVENTION

Toll-like receptors (TLRs) recognize and respond to conserved motifs termed pathogen-associated molecular patterns (PAMPs). TLRs are characterized by an extracellular leucine-rich repeat motif and an intracellular Toll/IL-1 receptor (TIR) domain. Triggering of TLRs by PAMPs initiates a series of intracellular signaling events resulting in an inflammatory immune response designed to contain and eliminate the pathogen. Viruses encode immunoregulatory proteins, such as A52R (produced by the vaccina virus), that can effectively inhibit intracellular TIR signaling resulting in a diminished inflammatory immune response.

Chronic otitis media (COM) affects both children and adults. The chronic inflammation seen in COM can impact the inner ear and can lead to sensorineural hearing loss. COM is a significant medical problem, and no current therapeutics, other than steroids, are available for treating COM. Many patients with COM require surgical placement of ear tubes. As with acute otitis media (AOM), patients with COM experience decreased hearing due to development of an intense inflammatory response within the middle ear, including the presence of residual fluid.

SUMMARY OF THE INVENTION

In some embodiments, the invention contemplates a pharmaceutical composition comprising a peptide comprising:
  a) a sequence of any one of SEQ ID NOS: 187-368; or
  b) a derivative of P13 comprising at least one D-amino acid residue.

In some embodiments, the invention contemplates a pharmaceutical composition comprising a peptide comprising a sequence of any one of SEQ ID NOS: 1-186.

In some embodiments, the invention contemplates a peptide comprising the sequence of any one of SEQ ID NOS: 1-368.

In some embodiments, the invention contemplates a derivative of a peptide comprising the sequence of any one of SEQ ID NOS: 1-369, wherein the derivative comprises at least one D-amino acid residue.

In some embodiments, the invention contemplates a method of regulating cellular activity, the method comprising administering to an organism in need or want thereof an effective amount of a pharmaceutical composition comprising a peptide comprising:
  a) a sequence of any one of SEQ ID NOS: 187-368; or
  b) a derivative of P13 comprising at least one D-amino acid residue, wherein the peptide optionally further comprises a transducing sequence at the C-terminus.

In some embodiments, the invention contemplates a method of treating inflammation in an animal, the method comprising administering to an animal in need or want thereof a pharmaceutical composition comprising a peptide comprising:
  a) a sequence of any one of SEQ ID NOS: 187-368; or
  b) a derivative of P13 comprising at least one D-amino acid residue, wherein the peptide optionally further comprises a transducing sequence at the C-terminus.

In some embodiments, the invention contemplates a method of treating sinusitis, the method comprising administering an aerosol composition to an organism in need or want thereof, the aerosol composition comprising a therapeutically-effective amount of a peptide comprising:
  a) a sequence of any one of SEQ ID NOS: 187-369; or
  b) a derivative of P13 comprising at least one D-amino acid residue, wherein the peptide optionally further comprises a transducing sequence at the C-terminus.

In some embodiments, the invention contemplates a method of improving hearing in an animal, the method comprising administering to an animal having middle and/or inner ear inflammation and reduced hearing a therapeutically-effective amount of a peptide comprising:
  a) a sequence of any one of SEQ ID NOS: 187-369; or
  b) a derivative of P13 comprising at least one D-amino acid residue, wherein the peptide optionally further comprises a transducing sequence at the C-terminus, wherein the peptide is administered topically, wherein the hearing improves to a level no better than ordinary levels, and/or the hearing improves faster than the hearing would improve without administration of the peptide.

In some embodiments, the invention contemplates a method of treating middle and/or inner ear inflammation, the method comprising administering to a tympanic membrane of an animal in need or want thereof a therapeutically-effective amount of a peptide comprising:
  a) a sequence of any one of SEQ ID NOS: 187-369; or
  b) a derivative of P13 comprising at least one D-amino acid residue, wherein the peptide optionally further comprises a transducing sequence at the C-terminus.

In some embodiments, the invention contemplates a use of a peptide in the manufacture of a medicament for regulating cellular activity, the peptide comprising:
  a) a sequence of any one of SEQ ID NOS: 187-368; or
  b) a derivative of P13 comprising at least one D-amino acid residue, wherein the peptide optionally further comprises a transducing sequence at the C-terminus.

In some embodiments, the invention contemplates a use of a peptide in the manufacture of a medicament for treating inflammation in an animal, the peptide comprising:
  a) a sequence of any one of SEQ ID NOS: 187-368; or
  b) a derivative of P13 comprising at least one D-amino acid residue, wherein the peptide optionally further comprises a transducing sequence at the C-terminus.

In some embodiments, the invention contemplates a use of a peptide in the manufacture of a medicament for treating sinusitis, the medicament comprising an aerosol composition, the peptide comprising:

a) a sequence of any one of SEQ ID NOS: 187-369; or b) a derivative of P13 comprising at least one D-amino acid residue, wherein the peptide optionally further comprises a transducing sequence at the C-terminus.

In some embodiments, the invention contemplates a use of a peptide in the manufacture of a medicament for improving hearing in an animal, wherein the animal has middle and/or inner ear inflammation and reduced hearing, the peptide comprising:

a) a sequence of any one of SEQ ID NOS: 187-369; or b) a derivative of P13 comprising at least one D-amino acid residue, wherein the peptide optionally further comprises a transducing sequence at the C-terminus, wherein the medicament is a topical medicament.

In some embodiments, the invention contemplates a use of a peptide in the manufacture of a medicament for treating middle and/or inner ear inflammation, wherein the medicament is suitable for administration to a tympanic membrane of an animal in need or want thereof, the peptide comprising:

a) a sequence of any one of SEQ ID NOS: 187-369; or b) a derivative of P13 comprising at least one D-amino acid residue, wherein the peptide optionally further comprises a transducing sequence at the C-terminus.

INCORPORATION BY REFERENCE

Figure 1:
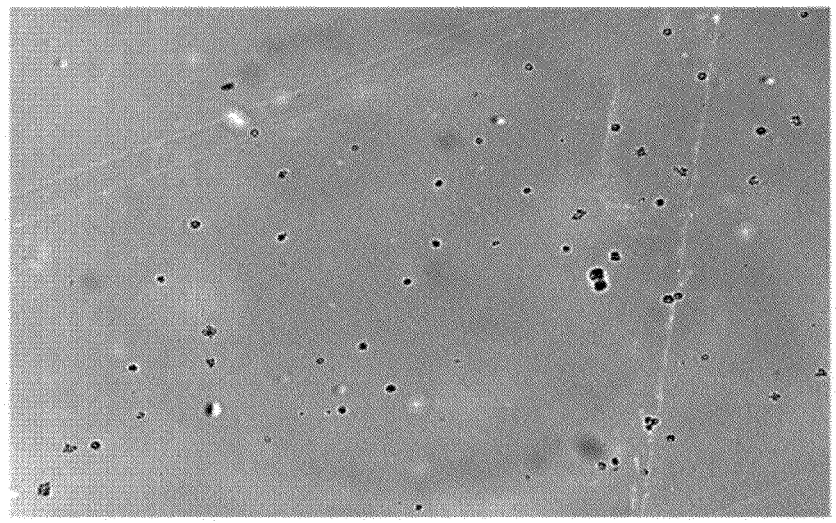
FIG. 1: Illustrates, in Panels A and B, an assay for crossing the tympanic membrane by FITC-labeled P13. Panel A. Bright field microscopy demonstrates cells in middle ear fluid. Panel B. Fluorescent microscopy demonstrates FITC-labeled P13 associated with cells in middle ear fluid.
Figure 1:
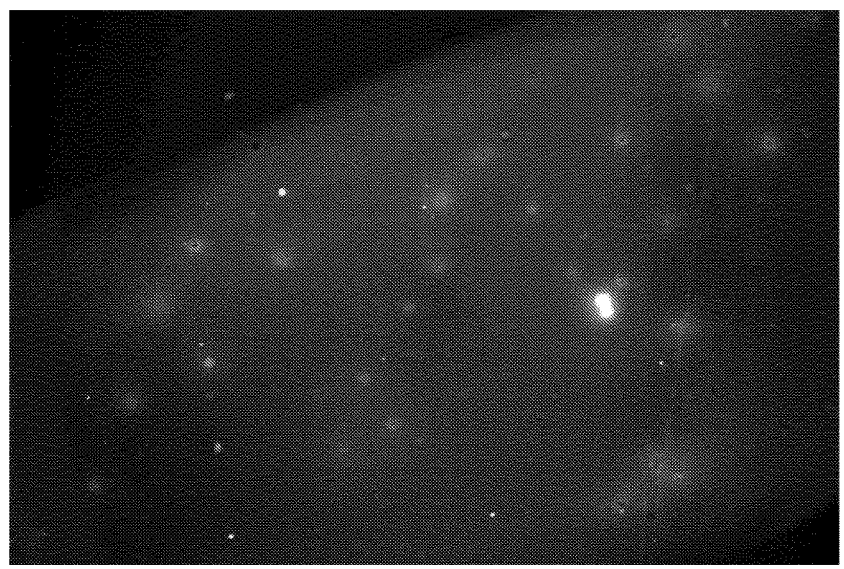

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

The treatment and control of natural and pathogen-induced inflammation represents a significant clinical challenge. The targeting of the TLR/TIR signaling cascade represents one approach to control inflammation; thus the identification of peptides derived from the A52R protein or A52R-like proteins finds therapeutic applications. The peptides and pharmaceutical compositions of the invention disclosed herein, and uses and methods of using the same, present a solution to the problem of controlling inflammation and regulating cellular pathways associated with inflammation.

Throughout the disclosure, amino acid residues of the peptides of the invention are referenced by one or both of the standard abbreviations known in the art: a) single-letter abbreviations, such as R for arginine, D for aspartic acid, V for valine, etc.; and b) three-letter abbreviations, such as Arg for arginine, Asp for aspartic acid, Val for valine, etc. The invention contemplates both L- and D-forms of amino acid residues. In cases wherein the abbreviation refers only to an amino acid residue of the D-configuration, the abbreviation is preceded by the term, "D-;" for example, D-Arg for D-arginine, D-Asp for D-aspartic acid, D-Val for D-valine, etc.

Toll-Like Receptor Signaling

Toll-Like receptors ("TLRs") are conserved molecular receptors that recognize structures from bacteria, fungi, protozoa, and viruses. Activation of TLRs initiates a series of intracellular events resulting in an innate immune response characterized by the production of pro-inflammatory cytokines (References 2-9). TLR signaling originates from the cytoplasmic Toll/interleukin-1 receptor (TIR) domain, conserved among all TLRs. Not limited by any theory, in certain embodiments, adapter molecule MyD88, containing both a TIR domain and a death domain, can associate with the TIR domain of TLRs and IRAK proteins. Phosphorylation of IRAK can then lead to association with TRAF6 and subsequent activation of NF-κB and secretion of pro-inflammatory cytokines (References 14, 22-25).

Peptides

Vaccinia virus, a member of the poxvirus family, is a DNA virus that has been demonstrated to encode immunomodulatory proteins (References 15-18). One of these proteins, A52R, has been shown to inhibit NF-κB activation following initiation of the TIR signaling cascade (References 15 and 18). Recent studies have demonstrated that A52R inhibits TR signaling and contributes to the virulence of vaccinia virus. In certain embodiments, cell activation in response to different PAMPs involves a number of intracellular molecules common to all TLRs, including but not limited to MyD88, members of the IL-1 receptor-associated kinase (IRAK) proteins, TNF receptor associated factor (TRAF6), and NF-κB (Reference 1).

Harte and colleagues (Reference 18) have demonstrated that the A52R protein inhibits TIR signaling by binding to both IRAK2 and TRAF6. Deletion of the A52R protein from vaccinia virus results in reduced viral virulence.

The peptide 13 ("P13") sequence (DIVKLTVYDCI (SEQ ID NO: 369)) was derived from the A52R sequence from vaccinia virus. Blast search analysis shows that peptide P13 has 100% homology with sequences found within larger proteins from vaccinia virus other than A52R, two proteins from cowpox virus, and one protein from rabbit pox virus. Peptide 13 was shown to have significant homology with three separate proteins from different strains of variola (smallpox) virus: i) A46L from variola major virus strain India; ii) A49L from variola minor virus Garcia; and iii) A44L from variola major virus strain.

P13 inhibits toll-like receptor-dependent signaling (U.S. Pat. No. 7,192,930 and US2008/0039395 incorporated herein by reference in their entirety). In some embodiments, structure-activity testing can be performed to identify amino acid residues in the P13 sequence that can be substituted for enhanced activity.

In some embodiments, the present invention provides a pharmaceutical composition comprising a peptide derived from A52R. In some embodiments, the pharmaceutical composition is an aural pharmaceutical composition.

In some embodiments, the peptide is P13. In some embodiments, the peptide is derived from P13. In some embodiments, the peptide is a P13 variant, derivative, stereoisomer, or analogue. In some embodiments, the peptide comprises the amino acid sequence LEEYFMY (SEQ ID NO: 370). In some embodiments, the peptide comprises the amino acid sequence FTILEEYFMY (SEQ ID NO: 371). In some embodiments, the peptide comprises the amino acid sequence DIVKLTVYDCI (SEQ ID NO: 369). In some embodiments, the peptide comprises the amino acid sequence VYDCI (SEQ ID NO: 372). In some embodiments, the peptide comprises the amino acid sequence VYACI (SEQ ID NO: 373). In some embodiments, the peptide comprises the amino acid sequence KLTVY (SEQ ID NO: 374). In some embodiments, the peptide comprises the amino acid sequence KLYVY (SEQ ID NO: 375). In some embodiments, the peptide comprises the amino acid sequence KVYVY (SEQ ID NO: 376). In some embodiments, the peptide comprises 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues. In some embodiments, the peptide comprises from 7-50 residues.

In some embodiments, a peptide comprises a transducing sequence. The transducing sequence can participate in cellular uptake. The presence of the transducing sequence can lead to enhanced or selective cellular uptake. In some embodiments, the transducing sequence is at the N-terminus of the peptide. In some embodiments, the transducing sequence is at the C-terminus of the peptide.

A non-limiting example of a transducing sequence is a poly-arginine sequence. In some embodiments, the poly-arginine sequence comprises arginine residues. In some embodiments, the poly-arginine sequence consists of arginine residues. In specific embodiments, the transducing sequence comprises 3, 4, 5, 6, 7, 8, 9, 10, 11, 12, 13, 14, 15, or 20 arginine residues. In some embodiments, the transducing sequence comprises nine arginine residues (SEQ ID NO: 379). In some embodiments, the transducing sequence consists of nine arginine residues (SEQ ID NO: 379). The arginine residues of the transducing sequence can be L-arginine, D-arginine, or a mixture of L- and D-arginine.

Table 1 provides non-limiting examples of peptides of the invention. Exemplary peptides 1-130 are those derived from A52R. Of peptides 1-130, a subset is further designated S1-S22. Other examples include peptides derived from P13 ("T peptides"). In some embodiments, the present invention provides a pharmaceutical composition comprising a peptide comprising any amino acid sequence listed in Table 1. In some embodiments, the present invention provides a pharmaceutical composition comprising any peptide listed in Table 1. In some embodiments, the present invention provides a pharmaceutical composition comprising a peptide comprising any amino acid sequence of S1-S22. In some embodiments, the present invention provides a pharmaceutical composition comprising any peptide of S1-S22. In some embodiments, the present invention provides a pharmaceutical composition comprising a peptide comprising any amino acid sequence of T1-T56. In some embodiments, the present invention provides a pharmaceutical composition comprising any peptide of T1-T56. In some embodiments, the peptide has a transducing sequence. In some embodiments, the transducing sequence is poly-arginine. In some embodiments, the peptide comprises the sequence of any one of SEQ ID NOS: 42-44, 68-77, 79-81, 83, 102-106, 133, 141, 151, 166, 167, 181, 182, 228-230, 254-263, 265-267, 269, 288-292, 319, 327, 337, 352, 353, 367, and 368. In some embodiments, the peptide comprises the sequence of T3, T11, T21, T36, T37, T51, or T52. In some embodiments, the peptide comprises the sequence of $T3-R^9$, $T11-R^9$, $T21-R^9$, $T36-R^9$, $T37-R^9$, $T51-R^9$, or $T52-R^9$.

TABLE 1

Exemplary peptides of the invention

| Peptide | Sequence |
|---|---|
| $1-R^9$ | YIKVQKQDIVKLTVYDCISMIGLCARRRRRRRRR (SEQ ID NO: 1) |
| $2-R^9$ | IKVQKQDIVKLTVYDCISMIGLCARRRRRRRRR (SEQ ID NO: 2) |
| $3-R^9$ | KVQKQDIVKLTVYDCISMIGLCARRRRRRRRR (SEQ ID NO: 3) |
| $4-R^9$ | VQKQDIVKLTVYDCISMIGLCARRRRRRRRR (SEQ ID NO: 4) |
| $5-R^9$ | QKQDIVKLTVYDCISMIGLCARRRRRRRRR (SEQ ID NO: 5) |
| $6-R^9$ | KQDIVKLTVYDCISMIGLCARRRRRRRRR (SEQ ID NO: 6) |
| $7-R^9$ | QDIVKLTVYDCISMIGLCARRRRRRRRR (SEQ ID NO: 7) |
| $8-R^9$ | DIVKLTVYDCISMIGLCARRRRRRRRR (SEQ ID NO: 8) |
| $9-R^9$ | IVKLTVYDCISMIGLCARRRRRRRRR (SEQ ID NO: 9) |
| $10-R^9$ | VKLTVYDCISMIGLCARRRRRRRRR (SEQ ID NO: 10) |
| $11-R^9$ | KLTVYDCISMIGLCARRRRRRRRR (SEQ ID NO: 11) |
| $12-R^9$ | LTVYDCISMIGLCARRRRRRRRR (SEQ ID NO: 12) |

TABLE 1-continued

Exemplary peptides of the invention

| Peptide | Sequence |
|---|---|
| 13-$R^9$ | TVYDCISMIGLCARRRRRRRRR (SEQ ID NO: 13) |
| 14-$R^9$ | VYDCISMIGLCARRRRRRRRR (SEQ ID NO: 14) |
| 15-$R^9$ | YDCISMIGLCARRRRRRRRR (SEQ ID NO: 15) |
| 16-$R^9$ | DCISMIGLCARRRRRRRRR (SEQ ID NO: 16) |
| 17-$R^9$ | CISMIGLCARRRRRRRRR (SEQ ID NO: 17) |
| 18-$R^9$ | ISMIGLCARRRRRRRRR (SEQ ID NO: 18) |
| 19-$R^9$ | SMIGLCARRRRRRRRR (SEQ ID NO: 19) |
| 20-$R^9$ | MIGLCARRRRRRRRR (SEQ ID NO: 20) |
| 21-$R^9$ | IGLCARRRRRRRRR (SEQ ID NO: 21) |
| 22-$R^9$ | YIKVQKQDIVKLTVYDCISMIGLCRRRRRRRRR (SEQ ID NO: 22) |
| 23-$R^9$ | YIKVQKQDIVKLTVYDCISMIGLRRRRRRRRR (SEQ ID NO: 23) |
| 24-$R^9$ | YIKVQKQDIVKLTVYDCISMIGRRRRRRRRR (SEQ ID NO: 24) |
| 25-$R^9$ | YIKVQKQDIVKLTVYDCISMIRRRRRRRRR (SEQ ID NO: 25) |
| 26-$R^9$ | YIKVQKQDIVKLTVYDCISMRRRRRRRRR (SEQ ID NO: 26) |
| 27-$R^9$ | YIKVQKQDIVKLTVYDCISRRRRRRRRR (SEQ ID NO: 27) |
| 28-$R^9$ | YIKVQKQDIVKLTVYDCIRRRRRRRRR (SEQ ID NO: 28) |
| 29-$R^9$ | YIKVQKQDIVKLTVYDCRRRRRRRRR (SEQ ID NO: 29) |
| 30-$R^9$ | YIKVQKQDIVKLTVYDRRRRRRRRR (SEQ ID NO: 30) |
| 31-$R^9$ | YIKVQKQDIVKLTVYRRRRRRRRR (SEQ ID NO: 31) |
| 32-$R^9$ | YIKVQKQDIVKLTVRRRRRRRRR (SEQ ID NO: 32) |
| 33-$R^9$ | YIKVQKQDIVKLTRRRRRRRRR (SEQ ID NO: 33) |
| 34-$R^9$ | YIKVQKQDIVKLRRRRRRRRR (SEQ ID NO: 34) |
| 35-$R^9$ | YIKVQKQDIVKRRRRRRRRR (SEQ ID NO: 35) |
| 36-$R^9$ | YIKVQKQDIVRRRRRRRRR (SEQ ID NO: 36) |
| 37-$R^9$ | YIKVQKQDIRRRRRRRRR (SEQ ID NO: 37) |
| 38-$R^9$ | YIKVQKQDRRRRRRRRR (SEQ ID NO: 38) |
| 39-$R^9$ | YIKVQKQRRRRRRRRR (SEQ ID NO: 39) |
| 40-$R^9$ | YIKVQKRRRRRRRRR (SEQ ID NO: 40) |
| 41-$R^9$ | YIKVQRRRRRRRRR (SEQ ID NO: 41) |
| 42(S1)-$R^9$ | EMFTILEEYFMYRGLLGLRIKYGRLFNEIRRRRRRRRR (SEQ ID NO: 42) |
| 43(S2)-$R^9$ | MFTILEEYFMYRGLLGLRIKYGRLFNEIRRRRRRRRR (SEQ ID NO: 43) |
| 44(S3)-$R^9$ | FTILEEYFMYRGLLGLRIKYGRLFNEIRRRRRRRRR (SEQ ID NO: 44) |
| 45-$R^9$ | TILEEYFMYRGLLGLRIKYGRLFNEIRRRRRRRRR (SEQ ID NO: 45) |
| 46-$R^9$ | ILEEYFMYRGLLGLRIKYGRLFNEIRRRRRRRRR (SEQ ID NO: 46) |
| 47-$R^9$ | LEEYFMYRGLLGLRIKYGRLFNEIRRRRRRRRR (SEQ ID NO: 47) |
| 48-$R^9$ | EEYFMYRGLLGLRIKYGRLFNEIRRRRRRRRR (SEQ ID NO: 48) |
| 49-$R^9$ | EYFMYRGLLGLRIKYGRLFNEIRRRRRRRRR (SEQ ID NO: 49) |
| 50-$R^9$ | YFMYRGLLGLRIKYGRLFNEIRRRRRRRRR (SEQ ID NO: 50) |

TABLE 1-continued

Exemplary peptides of the invention

| Peptide | Sequence |
|---|---|
| 51-R$^9$ | FMYRGLLGLRIKYGRLFNEIRRRRRRRRR (SEQ ID NO: 51) |
| 52-R$^9$ | MYRGLLGLRIKYGRLFNEIRRRRRRRRR (SEQ ID NO: 52) |
| 53-R$^9$ | YRGLLGLRIKYGRLFNEIRRRRRRRRR (SEQ ID NO: 53) |
| 54-R$^9$ | RGLLGLRIKYGRLFNEIRRRRRRRRR (SEQ ID NO: 54) |
| 55-R$^9$ | GLLGLRIKYGRLFNEIRRRRRRRRR (SEQ ID NO: 55) |
| 56-R$^9$ | LLGLRIKYGRLFNEIRRRRRRRRR (SEQ ID NO: 56) |
| 57-R$^9$ | LGLRIKYGRLFNEIRRRRRRRRR (SEQ ID NO: 57) |
| 58-R$^9$ | GLRIKYGRLFNEIRRRRRRRRR (SEQ ID NO: 58) |
| 59-R$^9$ | LRIKYGRLFNEIRRRRRRRRR (SEQ ID NO: 59) |
| 60-R$^9$ | RIKYGRLFNEIRRRRRRRRR (SEQ ID NO: 60) |
| 61-R$^9$ | IKYGRLFNEIRRRRRRRRR (SEQ ID NO: 61) |
| 62-R$^9$ | KYGRLFNEIRRRRRRRRR (SEQ ID NO: 62) |
| 63-R$^9$ | YGRLFNEIRRRRRRRRR (SEQ ID NO: 63) |
| 64-R$^9$ | GRLFNEIRRRRRRRRR (SEQ ID NO: 64) |
| 65-R$^9$ | RLFNEIRRRRRRRRR (SEQ ID NO: 65) |
| 66-R$^9$ | LFNEIRRRRRRRRR (SEQ ID NO: 66) |
| 67-R$^9$ | EMFTILEEYFMYRGLLGLRIKYGRLFNERRRRRRRRR (SEQ ID NO: 67) |
| 68 (S4)-R$^9$ | EMFTILEEYFMYRGLLGLRIKYGRLFNRRRRRRRRR (SEQ ID NO: 68) |
| 69 (S5)-R$^9$ | EMFTILEEYFMYRGLLGLRIKYGRLFRRRRRRRRR (SEQ ID NO: 69) |
| 70 (S6)-R$^9$ | EMFTILEEYFMYRGLLGLRIKYGRLRRRRRRRRR (SEQ ID NO: 70) |
| 71 (S7)-R$^9$ | EMFTILEEYFMYRGLLGLRIKYGRRRRRRRRRR (SEQ ID NO: 71) |
| 72 (S8)-R$^9$ | EMFTILEEYFMYRGLLGLRIKYGRRRRRRRRR (SEQ ID NO: 72) |
| 73 (S9)-R$^9$ | EMFTILEEYFMYRGLLGLRIKYRRRRRRRRR (SEQ ID NO: 73) |
| 74 (S10)-R$^9$ | EMFTILEEYFMYRGLLGLRIKRRRRRRRRR (SEQ ID NO: 74) |
| 75 (S11)-R$^9$ | EMFTILEEYFMYRGLLGLRIRRRRRRRRR (SEQ ID NO: 75) |
| 76 (S12)-R$^9$ | EMFTILEEYFMYRGLLGLRRRRRRRRRR (SEQ ID NO: 76) |
| 77 (S13)-R$^9$ | EMFTILEEYFMYRGLLGLRRRRRRRRR (SEQ ID NO: 77) |
| 78-R$^9$ | EMFTILEEYFMYRGLLGRRRRRRRRR (SEQ ID NO: 78) |
| 79 (S14)-R$^9$ | EMFTILEEYFMYRGLLRRRRRRRRR (SEQ ID NO: 79) |
| 80 (S15)-R$^9$ | EMFTILEEYFMYRGLRRRRRRRRR (SEQ ID NO: 80) |
| 81 (S16)-R$^9$ | EMFTILEEYFMYRGRRRRRRRRR (SEQ ID NO: 81) |
| 82-R$^9$ | EMFTILEEYFMYRRRRRRRRR (SEQ ID NO: 82) |
| 83 (S17)-R$^9$ | EMFTILEEYFMYRRRRRRRRR (SEQ ID NO: 83) |
| 84-R$^9$ | EMFTILEEYFMRRRRRRRRR (SEQ ID NO: 84) |
| 85-R$^9$ | EMFTILEEYFRRRRRRRRR (SEQ ID NO: 85) |
| 86-R$^9$ | EMFTILEEYRRRRRRRRR (SEQ ID NO: 86) |
| 87-R$^9$ | EMFTILEERRRRRRRRR (SEQ ID NO: 87) |
| 88-R$^9$ | EMFTILERRRRRRRRR (SEQ ID NO: 88) |

TABLE 1-continued

Exemplary peptides of the invention

| Peptide | Sequence |
|---|---|
| 89-R$^9$ | EMFTILRRRRRRRRR (SEQ ID NO: 89) |
| 90-R$^9$ | EMFTIRRRRRRRRR (SEQ ID NO: 90) |
| 91-R$^9$ | MFTILLEEYFMYRGLLRRRRRRRRR (SEQ ID NO: 91) |
| 92-R$^9$ | FTILLEEYFMYRGLLRRRRRRRRR (SEQ ID NO: 92) |
| 93-R$^9$ | TILLEEYFMYRGLLRRRRRRRRR (SEQ ID NO: 93) |
| 94-R$^9$ | ILLEEYFMYRGLLRRRRRRRRR (SEQ ID NO: 94) |
| 95-R$^9$ | LLEEYFMYRGLLRRRRRRRRR (SEQ ID NO: 95) |
| 96-R$^9$ | LEEYFMYRGLLRRRRRRRRR (SEQ ID NO: 96) |
| 97-R$^9$ | EYFMYRGLLRRRRRRRRR (SEQ ID NO: 97) |
| 98-R$^9$ | YFMYRGLLRRRRRRRRR (SEQ ID NO: 98) |
| 99-R$^9$ | FMYRGLLRRRRRRRRR (SEQ ID NO: 99) |
| 100-R$^9$ | MYRGLLRRRRRRRRR (SEQ ID NO: 100) |
| 101-R$^9$ | YRGLLRRRRRRRRR (SEQ ID NO: 101) |
| 102 (S18)-R$^9$ | MFTILEEYFMYRGLLGLRIRRRRRRRRR (SEQ ID NO: 102) |
| 103 (S19)-R$^9$ | FTILLEEYFMYRGLLGLRIRRRRRRRRR (SEQ ID NO: 103) |
| 104 (S20)-R$^9$ | TILLEEYFMYRGLLGLRIRRRRRRRRR (SEQ ID NO: 104) |
| 105 (S21)-R$^9$ | ILLEEYFMYRGLLGLRIRRRRRRRRR (SEQ ID NO: 105) |
| 106 (S22)-R$^9$ | LLEEYFMYGLLGLRIRRRRRRRRR (SEQ ID NO: 106) |
| 107-R$^9$ | EYFMYRGLLGLRIKYGRRRRRRRRR (SEQ ID NO: 107) |
| 108-R$^9$ | YFMYRGLLGLRIKYGRRRRRRRRR (SEQ ID NO: 108) |
| 109-R$^9$ | FMYRGLLGLRIKYGRRRRRRRRR (SEQ ID NO: 109) |
| 110-R$^9$ | MYRGLLGLRIKYGRRRRRRRRR (SEQ ID NO: 110) |
| 111-R$^9$ | YRGLLGLRIKYGRRRRRRRRR (SEQ ID NO: 111) |
| 112-R$^9$ | RGLLGLRIKYGRRRRRRRRR (SEQ ID NO: 112) |
| 113-R$^9$ | GLLGLRIKYGRRRRRRRRR (SEQ ID NO: 113) |
| 114-R$^9$ | LLGLRIKYGRRRRRRRRR (SEQ ID NO: 114) |
| 115-R$^9$ | LGLRIKYGRRRRRRRRR (SEQ ID NO: 115) |
| 116-R$^9$ | GLRIKYGRRRRRRRRR (SEQ ID NO: 116) |
| 117-R$^9$ | LRIKYGRRRRRRRRR (SEQ ID NO: 117) |
| 118-R$^9$ | RIKYGRRRRRRRRR (SEQ ID NO: 118) |
| 119-R$^9$ | EEYFMRRRRRRRRR (SEQ ID NO: 119) |
| 120-R$^9$ | EEYFMYRRRRRRRRR (SEQ ID NO: 120) |
| 121-R$^9$ | EEYFMYRRRRRRRRRR (SEQ ID NO: 121) |
| 122-R$^9$ | EEYFMYRGRRRRRRRRR (SEQ ID NO: 122) |
| 123-R$^9$ | EEYFMYRGLRRRRRRRRR (SEQ ID NO: 123) |
| 124-R$^9$ | EEYFMYRGLLRRRRRRRRR (SEQ ID NO: 124) |
| 125-R$^9$ | EEYFMYRGLLGRRRRRRRRR (SEQ ID NO: 125) |
| 126-R$^9$ | EEYFMYRGLLGLRRRRRRRRR (SEQ ID NO: 126) |

TABLE 1-continued

Exemplary peptides of the invention

| Peptide | Sequence |
|---|---|
| 127-R9 | EEYFMYRGLLGLRRRRRRRRR (SEQ ID NO: 127) |
| 128-R9 | EEYFMYRGLLGLRIRRRRRRRRR (SEQ ID NO: 128) |
| 129-R9 | EEYFMYRGLLGLRIKRRRRRRRRR (SEQ ID NO: 129) |
| 130-R9 | EEYFMYRGLLGLRIKYRRRRRRRRR (SEQ ID NO: 130) |
| T1-R9 | IVKLTVYDCIRRRRRRRRR (SEQ ID NO: 131) |
| T2-R9 | DIVKLTVYDCRRRRRRRRR (SEQ ID NO: 132) |
| T3-R9 | AIVKLTVYDCIRRRRRRRRR (SEQ ID NO: 133) |
| T4-R9 | DAVKLTVYDCIRRRRRRRRR (SEQ ID NO: 134) |
| T5-R9 | DIAKLTVYDCIRRRRRRRRR (SEQ ID NO: 135) |
| T6-R9 | DIVALTVYDCIRRRRRRRRR (SEQ ID NO: 136) |
| T7-R9 | DIVKATVYDCIRRRRRRRRR (SEQ ID NO: 137) |
| T8-R9 | DIVKLAVYDCIRRRRRRRRR (SEQ ID NO: 138) |
| T9-R9 | DIVKLTAYDCIRRRRRRRRR (SEQ ID NO: 139) |
| T10-R9 | DIVKLTVADCIRRRRRRRRR (SEQ ID NO: 140) |
| T11-R9 | DIVKLTVYACIRRRRRRRRR (SEQ ID NO: 141) |
| T12-R9 | DIVKLTVYDAIRRRRRRRRR (SEQ ID NO: 142) |
| T13-R9 | DIVKLTVYDCARRRRRRRRR (SEQ ID NO: 143) |
| T14-R9 | EIVKLTVYDCIRRRRRRRRR (SEQ ID NO: 144) |
| T15-R9 | DIVKLTVYECIRRRRRRRRR (SEQ ID NO: 145) |
| T16-R9 | DIVRLTVYDCIRRRRRRRRR (SEQ ID NO: 146) |
| T17-R9 | DIVHLTVYDCIRRRRRRRRR (SEQ ID NO: 147) |
| T18-R9 | KIVKLTVYKCIRRRRRRRRR (SEQ ID NO: 148) |
| T19-R9 | DIVELTVYDCIRRRRRRRRR (SEQ ID NO: 149) |
| T20-R9 | DIVKLSVYDCIRRRRRRRRR (SEQ ID NO: 150) |
| T21-R9 | DIVKLYVYDCIRRRRRRRRR (SEQ ID NO: 151) |
| T22-R9 | DIVKLTVSDCIRRRRRRRRR (SEQ ID NO: 152) |
| T23-R9 | DIVKLTVTDCIRRRRRRRRR (SEQ ID NO: 153) |
| T24-R9 | DIVKLTVWDCIRRRRRRRRR (SEQ ID NO: 154) |
| T25-R9 | DIVKLTVFDCIRRRRRRRRR (SEQ ID NO: 155) |
| T26-R9 | DIVKLTVYDMIRRRRRRRRR (SEQ ID NO: 156) |
| T27-R9 | DIVKLTVYDSIRRRRRRRRR (SEQ ID NO: 157) |
| T28-R9 | DIVKLTVYDXaaIRRRRRRRRR (SEQ ID NO: 158) |
| T29-R9 | DIVKLTVYDXaaIRRRRRRRRR (SEQ ID NO: 159) |
| T30-R9 | DIVKLTVYDXaaIRRRRRRRRR (SEQ ID NO: 160) |
| T31-R9 | DIVKLTVYDXaaIRRRRRRRRR (SEQ ID NO: 161) |
| T32-R9 | DIVKLTVYDXaaIRRRRRRRRR (SEQ ID NO: 162) |
| T33-R9 | DLVKLTVYDCIRRRRRRRRR (SEQ ID NO: 163) |
| T34-R9 | DVVKLTVYDCIRRRRRRRRR (SEQ ID NO: 164) |

TABLE 1-continued

Exemplary peptides of the invention

| Peptide | Sequence |
|---|---|
| T35-R[9] | DILKLTVYDCIRRRRRRRRR (SEQ ID NO: 165) |
| T36-R[9] | DIIKLTVYDCIRRRRRRRRR (SEQ ID NO: 166) |
| T37-R[9] | DIVKVTVYDCIRRRRRRRRR (SEQ ID NO: 167) |
| T38-R[9] | DIVKITVYDCIRRRRRRRRR (SEQ ID NO: 168) |
| T39-R[9] | DIVKLTLYDCIRRRRRRRRR (SEQ ID NO: 169) |
| T40-R[9] | DIVKLTIYDCIRRRRRRRRR (SEQ ID NO: 170) |
| T41-R[9] | DIVKLTVYDCLRRRRRRRRR (SEQ ID NO: 171) |
| T42-R[9] | DIVKLTVYDCVRRRRRRRRR (SEQ ID NO: 172) |
| T43-R[9] | DIDKLTEYDSIRRRRRRRRR (SEQ ID NO: 173) |
| T44-R[9] | DIPKLGVPDCIRRRRRRRRR (SEQ ID NO: 174) |
| T45-R[9] | ICDYVTLKVIDRRRRRRRRR (SEQ ID NO: 175) |
| T46-R[9] | VDLVIDCIYKTRRRRRRRRR (SEQ ID NO: 176) |
| T47-R[9] | DIVKLTVYDCIDIVKLTVYDCIRRRRRRRRR (SEQ ID NO: 177) |
| T48-R[9] | IVKLTVYDCIRRRRRRRRR (N-succinyl) (SEQ ID NO: 178) |
| T49-R[9] | DIVKLTVYDCIGRRRRRRRRR (SEQ ID NO: 179) |
| T50-R[9] | DIVKLTVYDCIRRRRRRRRR (N-acetyl) (SEQ ID NO: 180) |
| T51-R[9] | AIVKLTVYACIRRRRRRRRR (SEQ ID NO: 181) |
| T52-R[9] | AIIKVYVYACIRRRRRRRRR (SEQ ID NO: 182) |
| T53 | D-Asp-D-Ile-D-Val-D-Lys-D-Leu-D-Thr-D-Val-D-Tyr-D-Asp-D-Cys-D-Ile-Arg-Arg-Arg-Arg-Arg-Arg-Arg-Arg-Arg (SEQ ID NO: 183) |
| T54 | D-Asp-D-Ile-D-Val-D-Lys-D-Leu-D-Thr-D-Val-D-Tyr-D-Asp-D-Cys-D-Ile-D-Arg-D-Arg-D-Arg-D-Arg-D-Arg-D-Arg-D-Arg-D-Arg-D-Arg (SEQ ID NO: 184) |
| T55 | D-Asp-D-Ile-D-Val-D-Lys-D-Leu-D-Thr-D-Val-D-Tyr-D-Asp-D-Cys-D-Ile (SEQ ID NO: 185) |
| T56 | Asp-Ile-Val-Lys-Leu-Thr-Val-Tyr-Asp-Cys-Ile-D-Arg-D-Arg-D-Arg-D-Arg-D-Arg-D-Arg-D-Arg-D-Arg-D-Arg (SEQ ID NO: 186) |
| 1 | YIKVQKQDIVKLTVYDCISMIGLCA (SEQ ID NO: 187) |
| 2 | IKVQKQDIVKLTVYDCISMIGLCA (SEQ ID NO: 188) |
| 3 | KVQKQDIVKLTVYDCISMIGLCA (SEQ ID NO: 189) |
| 4 | VQKQDIVKLTVYDCISMIGLCA (SEQ ID NO: 190) |
| 5 | QKQDIVKLTVYDCISMIGLCA (SEQ ID NO: 191) |
| 6 | KQDIVKLTVYDCISMIGLCA (SEQ ID NO: 192) |
| 7 | QDIVKLTVYDCISMIGLCA (SEQ ID NO: 193) |
| 8 | DIVKLTVYDCISMIGLCA (SEQ ID NO: 194) |
| 9 | IVKLTVYDCISMIGLCA (SEQ ID NO: 195) |
| 10 | VKLTVYDCISMIGLCA (SEQ ID NO: 196) |
| 11 | KLTVYDCISMIGLCA (SEQ ID NO: 197) |
| 12 | LTVYDCISMIGLCA (SEQ ID NO: 198) |

TABLE 1-continued

Exemplary peptides of the invention

| Peptide | Sequence |
|---|---|
| 13 | TVYDCISMIGLCA (SEQ ID NO: 199) |
| 14 | VYDCISMIGLCA (SEQ ID NO: 200) |
| 15 | YDCISMIGLCA (SEQ ID NO: 201) |
| 16 | DCISMIGLCA (SEQ ID NO: 202) |
| 17 | CISMIGLCA (SEQ ID NO: 203) |
| 18 | ISMIGLCA (SEQ ID NO: 204) |
| 19 | SMIGLCA (SEQ ID NO: 205) |
| 20 | MIGLCA (SEQ ID NO: 206) |
| 21 | IGLCA (SEQ ID NO: 207) |
| 22 | YIKVQKQDIVKLTVYDCISMIGLC (SEQ ID NO: 208) |
| 23 | YIKVQKQDIVKLTVYDCISMIGL (SEQ ID NO: 209) |
| 24 | YIKVQKQDIVKLTVYDCISMIG (SEQ ID NO: 210) |
| 25 | YIKVQKQDIVKLTVYDCISMI (SEQ ID NO: 211) |
| 26 | YIKVQKQDIVKLTVYDCISM (SEQ ID NO: 212) |
| 27 | YIKVQKQDIVKLTVYDCIS (SEQ ID NO: 213) |
| 28 | YIKVQKQDIVKLTVYDCI (SEQ ID NO: 214) |
| 20 | YIKVQKQDIVKLTVYDC (SEQ ID NO: 215) |
| 30 | YIKVQKQDIVKLTVYD (SEQ ID NO: 216) |
| 31 | YIKVQKQDIVKLTVY (SEQ ID NO: 217) |
| 32 | YIKVQKQDIVKLTV (SEQ ID NO: 218) |
| 33 | YIKVQKQDIVKLT (SEQ ID NO: 219) |
| 34 | YIKVQKQDIVKL (SEQ ID NO: 220) |
| 35 | YIKVQKQDIVK (SEQ ID NO: 221) |
| 36 | YIKVQKQDIV (SEQ ID NO: 222) |
| 37 | YIKVQKQDI (SEQ ID NO: 223) |
| 38 | YIKVQKQD (SEQ ID NO: 224) |
| 39 | YIKVQKQ (SEQ ID NO: 225) |
| 40 | YIKVQK (SEQ ID NO: 226) |
| 41 | YIKVQ (SEQ ID NO: 227) |
| 42 (S1) | EMFTILEEYFMYRGLLGLRIKYGRLFNEI (SEQ ID NO: 228) |
| 43 (S2) | MFTILEEYFMYRGLLGLRIKYGRLFNEI (SEQ ID NO: 229) |
| 44 (S3) | FTILEEYFMYRGLLGLRIKYGRLFNEI (SEQ ID NO: 230) |
| 45 | TILEEYFMYRGLLGLRIKYGRLFNEI (SEQ ID NO: 231) |
| 46 | ILEEYFMYRGLLGLRIKYGRLFNEI (SEQ ID NO: 232) |
| 47 | LEEYFMYRGLLGLRIKYGRLFNEI (SEQ ID NO: 233) |
| 48 | EEYFMYRGLLGLRIKYGRLFNEI (SEQ ID NO: 234) |
| 49 | EYFMYRGLLGLRIKYGRLFNEI (SEQ ID NO: 235) |
| 50 | YFMYRGLLGLRIKYGRLFNEI (SEQ ID NO: 236) |

TABLE 1-continued

Exemplary peptides of the invention

| Peptide | Sequence |
|---|---|
| 51 | FMYRGLLGLRIKYGRLFNEI (SEQ ID NO: 237) |
| 52 | MYRGLLGLRIKYGRLFNEI (SEQ ID NO: 238) |
| 53 | YRGLLGLRIKYGRLFNEI (SEQ ID NO: 239) |
| 54 | RGLLGLRIKYGRLFNEI (SEQ ID NO: 240) |
| 55 | GLLGLRIKYGRLFNEI (SEQ ID NO: 241) |
| 56 | LLGLRIKYGRLFNEI (SEQ ID NO: 242) |
| 57 | LGLRIKYGRLFNEI (SEQ ID NO: 243) |
| 58 | GLRIKYGRLFNEI (SEQ ID NO: 244) |
| 59 | LRIKYGRLFNEI (SEQ ID NO: 245) |
| 60 | RIKYGRLFNEI (SEQ ID NO: 246) |
| 61 | IKYGRLFNEI (SEQ ID NO: 247) |
| 62 | KYGRLFNEI (SEQ ID NO: 248) |
| 63 | YGRLFNEI (SEQ ID NO: 249) |
| 64 | GRLFNEI (SEQ ID NO: 250) |
| 65 | RLFNEI (SEQ ID NO: 251) |
| 66 | LFNEI (SEQ ID NO: 252) |
| 67 | EMFTILEEYFMYRGLLGLRIKYGRLFNE (SEQ ID NO: 253) |
| 68 (S4) | EMFTILEEYFMYRGLLGLRIKYGRLFN (SEQ ID NO: 254) |
| 69 (S5) | EMFTILEEYFMYRGLLGLRIKYGRLF (SEQ ID NO: 255) |
| 70 (S6) | EMFTILEEYFMYRGLLGLRIKYGRL (SEQ ID NO: 256) |
| 71 (S7) | EMFTILEEYFMYRGLLGLRIKYG R (SEQ ID NO: 257) |
| 72 (S8) | EMFTILEEYFMYRGLLGLRIKYG (SEQ ID NO: 258) |
| 73 (S9) | EMFTILEEYFMYRGLLGLRIKY (SEQ ID NO: 259) |
| 74 (S10) | EMFTILEEYFMYRGLLGLRIK (SEQ ID NO: 260) |
| 75 (S11) | EMFTILEEYFMYRGLLGLRI (SEQ ID NO: 261) |
| 76 (S12) | EMFTILEEYFMYRGLLGL R (SEQ ID NO: 262) |
| 77 (S13) | EMFTILEEYFMYRGLLGL (SEQ ID NO: 263) |
| 78 | EMFTILEEYFMYRGLLG (SEQ ID NO: 264) |
| 79 (S14) | EMFTILEEYFMYRGLL (SEQ ID NO: 265) |
| 80 (S15) | EMFTILEEYFMYRGL (SEQ ID NO: 266) |
| 81 (S16) | EMFTILEEYFMYRG (SEQ ID NO: 267) |
| 82 | EMFTILEEYFMY R (SEQ ID NO: 268) |
| 83 (S17) | EMFTILEEYFMY (SEQ ID NO: 269) |
| 84 | EMFTILEEYFM (SEQ ID NO: 270) |
| 85 | EMFTILEEYF (SEQ ID NO: 271) |
| 86 | EMFTILEEY (SEQ ID NO: 272) |
| 87 | EMFTILEE (SEQ ID NO: 273) |
| 88 | EMFTILE (SEQ ID NO: 274) |

TABLE 1-continued

Exemplary peptides of the invention

| Peptide | Sequence |
|---|---|
| 89 | EMFTIL (SEQ ID NO: 275) |
| 90 | EMFTI (SEQ ID NO: 276) |
| 91 | MFTILLEEYFMYRGLL (SEQ ID NO: 277) |
| 92 | FTILLEEYFMYRGLL (SEQ ID NO: 278) |
| 93 | TILLEEYFMYRGLL (SEQ ID NO: 279) |
| 94 | ILLEEYFMYRGLL (SEQ ID NO: 280) |
| 95 | LLEEYFMYRGLL (SEQ ID NO: 281) |
| 96 | LEEYFMYRGLL (SEQ ID NO: 282) |
| 97 | EYFMYRGLL (SEQ ID NO: 283) |
| 98 | YFMYRGLL (SEQ ID NO: 284) |
| 99 | FMYRGLL (SEQ ID NO: 285) |
| 100 | MYRGLL (SEQ ID NO: 286) |
| 101 | YRGLL (SEQ ID NO: 287) |
| 102 (S18) | MFTILEEYFMYRGLLGLRI (SEQ ID NO: 288) |
| 103 (S19) | FTILEEYFMYRGLLGLRI (SEQ ID NO: 289) |
| 104 (S20) | TILLEEYFMYRGLLGLRI (SEQ ID NO: 290) |
| 105 (S21) | ILLEEYFMYRGLLGLRI (SEQ ID NO: 291) |
| 106 (S22) | LLEEYFMYGLLGLRI (SEQ ID NO: 292) |
| 107 | EYFMYRGLLGLRIKYG (SEQ ID NO: 293) |
| 108 | YFMYRGLLGLRIKYG (SEQ ID NO: 294) |
| 109 | FMYRGLLGLRIKYG (SEQ ID NO: 295) |
| 110 | MYRGLLGLRIKYG (SEQ ID NO: 296) |
| 111 | YRGLLGLRIKYG (SEQ ID NO: 297) |
| 112 | RGLLGLRIKYG (SEQ ID NO: 298) |
| 113 | GLLGLRIKYG (SEQ ID NO: 299) |
| 114 | LLGLRIKYG (SEQ ID NO: 300) |
| 115 | LGLRIKYG (SEQ ID NO: 301) |
| 116 | GLRIKYG (SEQ ID NO: 302) |
| 117 | LRIKYG (SEQ ID NO: 303) |
| 118 | RIKYG (SEQ ID NO: 304) |
| 119 | EEYFM (SEQ ID NO: 305) |
| 120 | EEYFMY (SEQ ID NO: 306) |
| 121 | EEYFMY R (SEQ ID NO: 307) |
| 122 | EEYFMYRG (SEQ ID NO: 308) |
| 123 | EEYFMYRGL (SEQ ID NO: 309) |
| 124 | EEYFMYRGLL (SEQ ID NO: 310) |
| 125 | EEYFMYRGLLG (SEQ ID NO: 311) |
| 126 | EEYFMYRGLLGL (SEQ ID NO: 312) |

TABLE 1-continued

Exemplary peptides of the invention

| Peptide | Sequence |
|---|---|
| 127 | EEYFMYRGLLGL R (SEQ ID NO: 313) |
| 128 | EEYFMYRGLLGLRI (SEQ ID NO: 314) |
| 129 | EEYFMYRGLLGLRIK (SEQ ID NO: 315) |
| 130 | EEYFMYRGLLGLRIKY (SEQ ID NO: 316) |
| T1 | IVKLTVYDCI (SEQ ID NO: 317) |
| T2 | DIVKLTVYDC (SEQ ID NO: 318) |
| T3 | AIVKLTVYDCI (SEQ ID NO: 319) |
| T4 | DAVKLTVYDCI (SEQ ID NO: 320) |
| T5 | DIAKLTVYDCI (SEQ ID NO: 321) |
| T6 | DIVALTVYDCI (SEQ ID NO: 322) |
| T7 | DIVKATVYDCI (SEQ ID NO: 323) |
| T8 | DIVKLAVYDCI (SEQ ID NO: 324) |
| T9 | DIVKLTAYDCI (SEQ ID NO: 325) |
| T10 | DIVKLTVADCI (SEQ ID NO: 326) |
| T11 | DIVKLTVYACI (SEQ ID NO: 327) |
| T12 | DIVKLTVYDAI (SEQ ID NO: 328) |
| T13 | DIVKLTVYDCA (SEQ ID NO: 329) |
| T14 | EIVKLTVYDCI (SEQ ID NO: 330) |
| T15 | DIVKLTVYECI (SEQ ID NO: 331) |
| T16 | DIVRLTVYDCI (SEQ ID NO: 332) |
| T17 | DIVHLTVYDCI (SEQ ID NO: 333) |
| T18 | KIVKLTVYKCI (SEQ ID NO: 334) |
| T19 | DIVELTVYDCI (SEQ ID NO: 335) |
| T20 | DIVKLSVYDCI (SEQ ID NO: 336) |
| T21 | DIVKLYVYDCI (SEQ ID NO: 337) |
| T22 | DIVKLTVSDCI (SEQ ID NO: 338) |
| T23 | DIVKLTVTDCI (SEQ ID NO: 339) |
| T24 | DIVKLTVWDCI (SEQ ID NO: 340) |
| T25 | DIVKLTVFDCI (SEQ ID NO: 341) |
| T26 | DIVKLTVYDMI (SEQ ID NO: 342) |
| T27 | DIVKLTVYDSI (SEQ ID NO: 343) |
| T28 | DIVKLTVYDXaaI (SEQ ID NO: 344) |
| T29 | DIVKLTVYDXaaI (SEQ ID NO: 345) |
| T30 | DIVKLTVYDXaaI (SEQ ID NO: 346) |
| T31 | DIVKLTVYDXaaI (SEQ ID NO: 347) |
| T32 | DIVKLTVYDXaaI (SEQ ID NO: 348) |
| T33 | DLVKLTVYDCI (SEQ ID NO: 349) |
| T34 | DVVKLTVYDCI (SEQ ID NO: 350) |

TABLE 1-continued

Exemplary peptides of the invention

| Peptide | Sequence |
|---|---|
| T35 | DILKLTVYDCI (SEQ ID NO: 351) |
| T36 | DIIKLTVYDCI (SEQ ID NO: 352) |
| T37 | DIVKVTVYDCI (SEQ ID NO: 353) |
| T38 | DIVKITVYDCI (SEQ ID NO: 354) |
| T39 | DIVKLTLYDCI (SEQ ID NO: 355) |
| T40 | DIVKLTIYDCI (SEQ ID NO: 356) |
| T41 | DIVKLTVYDCL (SEQ ID NO: 357) |
| T42 | DIVKLTVYDCV (SEQ ID NO: 358) |
| T43 | DIDKLTEYDSI (SEQ ID NO: 359) |
| T44 | DIPKLGVPDCI (SEQ ID NO: 360) |
| T45 | ICDYVTLKVID (SEQ ID NO: 361) |
| T46 | VDLVIDCIYKT (SEQ ID NO: 362) |
| T47 | DIVKLTVYDCIDIVKLTVYDCI (SEQ ID NO: 363) |
| T48 | IVKLTVYDCI (N-succinyl) (SEQ ID NO: 364) |
| T49 | DIVKLTVYDCIG (SEQ ID NO: 365) |
| T50 | DIVKLTVYDCI (N-acetyl) (SEQ ID NO: 366) |
| T51 | AIVKLTVYACI (SEQ ID NO: 367) |
| T52 | AIIKVYVYACI (SEQ ID NO: 368) |

Legend to Table 1:
Xaa in peptide T31 and T31-$R^9$ is α-Aminobutyric acid;
Xaa in peptide T32 and T32-$R^9$ is L-Norvaline;
Xaa in peptide T30 and T30-$R^9$ is L-Cysteine(S-Acm);
Xaa in peptide T28 and T28-$R^9$ is L-Cysteine(S-carboxymethyl); and
Xaa in peptide T29 and T29-$R^9$ is L-Cysteine(S-carbamidomethyl).

Peptides of the invention and compositions comprising the same are effective to modulate cellular activity. In some embodiments, modulating cellular activity is accomplished by modulating cellular signaling. Activities can be regulated, for example, by a toll-like receptor. In some embodiments, peptides and compositions of the invention inhibit cytokine secretion. In some embodiments, peptides and compositions of the invention enhance cytokine secretion. In some embodiments, cytokine secretion is in response to toll-like receptor-dependent stimulation.

In some embodiments, administration of a peptide derived from A52R or P13 can inhibit cytokine secretion by at least 10%, 20%, 30%, 40%, 50%, 60%, 70%, 80% or 90%. In some embodiments, administration of a peptide derived from A52R or P13 can enhance cytokine secretion by 10%, 20%, 30%, 40%, 50%, 60%, 70%, 80% or 90%. In some embodiments the cytokine secretion is a result of TLR-dependent signaling.

In some embodiments, the activity mediated by a toll-like receptor is TNF-α secretion. Peptides and compositions of the invention are effective to provide 10%, 20%, 30%, 40%, 50%, 60%, 70%, 80% or 90% inhibition of TNF-α secretion following stimulation by LPS. Peptides and compositions of the invention are effective to provide 10%, 20%, 30%, 40%, 50%, 60%, 70%, 80% or 90% inhibition of TNF-α secretion following stimulation by CpG-ODN. Peptides and compositions of the invention are effective to provide 10%, 20%, 30%, 40%, 50%, 60%, 70%, 80% or 90% inhibition of TNF-α secretion following stimulation by LPS and/or CpG-ODN. Peptides and compositions of the invention are effective to provide 10%, 20%, 30%, 40%, 50%, 60%, 70%, 80% or 90% enhancement of TNF-α secretion following stimulation by LPS. Peptides and compositions of the invention are effective to provide 10%, 20%, 30%, 40%, 50%, 60%, 70%, 80% or 90% enhancement of TNF-α secretion following stimulation by CpG-ODN. Peptides and compositions of the invention are effective to provide 10%, 20%, 30%, 40%, 50%, 60%, 70%, 80% or 90% enhancement of TNF-α secretion following stimulation by LPS and/or CpG-ODN.

Some embodiments of the invention contemplate a peptide comprising the amino acid sequence DIVKLTVYDCI (SEQ ID NO: 369), linked to a 9-arginine (SEQ ID NO: 379) cell transduction sequence or other type of cell transduction sequence. The peptide DIVKLTVYDCIRRRRRRRRR (SEQ ID NO: 378) effectively inhibits cytokine secretion in response to TLR activation. The peptide had no effect on cytokine secretion resulting from cell activation that was initiated independent of TLR stimulation. Employing a mouse model of otitis media with effusion (OME), administration of heat-inactivated Streptococcus pneumoniae (S. pneumoniae) into the middle ears of BALB/c mice resulted in a significant inflammatory response that was dramatically reduced with peptide treatment. Experiments have also demonstrated that the peptide will reduce pro-inflammatory mediators in a mouse model of LPS-induced septic shock. The peptide is effective in the treatment of chronic inflammation initiated by bacterial or viral infections.

In some embodiments, the invention contemplates a pharmaceutical composition effective to:

a) decrease the amount of an middle ear fluid by about 30-80%;

b) decrease infiltrating cell number in middle ear fluid by about 30-80%; and c) decrease the thickness of a tympanic membrane by about 30-80% in a mouse comprising inflammation of the ear, wherein the composition is administered to the mouse in an amount of about 0.1 µg to 60 µg. In some embodiments, the pharmaceutical composition is an aural pharmaceutical composition. In some embodiments, the pharmaceutical composition is formulated for intra-aural administration. In some embodiments, the pharmaceutical composition is formulated as a drop. In some embodiments, the pharmaceutical composition is formulated as an ear drop.

In some embodiments, a pharmaceutical composition of the invention comprises a peptide. In some embodiments, the peptide is P13 or a variant, derivative, stereoisomer, or analogue thereof. In some embodiments, the peptide is P13, a peptide comprising P13 and a poly-argenine domain, or a peptide of Table 1. In some embodiments, the peptide is P13. In some embodiments, the peptide is derived from A52R. In some embodiments, the peptide is a peptide of S1-S22. The invention also contemplates a method of treating ear inflammation in an animal in need or want thereof, the method comprising administering to the animal a pharmaceutical composition of the invention.

The in vivo effectiveness of P13 was demonstrated using a mouse model of otitis media (OM). OM is an inflammatory disease of the middle ear accompanied by fluid accumulation. It is characterized by an infiltration of leukocytes, macrophages, and mast cells and a release of inflammatory mediators and enzymes (Reference 21). These mediators increase vascular permeability and secretory activity, and initiate a cascade of inflammatory events, resulting in fluid accumulation and mucin secretion (References 26 and 27). The initiation of inflammation in OM has been attributed to a variety of factors, including bacterial or viral infections, Eustachian tube dysfunction, and allergy. However, the evidence points to a bacterial etiology leading to cytokine activation in the majority of cases. Bacteria have been cultured from up to 40% of effusions and studies have shown bacterial DNA by PCR in approximately 80% of effusions, often in the absence of viable organisms in culture (Reference 28). The most common bacteria invading the middle ear are S. pneumoniae, H. influenzae, and M. catarralis. These three bacteria account for 85% of acute middle ear infections (Reference 27), with S. pneumoniae being the most frequent cause. Initially, live bacteria trigger acute inflammation, which is designed to eliminate the pathogen. During acute infection, interference with the innate immune response would be potentially harmful to the host and can lead to further bacterial spread. Acute inflammation initiated by bacterial infections self-resolves or is treatable by antibiotics. Chronic inflammation involves continued activation of the immune system, often by non-viable bacterial products. OM is often prolonged or antibiotic resistant, suggesting TLR stimulation in the absence of live bacteria.

Treatment of mice with P13 in the experiments disclosed herein resulted in a significant reduction in bacterial-induced inflammation in the middle ear. Fluid accumulation, infiltrating cells, and tympanic membrane thickness in the middle ear were all dramatically reduced with peptide treatment. Administration of heat-inactivated bacteria, which have a number of potential TLR ligands, induced an inflammatory response in the middle ear most likely resulting from activation of multiple TLRs. The use of heat-inactivated bacteria allowed for an examination of peptide inhibition of inflammation without the potential for the bacterial spread that can occur in an acute infection initiated with live bacteria. The ability of peptide P13 to inhibit this response significantly in vivo is consistent with the in vitro data showing inhibition of cytokine secretion in response to multiple TLR ligands used either individually or in combination. In these studies, a single dose of peptide was administered at the same time as heat-inactivated S. pneumoniae into the middle ears of normal BALB/c mice. The in vitro data also showed inhibition of cytokine secretion even when peptide P13 was added several hours after initiation of TLR activation.

In addition to P13 and the peptides of Table 1, the invention disclosed herein also contemplates peptides more broadly characterized as variants, derivatives, stereoisomers, or analogues of any peptide of the instant invention. These terms are not exclusive, and can be contemplated in concert to describe peptides that are described by one or more of the terms. Many such peptides, not all of which are expressly disclosed herein, are contemplated as peptides, as components of a formulation or pharmaceutical composition, and as elements of the methods and uses of the instant invention.

In some embodiments, the variant, derivative, stereoisomer, or analogue of a peptide of the invention comprises a peptide comprising a peptide of the invention and a poly-argenine sequence. In some embodiments, the variant, derivative, stereoisomer, or analogue of a peptide of the invention comprises one or more D-amino acid residues. In some embodiments, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 of the amino acid residues of the variant, derivative, stereoisomer, or analogue of a peptide of the invention possess the D-configuration. In some embodiments, all the amino acid residues of the variant, derivative, stereoisomer, or analogue of a peptide of the invention possess the D-configuration.

In some embodiments, the variant, derivative, stereoisomer, or analogue of a peptide of the invention comprises one or more D-amino acid residues in the region of the peptide analogous to or derived from a peptide of the invention. In some embodiments, the region of the peptide analogous to or derived from P13 comprises more than one D-amino acid residue.

In some embodiments, the region of the peptide analogous to or derived from a peptide of the invention comprises a D-amino acid residue. In some embodiments, the poly-argenine sequence comprises a D-amino acid residue. In some embodiments, the poly-argenine sequence comprises more than one D-amino acid residue. In some embodiments, either the region of the peptide analogous to or derived from a peptide of the invention or the poly-argenine sequence comprises a D-amino acid residue. In some embodiments, either the region of the peptide analogous to or derived from a peptide of the invention or the poly-argenine sequence comprises more than one D-amino acid residue. In some embodiments, both the region of the peptide analogous to or derived from a peptide of the invention and the poly-argenine sequence independently comprise a D-amino acid residue. In some embodiments, both the region of the peptide analogous to or derived from a peptide of the invention and the poly-argenine sequence independently comprise more than one D-amino acid residue.

In some embodiments comprising a peptide comprising a variant, derivative, stereoisomer, or analogue of a peptide of the invention comprising a poly-argenine sequence, the region of the peptide analogous to or derived from P13 consists of D-amino acid residues. In some embodiments, the region of the peptide analogous to or derived from a peptide of the invention consists of D-amino acid residues, and the poly-argenine sequence consists of L-amino acid residues. In some embodiments, the region of the peptide analogous to or derived from a peptide of the invention consists of D-amino acid residues, and the poly-argenine sequence comprises one or more D-amino acid residues.

In some embodiments, the poly-argenine sequence consists of D-amino acid residues. In some embodiments, the poly-argenine sequence consists of D-amino acid residues, and the region of the peptide analogous to or derived from a peptide of the invention consists of L-amino acid residues. In some embodiments, the poly-argenine sequence consists of D-amino acid residues, and the region of the peptide analogous to or derived from a peptide of the invention comprises one or more D-amino acid residues.

In some embodiments comprising a peptide comprising a variant, derivative, stereoisomer, or analogue of a peptide of the invention comprising a poly-argenine sequence, the peptide consists of D-amino acid residues.

In some embodiments, a peptide comprises an amino acid residue comprising a stereogenic side chain, for example, threonine, allo-threonine, isoleucine, or allo-isoleucine. In some embodiments, a peptide comprises a D-allo-threonine, or D-allo-isoleucine residue.

Diseases

The initiation of an inflammatory response to pathogens is a component of the innate immune response and is designed to control infection. However, the sustained production of inflammatory mediators can lead to chronic inflammation, tissue damage and disease development. The signaling cascade initiated by PAMP/TLR interactions and culminating in cell activation has been associated with many disease states, including otitis media, inner ear inflammation, sepsis, autoimmune diseases, asthma, heart disease and cancer (Reference 29). OM is an inflammatory disease of the middle ear. OM is often prolonged or antibiotic resistant; these characteristics suggest TLR stimulation in the absence of live bacteria. An abnormal TLR signaling response could lead to exaggerated cell-activation responses contributing to sepsis (Reference 30 and 31).

Inflammation is also an aspect of autoimmunity, and is hypothesized to play a role in tissue destruction in diseases such as multiple sclerosis, rheumatoid arthritis and insulin-dependent diabetes mellitus (Reference 32). Cells of the innate immune system have an essential role in acquired/adaptive immunity. TLR proteins are involved in the maturation and activation of dendritic cells, the antigen-presenting cell type considered most relevant to development of acquired immunity (Reference 33). Allergic asthma is an example of a chronic inflammatory disease with an adaptive immune response, and the TLR signaling pathway is implicated in the induction phase of an allergic phenotype (Reference 30). Bacterial and viral infections, causing increased inflammatory cell activation, are the main cause of exacerbations in diseases such as asthma and COPD (chronic obstructive pulmonary disease) (Reference 30).

In some embodiments, the inflammation is caused by a virus, bacteria, fungi, antigen, self-antigen, or a combination thereof. In some embodiments, the inflammation is associated with a virus, bacteria, fungi, antigen, self-antigen, or a combination thereof. In some embodiments, the inflammation is correlated with a virus, bacteria, fungi, antigen, self-antigen, or a combination thereof. In some embodiments, the inflammation is accompanied by a virus, bacteria, fungi, antigen, self-antigen, or a combination thereof. In some embodiments, an organism having the inflammation also has a virus, bacteria, fungi, antigen, self-antigen, or a combination thereof.

In some embodiments, the peptides provided herein are administered to a subject for the treatment of inflammation. Non-limiting examples of the causes of inflammation include viral, bacterial or fungal infection. In some embodiments, the inflammation is a result of a response to a self-antigen or any other antigen. In some embodiments, the inflammation is a result of a response to an anti-self-antigen In some embodiments, the inflammation comprises inflammation of the ear. The inflammation of the ear can be inflammation of the inner ear and/or middle ear. In some embodiments, the inflammation comprises otitis media. In some embodiments, pharmaceutical compositions of the instant invention are used for the treatment of otitis media.

C3H/HeJ mice, defective in TLR4 signaling, are known to develop chronic otitis media ("COM") spontaneously. Such mice with inner ear inflammation may show sensorineural hearing loss in addition to middle ear conductive hearing loss. Histologic examination of the middle and inner ear of C3H/HeJ mice with COM has documented a thickening of the mucosal surfaces of the middle ear, thickening of the round window membrane, fibrosis, labyrinthitis, and Eustachian tube obstruction. These histologic changes correlate with the histology seen with human temporal bone from patients with a history of COM and labyrinthitis. The mouse studies have shown that C3H/HeJ mice with COM have gram-negative *Klebsiella* bacteria in the middle ear. The analogies between the observations in the mouse experiments and those in human COM and labrinthitis patients suggest that mouse experiments with a peptide or pharmaceutical composition of the invention disclosed herein provide results predictive of what the therapeutic effect would be in a human subject.

In some embodiments, otitis media is associated with hearing loss or reduced hearing. Administration of a peptide of the invention of a pharmaceutical composition thereof can improve the hearing of the affected organism back to ordinary hearing levels. In some embodiments, administration of a therapeutically-effective amount of a pharmaceutical composition to an organism in need or want thereof improves the hearing of the organism, wherein the organism has both otitis media and lessened hearing. In some embodiments, the peptide or pharmaceutical composition is administered topically. In some embodiments, upon administration of a peptide of the invention of a pharmaceutical composition thereof, an organism with hearing loss recovers hearing faster than hearing would be recovered without administration of the peptide or pharmaceutical composition.

In some embodiments, administration of a therapeutically-effective amount of a peptide of the invention or a pharmaceutical composition comprising the same to an organism with otitis media, wherein the organism is in need or want thereof, provides therapeutic relief of a symptom of otitis media. Non-limiting examples of the symptoms of otitis media include otalgia (pain), otorrhea, fever, irritability, anorexia, vomiting or diarrhea. In some embodiments, the symptom is pain.

In some embodiments, the inflammation comprises inflammation of the skin, joints, muscular tissue, brain, or connective tissue. In some embodiments, pharmaceutical compositions of the instant invention are used for the treatment of inflammation of the skin, joints, muscular tissue, brain, or connective tissue.

In some embodiments, the inflammation comprises arthritis, dermatitis, Lupus erythematosus, meningitis, or psoriasis. In some embodiments, the arthritis comprises osteoarthritis, rheumatoid arthritis, septic arthritis, gout, pseudo-gout, juvenile idiopathic arthritis, Still's disease, or ankylosing spondylitis. In some embodiments, the dermatitis comprises spongiotic dermatitis, childhood eczema, allergic contact dermatitis, seborrhoeic dermatitis, dyshidrotic dermatitis, urticaria, vesicular or bullous dermatitis, or papular urticaria. In some embodiments, the psoriasis comprises plaque psoriasis, flexural psoriasis, guttate psoriasis, pustular psoriasis, nail psoriasis, psoriatic arthritis, or erythrodermic psoriasis.

In some embodiments, the administration comprises topical application. In some embodiments, the administration comprises topical application to the skin, hair, outer ear, tympanic membrane, nasal cavity, buccal cavity, or sublingual cavity.

In some embodiments, the peptides of the invention and pharmaceutical composition comprising the same are effective for the treatment of sinusitis. In some embodiments, administration of a pharmaceutical composition of the invention to an organism in need or want thereof provides a therapeutic effect on sinusitis or a symptom thereof. Non-limiting examples of symptoms of sinusitis include stuffy or runny nose, nasal discharge, bloody nasal discharge, sneezing, coughing, nasal pain, headache, postnasal drip, itchy face, diminished scent or taste senses, bad breath, fever, chill, dental pain, or face pain. In some embodiments, a pharmaceutical composition of the invention is administered as an aerosol, vapor, spray, or mist.

Therapeutic Uses

A, "patient," "subject," or "host," to be treated with a pharmaceutical composition of the present invention may mean either a human or non-human animal. In some embodiments, the subject is human. The peptides of the present invention are useful in the treatment of such diseases and disorders such as but not limited to those involving inflammation. In one embodiment, the peptides and pharmaceutical compositions of the present invention may be used in the manufacture of a medicament for any number of uses, including, for example, treating any disease or other treatable condition of a patient.

A, "therapeutic effect," as the term is used herein, encompasses a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. A prophylactic effect includes delaying or eliminating the appearance of a disease or condition, delaying or eliminating the onset of symptoms of a disease or condition, slowing, halting, or reversing the progression of a disease or condition, or any combination thereof.

Administration

A pharmaceutical composition containing a peptide can be administered to patients along with pharmaceutical excipients or diluents. Non-limiting examples of suitable pharmaceutical excipients or diluents include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol, buffered water, phosphate buffered saline and the like. These compositions can take the form of drops, solutions, suspensions, tablets, pills, capsules, powders, sustained-release formulations and the like. In some embodiments, the composition is an ear drop. In another preferred embodiment the composition containing a peptide in any form could be further modulated using suitable excipients and diluents including lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions can be formulated in a unit dosage form, each dosage containing, for example, from about 1 ng to 1000 mg of the peptide. In some embodiments, a dose contains from 100-1000 mg of the peptide. In some embodiments, a dose contains from 100-500 mg of the peptide. In some embodiments, a dose contains from 200-300 mg of the peptide The term, "unit dosage form," refers to physically discrete units suitable as unitary dosages for human subjects and other mammals, each unit containing a predetermined quantity of active material calculated to produce the desired therapeutic effect, in association with a suitable pharmaceutical diluents or excipients. These may be administered to humans, domestic pets, livestock, or other animals with a pharmaceutically-acceptable diluents or excipients, in unit dosage form. Administration may be topical, intraaural, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration. Formulations for oral use include tablets containing the active ingredient(s) in a mixture with non-toxic pharmaceutically-acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

The active therapeutic formulation of the invention can be provided in lyophilized form for reconstituting, for instance, in isotonic, aqueous, or saline buffers for parental, subcutaneous, intradermal, intramuscular or intravenous administration. The subject composition of the invention may also be administered to the patient in need of a therapeutic peptide by liquid preparations for orifice, e.g. oral, intraaural, nasal, or sublingual, administration such as suspensions, syrups or elixirs. The subject composition of the invention may also be prepared for oral administration such as capsules, tablets, pills, and the like, as well as chewable solid formulations. The subject composition of the invention may also be prepared as a cream for dermal administration such as liquid, viscous liquid, paste, or powder. The subject composition of the invention may also be prepared as powder for lung administration with or without aerosolizing component. The composition of the invention can be prepared as a drop, for example, an ear drop.

The presently disclosed compositions can be used for delivery in oral, intraaural, intranasal, sublingual, intraduodenal, subcutaneous, buccal, intracolonic, rectal, vaginal, mucosal, pulmonary, transdermal, intradermal, parenteral, intravenous, intramuscular and ocular forms as well as being able to traverse the blood-brain barrier.

Dosages

The dosage of any peptide of the present invention will vary depending on the symptoms, age and body weight of the patient, the nature and severity of the disorder to be treated or prevented, the route of administration, and the form of the composition. Any of the subject formulations may be administered in a single dose or in divided doses. Dosages for the peptides of the present invention may be readily determined by techniques known to those of skill in the art or as taught herein. Also, the present invention contemplates mixtures of more than one subject peptide, as well as other therapeutic agents.

In certain embodiments, the dosage of the subject peptide will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular peptide of the present invention. This may be accomplished by routine experiment as described herein, using one or more groups of animals, or in human trials if appropriate. The effectiveness of any peptide and method of treatment or prevention may be assessed by administering the supplement and assessing the effect of the administration by measuring one or more indices associated with the neoplasm of interest, and comparing the post-treatment values of these indices to the values of the same indices prior to treatment.

The precise time of administration and amount of any particular peptide that will yield the most effective treatment in a given patient will depend upon the activity, pharmacokinetics, and bioavailability of a particular peptide, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the subject may be monitored by measuring one or more of the relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of peptide administered and possibly to the time of administration may be made based on these reevaluations.

Treatment may be initiated with smaller dosages which are less than the optimum dose of the peptide. Thereafter, the dosage may be increased by small increments until the optimum therapeutic effect is attained.

The combined use of several peptides of the present invention, or alternatively other peptides, may reduce the required dosage for any individual component because the onset and duration of effect of the different components may be complimentary. In such combined therapy, the different peptides may be delivered together or separately, and simultaneously or at different times within the day.

Toxicity and therapeutic efficacy of subject peptides may be determined by standard pharmaceutical procedures in cell cultures or experimental animals, e.g., for determining the $LD_{50}$ and the $ED_{50}$. Although peptides that exhibit toxic side effects may be used, care should be taken to design a delivery system that targets the peptides to the desired site in order to reduce side effects.

The data obtained from cell culture assays and animal studies may be used in formulating a range of dosage for use in humans. The dosage of any supplement, or alternatively of any components therein, lies preferably within a range of circulating concentrations that include the $ED_{50}$, with little or no toxicity. The dosage may vary within this range depending upon the dosage form employed and the route of administration utilized. For peptides of the present invention, the therapeutically effective dose may be estimated initially from cell culture assays. A dose may be formulated in animal models to achieve a circulating plasma concentration range that includes the $IC_{50}$ (i.e., the concentration of the test peptide which achieves a half-maximal inhibition of symptoms) as determined in cell culture. Such information may be used to more accurately determine useful doses in humans. Levels in plasma may be measured, for example, by high performance liquid chromatography (HPLC).

Formulations

The peptide-based compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. The peptide-based compositions can also be administered into deep lung by aerosolizing the composition into 1-5 um particle using standard techniques known in the art either with or without addition of aerosolizing excipient. For application by the ophthalmic mucous membrane route, compositions of the present invention may be formulated as eye drops or eye ointments. Aural pharmaceutical compositions can be formulated as ear drops, ointments, creams, liquids, gels, or salves for application to the ear, either internally or superficially. These formulations may be prepared by conventional means, and, if desired, the compositions may be mixed with any conventional additive, such as an excipient, a binder, a disintegrating agent, a lubricant, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject peptide-based compositions may be suitable for oral, intraaural, nasal, topical (including buccal and sublingual), rectal, vaginal, aerosol and/or parenteral administration. The formulations of the peptide-based compositions may conveniently be presented in unit dosage form and may be prepared by any methods well known in the art of pharmacy. The amounts of composition that may be combined with other excipients to produce a single dose may vary depending upon the subject being treated, and the particular mode of administration.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject peptide composition is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethyl cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the peptide compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically-acceptable emulsions, microemulsions, gels, solutions, suspensions, syrups and elixirs. The liquid dosage peptide formulation may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspension dosage of the peptide formulation may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The peptide formulations for rectal or vaginal administration may be presented as a suppository, which may be prepared by mixing a peptide with one or more suitable carriers and other excipients comprising, for example, cocoa butter, polyethylene glycol, a suppository wax or a salicylate, and which is solid at room temperature, but liquid at body temperature and, therefore, will melt in the body cavity and release peptide. Formulations which are suitable for vaginal administration also include pessaries, tampons, creams, gels, pastes, foams or spray formulations containing excipients as are known in the art to be appropriate.

The peptide dosage formulations for transdermal administration of a subject composition includes drops, powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a subject composition, excipients, such as animal and vegetable fats, oils, waxes, paraffin, starch, tragacanth, cellulose derivatives, polyethylene glycols, silicones, bentonite, silicic acid, talc and zinc oxide, or mixtures thereof. The peptide compositions of the present invention may also be in the form of baby wipes.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

The peptide compositions of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the peptide to shear, which may result in degradation of the peptides contained in the subject compositions.

Ordinarily, an aqueous aerosol is made by formulating an aqueous solution or suspension of a subject composition together with conventional pharmaceutically-acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

EXAMPLES

Example 1

Materials and Methods

Peptide of the Natural Configuration:
Peptides were synthesized by Mimotopes using their unique proprietary parallel array synthesis platform. Each peptide contains an amino acid sequence of the invention and optionally a 9-residue arginine (SEQ ID NO: 379) cell transduction sequence positioned at the C-terminus of the peptide to facilitate cellular uptake. The peptides are presented in Table 1.

Peptides with D-Amino Acid Residues are Synthesized as Peptides with L-Amino Acid Residues are Synthesized.

The D-amino acids with the appropriate protecting groups are commercially available for use on automated systems to construct peptides. Peptides described herein can be made entirely from L-amino acids, entirely from D-amino acids, or from a mixture of both in any proportion. A peptide is considered stereochemically-mixed if the peptide comprises at least one L-, and at least one D-amino acid residue. The transduction tag can similarly be made entirely from L-amino acids, entirely from D-amino acids, or from a mixture of both in any proportion. Peptides differing only in stereochemistry may possess differing properties, benefits, specificities, affinities, and activities at the same or at different receptors. In some cases, peptides differing only in stereochemistry may exhibit comparable specificities and activities.

Each peptide is constructed both with and without a FITC-label (Fluorescein isothiocyanate). FITC labeled peptides are used for FACS analysis. The peptides lacking the FITC label are used for in vitro inhibition assays and in vivo treatment studies.

Reagents:
Nuclease-resistant phosphorylated oligonucleotide was purchased from Oligos Etc., Inc. The sequence was 5'-TC-CATGACGTTCCTGACGTT-3' (SEQ ID NO: 377) (CpG-oligodeoxynucleotide (ODN). TNF-α assays were performed using assay kits purchased from R&D Systems. Mouse IL-1α and TNF-α were purchased from R&D Systems. PMA (phorbol myristate acetate) and LPS (Lipopolysaccharide) were purchased from Sigma. The TLR ligands flagellin, zymosan, and Poly (I:C) were purchased from Invivogen. Cytokine assays were performed using assay kits purchased from R&D Systems. (Heat-inactivated *S. pneumoniae* was the kind gift of Dr. Thomas DeMaria, The Ohio State University College of Medicine, Department of Otolaryngology, Columbus, Ohio.)

Cell Lines and Cultures:
RAW264.7 (murine monocyte/macrophage cells (American Type Culture Collection) were cultured at 37° C. in a 5% $CO_2$ humidified incubator and grown in DMEM (Invitrogen Life Technologies) supplemented with 10% (v/v) heat-inactivated FCS, 1.5 mM L-glutamine, 100 U/ml penicillin, and 100 μg/ml streptomycin.

Cytokine Secretion:
RAW264.7 cells were plated at $1.5 \times 10^5$ cells/well –$3 \times 10^5$ cells/well in 48-well plates. After 24 hours, the cells were incubated with peptides at various concentrations at room temperature in triplicate either before, simultaneous with, or after activation with various PAMPs for 18 hours. Cell-free supernatants were analyzed for cytokines by ELISA, in quadruplicate. RAW264.7 cells were stimulated with either CpG-ODN (1 μg/ml or 1.25 μg/ml), LPS (about 1 ng/ml), Poly (I:C) (about 10 μg/ml), flagellin (about 5 ng/ml), or zymosan (about 10 μg/ml). Dose response curves were done with each PAMP to determine optimal stimulation concentration. For CpG-ODN stimulation, cells were incubated for 4 hours at 37° C., supernatants collected, and TNF-α measured by ELISA. Any cytokine involved in inflammatory disease mediated toll receptor signaling can be measured using similar assays.

Flow Cytometry:
Cells are analyzed by flow cytometry (FACScan, Becton Dickinson) using Cellquest software to quantify internalization of peptides. Gates are drawn to exclude dead cells based on 7-AAD (7-amino-actinomycin D) staining Flourescence due to cell-surface binding of FITC-labeled peptides is quenched using trypan blue. Data obtained are geometric mean fluorescent units (F) with background autofluorescence subtracted.

Immunoblotting:
RAW264.7 cells ($6 \times 10^5$) are plated in 12 well plates overnight. Cells are incubated for 15 minutes at room temperature with peptides to be tested or control scrambled peptides, and then stimulated with medium or LPS (1 ng/ml) for either 15 or 30 minutes. Cells are lysed, and proteins fractionated by SDS/PAGE (Sodium Dodecyl Sulfate/Polyacrylamide Gel Electrophoresis) (12%). Immunoblotting is done using Phospho-IkB-α (Ser32) antibody (Cell Signaling), detected using horseradish peroxidase-conjugated secondary antibody, and visualized by chemiluminescence. Measurements of band intensity are made using the Nucleo Tech Gel Expert software linked to an Epson expression 636 scanner and expressed as intensity/area.

Cell Viability:
Cells were assayed for viability using CellTiter 96 Aq$_{ueous}$ One Solution Cell Proliferation Assay (Promega) following manufacturer's instructions. Briefly, cells were seeded in 96 well plates and incubated overnight at 37° C. in a humidified 5% $CO_2$ atmosphere. When samples were ready to be assayed, 20 μl of reagent was added into each well, and incubated for 1.5 hrs at 37° C. in a humidified 5% $CO_2$ atmosphere. Absorbances were read at 490 nm using an ELx800 absorbance microplate reader (BioTek) and data analyzed with GenS software (BioTek). Some peptides were evaluated for their effect on cell viability by trypan blue exclusion staining over a range of concentrations and then each peptide was tested for cytokine inhibition at the maximum concentration that had no effect on cell viability.

Example 2

Effect of Peptides on CpG-ODN-Induced Cytokine Secretion

The effect of several peptides on TNF-α secretion from RAW264.7 cells in response to stimulation by CpG-ODN was studied. Each peptide was initially tested at 3 concentrations, 37 μM, 22.2 μM, and 11.1 μM. Seventeen peptides demonstrating inhibition of TNF-α secretion of 50-100% across all three doses are presented (Table 2). The peptides were then tested at 11.1 μM, 7.4 μM, and 3.7 μM (Table 3). The peptides continued to demonstrate inhibitory activity at 7.4 μM, and twelve of the peptides had inhibitory activity at 3.7 μM. Cell viability was examined for each peptide at the concentrations tested for TNF-α inhibition. No decrease in cell viability was demonstrated.

TABLE 2

Percent Inhibition of TNF-α secretion by S1-S22 peptides with a $R^9$ sequence (SEQ ID NO: 379). RAW264.7 cells were plated at $3 \times 10^5$ cells/well in 48-well plates. After 24 h the cells were incubated with peptide at various concentrations at room temperature in triplicate for 15 minutes and then stimulated with 1 ug/ml Cpg-ODN. Cells were then incubated for 4 hours at 37° C., supernatants collected, and TNF-α measured by ELISA. Percent inhibition was calculated by comparing TNF-α secretion from cells incubated with peptide to control cells with no peptide treatment.

| Peptide | 37 µM | 22.2 µM | 11.1 µM | Sequence |
|---|---|---|---|---|
| 42 (S1)-$R^9$ | 97 | 96 | 85 | EMFTILEEYFMYRGLLGLRIKYGRLFNEIRRRRRRRRR (SEQ ID NO: 42) |
| 43 (S2)-$R^9$ | 100 | 94 | 91 | MFTILEEYFMYRGLLGLRIKYGRLFNEIRRRRRRRRR (SEQ ID NO: 43) |
| 44 (S3)-$R^9$ | 95 | 96 | 91 | FTILEEYFMYRGLLGLRIKYGRLFNEIRRRRRRRRR (SEQ ID NO: 44) |
| 68 (S4)-$R^9$ | 100 | 100 | 95 | EMFTILEEYFMYRGLLGLRIKYGRLFNRRRRRRRRR (SEQ ID NO: 68) |
| 69 (S5)-$R^9$ | 100 | 100 | 93 | EMFTILEEYFMYRGLLGLRIKYGRLFRRRRRRRRR (SEQ ID NO: 69) |
| 70 (S6)-$R^9$ | 100 | 100 | 93 | EMFTILEEYFMYRGLLGLRIKYGRLRRRRRRRRR (SEQ ID NO: 70) |
| 71 (S7)-$R^9$ | 91 | 82 | 56 | EMFTILEEYFMYRGLLGLRIKYGRRRRRRRRRR (SEQ ID NO: 71) |
| 72 (S8)-$R^9$ | 100 | 100 | 92 | EMFTILEEYFMYRGLLGLRIKYGRRRRRRRRRR (SEQ ID NO: 72) |
| 73 (S9)-$R^9$ | 100 | 100 | 84 | EMFTILEEYFMYRGLLGLRIKYRRRRRRRRRR (SEQ ID NO: 73) |
| 74 (S10)-$R^9$ | 100 | 100 | 91 | EMFTILEEYFMYRGLLGLRIKRRRRRRRRRR (SEQ ID NO: 74) |
| 75 (S11)-$R^9$ | 98 | 97 | 92 | EMFTILEEYFMYRGLLGLRIRRRRRRRRRR (SEQ ID NO: 75) |
| 76 (S12)-$R^9$ | 87 | 84 | 82 | EMFTILEEYFMYRGLLGLRRRRRRRRRRR (SEQ ID NO: 76) |
| 77 (S13)-$R^9$ | 93 | 89 | 84 | EMFTILEEYFMYRGLLGLRRRRRRRRRR (SEQ ID NO: 77) |
| 79 (S14)-$R^9$ | 97 | 93 | 85 | EMFTILEEYFMYRGLLRRRRRRRRRR (SEQ ID NO: 79) |
| 80 (S15)-$R^9$ | 91 | 87 | 78 | EMFTILEEYFMYRGLRRRRRRRRRR (SEQ ID NO: 80) |
| 81 (S16)-$R^9$ | 90 | 86 | 84 | EMFTILEEYFMYRGRRRRRRRRRR (SEQ ID NO: 81) |
| 83 (S17)-$R^9$ | 89 | 82 | 72 | EMFTILEEYFMYRRRRRRRRRR (SEQ ID NO: 83) |
| 102 (S18)-$R^9$ | — | 91 | 72 | MFTILEEYFMYRGLLGLRIRRRRRRRRR (SEQ ID NO: 102) |
| 103 (S19)-$R^9$ | | 99 | 93 | FTILEEYFMYRGLLGLRIRRRRRRRRRR (SEQ ID NO: 103) |
| 104 (S20)-$R^9$ | — | 93 | 74 | TILEEYFMYRGLLGLRIRRRRRRRRRR (SEQ ID NO: 104) |
| 105 (S21)-$R^9$ | — | 91 | 62 | ILEEYFMYRGLLGLRIRRRRRRRRRR (SEQ ID NO: 105) |
| 106 (S22)-$R^9$ | — | 92 | 70 | LEEYFMYGLLGLRIRRRRRRRRRR (SEQ ID NO: 106) |

TABLE 3

Inhibition of TNF-α secretion by S1-S22 peptides with an R$^9$ sequence (SEQ ID NO: 379). RAW264.7 cells were plated at 3X10$^5$ cells/well in 48-well plates. After 24 h the cells were incubated with peptide at various concentrations at room temperature in triplicate for 15 minutes and then stimulated with 1 ug/ml Cpg-ODN. Cells were then incubated for 4 hours at 37° C., supernatants collected, and TNF-α measured by ELISA. Percent inhibition was calculated by comparing TNF-α secretion from cells incubated with peptide to control cells with no peptide treatment.

| Peptide | 11 µM | 7 µM | 3.1 µM | Sequence |
|---|---|---|---|---|
| 42 (S1)-R$^9$ | 83 | 67 | 37 | EMFTILEEYFMYRGLLGLRIKYGRLFNEIRRRRRRRRR (SEQ ID NO: 42) |
| 43 (S2)-R$^9$ | 70 | 51 | 0 | MFTILEEYFMYRGLLGLRIKYGRLFNEIRRRRRRRRR (SEQ ID NO: 43) |
| 44 (S3)-R$^9$ | 78 | 24 | 0 | FTILEEYFMYRGLLGLRIKYGRLFNEIRRRRRRRRR (SEQ ID NO: 44) |
| 68 (S4)-R$^9$ | 95 | 83 | 69 | EMFTILEEYFMYRGLLGLRIKYGRLFNRRRRRRRRR (SEQ ID NO: 68) |
| 69 (S5)-R$^9$ | 93 | 94 | 66 | EMFTILEEYFMYRGLLGLRIKYGRLFRRRRRRRRR (SEQ ID NO: 69) |
| 70 (S6)-R$^9$ | 94 | 87 | 63 | EMFTILEEYFMYRGLLGLRIKYGRLRRRRRRRRR (SEQ ID NO: 70) |
| 71 (S7)-R$^9$ | 38 | 29 | 21 | EMFTILEEYFMYRGLLGLRIKYGRRRRRRRRRR (SEQ ID NO: 71) |
| 72 (S8)-R$^9$ | 93 | 80 | 43 | EMFTILEEYFMYRGLLGLRIKYGRRRRRRRRRR (SEQ ID NO: 72) |
| 73 (S9)-R$^9$ | 85 | 76 | 3 | EMFTILEEYFMYRGLLGLRIKYRRRRRRRRR (SEQ ID NO: 73) |
| 74 (S10)-R$^9$ | 92 | 80 | 35 | EMFTILEEYFMYRGLLGLRIKRRRRRRRRR (SEQ ID NO: 74) |
| 75 (S11)-R$^9$ | 93 | 84 | 31 | EMFTILEEYFMYRGLLGLRIRRRRRRRRR (SEQ ID NO: 75) |
| 76 (S12)-R$^9$ | 84 | 67 | 44 | EMFTILEEYFMYRGLLGLRRRRRRRRRR (SEQ ID NO: 76) |
| 77 (S13)-R$^9$ | 81 | 77 | 18 | EMFTILEEYFMYRGLLGLRRRRRRRRR (SEQ ID NO: 77) |
| 79 (S14)-R$^9$ | 86 | 77 | 0 | EMFTILEEYFMYRGLLRRRRRRRRR (SEQ ID NO: 79) |
| 80 (S15)-R$^9$ | 81 | 68 | 57 | EMFTILEEYFMYRGLRRRRRRRRR (SEQ ID NO: 80) |
| 81 (S16)-R$^9$ | 70 | 53 | 26 | EMFTILEEYFMYRGRRRRRRRRR (SEQ ID NO: 81) |
| 83 (S17)-R$^9$ | 57 | 44 | 0 | EMFTILEEYFMYRRRRRRRRRR (SEQ ID NO: 83) |
| 102 (S18)-R$^9$ | 72 | 48 | — | MFTILEEYFMYRGLLGLRIRRRRRRRRR (SEQ ID NO: 102) |
| 103 (S19)-R$^9$ | 93 | 87 | — | FTILEEYFMYRGLLGLRIRRRRRRRRR (SEQ ID NO: 103) |
| 104 (S20)-R$^9$ | 74 | 60 | — | TILEEYFMYRGLLGLRIRRRRRRRRR (SEQ ID NO: 104) |
| 105 (S21)-R$^9$ | 62 | 52 | — | ILEEYFMYRGLLGLRIRRRRRRRRR (SEQ ID NO: 105) |
| 106 (S22)-R$^9$ | 70 | 53 | — | LEEYFMYGLLGLRIRRRRRRRRR (SEQ ID NO: 106) |

Example 3

Effect of Peptides on of CpG-ODN-Induced Cytokine Secretion

Inhibition of TNF-α secretion by various T-peptides was examined. RAW264.7 cells were plated at 3×10⁵ cells/well in 48-well plates. After 24 h the cells were incubated with peptide at various concentrations at room temperature in triplicate for 15 minutes and then stimulated with 1.25 ug/ml CpG-ODN or 1 ng/ml LPS. Cells were then incubated for 4 hours at 37° C., supernatants collected, and TNF-α measured by ELISA. Percent inhibition was calculated by comparing TNF-α secretion from cells incubated with peptide to control cells with no peptide treatment. The inhibition by peptides T3, T11, T21, T36, T37, T51 and T52 were compared to inhibition by an analogue of P13 having a sequence of nine arginine residues (SEQ ID NO: 379) at the C-terminus (P13-R$^9$; SEQ ID NO: 378). (Table 4).

TABLE 4

Percent Inhibition of TNF-α secretion by T peptides. Percent inhibition was calculated by comparing TNF-α secretion from cells incubated with peptide to control cells with no peptide treatment.

| Peptide | 22 µM | 11.1 µM | 7.1 µM | Sequence |
|---|---|---|---|---|
| CpG stimulation | | | | |
| P13-R$^9$ | 86 | 65 | 32 | DIVKLTVYDCIRRRRRRRR (SEQ ID NO: 378) |
| T3-R$^9$ | 99 | 92 | 85 | AIVKLTVYDCIRRRRRRRR (SEQ ID NO: 133) |
| T21-R$^9$ | 98 | 90 | 69 | DIVKLYVYDCIRRRRRRRR (SEQ ID NO: 151) |
| T36-R$^9$ | 82 | 70 | 50 | DIIKLTVYDCIRRRRRRRR (SEQ ID NO: 166) |
| T37-R$^9$ | 93 | 87 | 46 | DIVKVTVYDCIRRRRRRRR (SEQ ID NO: 167) |
| T51-R$^9$ | 99.7 | 98 | 94 | AIVKLTVYACIRRRRRRRR (SEQ ID NO: 181) |
| T52-R$^9$ | 100 | 99.2 | 97.8 | AIIKVYVYACIRRRRRRRR (SEQ ID NO: 182) |

| Peptide | 22.2 uM | 11.1 uM | 7.4 uM | Sequence |
|---|---|---|---|---|
| LPS Stimulation | | | | |
| P13-R$^9$ | 69 | 13 | 0 | DIVKLTVYDCIRRRRRRRR (SEQ ID NO: 378) |
| T3-R$^9$ | 77 | 65 | 33 | AIVKLTVYDCIRRRRRRRR (SEQ ID NO: 133) |
| T11-R$^9$ | 91 | 81 | 68 | DIVKLTVYACIRRRRRRRR (SEQ ID NO: 141) |

Example 4

Structure-Activity Testing of Peptides Derived from P13

Structure-activity relationships (SAR) were investigated to determine tolerances to residue modification in P13. Peptides used in the SAR include SEQ ID NOS: 131-182, used to study the activities of SEQ ID NOS: 317-368. Peptides possessing the following structural modifications were made and evaluated for activity vis-à-vis P13:
1. Deletions of N- and/or C-terminal residues;
2. Alanine scan at each residue;
3. Comparison of residues with like charges at the same position (for example, Asp or Glu at the same position; Lys, Arg, or His at the same position);
4. Comparison of hydroxylated side chains at the same position (for example, Ser or Thr at the same position);
5. Comparison of aromatic side chains at the same position (for example, Phe, Tyr, His, or Trp at the same position);
6. Replacement of side chains with sulfur-containing side chains (for example, Met and Cys);
7. Conservative replacement of branched aliphatic side chains (for example, Leu, Ile, and Val);
8. Disruption of structure by inclusion of alternate residues;
9. Reverse and scrambled sequence; and
10. Dimerization.

The SAR revealed that certain substitutions led to peptides with activity superior to that of P13. The substitution of a single amino acid, in at least five different cases, and the substitution of two or more amino acids in at least two cases, resulted in superior activity. These seven peptides are SEQ ID NOS: 133, 141, 151, 166, 167, 181, and 182. The discovery was unexpected in that the activity of the SAR derivatives was expected to be comparable or lesser than that of P13. Activity was defined as inhibition of TNF-α after stimulation of RAW264.7 cells with CpG.

Example 5

Effect of Peptides on Otitis Media

Induction of otitis media: BALB/c (Bagg albino) mice, about 8-12 weeks of age, are anesthetized with a subcutaneous injection of xylazine & ketamine (about 0.1 mg/30 gm body weight) and their ears examined under the operating microscope to assure they are free of infection or perforation. One group of animals is injected with PBS (Phospho-buffered saline) in one ear and with about 10 µM of a peptide of Table 1 in the opposite ear, to determine the effect of peptide without added bacteria. A second group of animals receive about 5.0 µl of PBS plus heat-inactivated S. pneumoniae (about 10⁹ CFU/ml) in one ear and about 5.0 µl of peptide (about 10 µM) plus heat-inactivated S. pneumoniae (about 10⁹ CFU/ml) in the opposite ear. Injections are done through the tympanic membrane. Animals are killed about 3 days after bacterial injection and tissue is histologically processed to assess middle ear disease. Inflammation is quantified by measuring 1) area of fluid present in the middle ear; 2) number of cells in middle ear fluid; and 3) thickness of the tympanic membrane (TM) taken at a point away from the injection site. Data are obtained from mice (n=18) injected with PBS alone for each of the histological parameters measured, to serve as a control group. Disease induction is defined as positive if the ear injected with S. pneumoniae without peptide demonstrated an increase of at least two standard deviations above the control PBS treated mice in at least two of the three parameters assessed for middle ear inflammation: Fluid area, cell number, thickness of the tympanic membrane.

Tissue Collection:

At the end of the experimental treatment, mice are killed and tissues collected for histology. Mice are overdosed on anesthetic and perfused intracardially with about 1.0 ml of saline, followed by about 20 ml of fixative (about 1.5% paraformaldehyde, about 3% glutaraldehyde in about 0.1 M phosphate buffer). The middle ears are left intact and connected to each other by the skull base so both ears are processed together for histology and sectioning. This enables all histologic embedding, sectioning, staining, and analysis to be done on the two sides simultaneously to reduce any impact of processing variables on the subsequent quantitative analyses. Middle ears are decalcified, embedded in glycol methacrylate plastic, sectioned at about 5 um, mounted serially on glass slides, stained, and coverslipped.

Histopathologic Analysis:

Three consecutive sections at the level of the umbo and promontory are selected for measures of 1) area of fluid present in the middle ear; 2) number of cells in middle ear fluid; and 3) thickness of the tympanic membrane. Each measurement is taken on the three sequential sections per specimen.

Statistical Analyses:

To determine the effect of peptide without added bacteria, animals are injected in one ear with PBS alone, and the other ear with about 10 µM peptide. Paired t-tests are done comparing the effect of PBS alone with the effect of peptide for each of the three histological parameters: 1) area of fluid present in the middle ear; 2) number of cells in middle ear fluid; and 3) thickness of the tympanic membrane. Paired t-tests are done using these animals comparing the effect of peptide plus *S. pneumoniae* in one ear with *S. pneumoniae* alone in the opposite ear for each of the histological parameters described above.

Example 6

Effect of Peptides on Septic Shock

Inhibition of Inflammatory Mediators in a Murine Septic Shock Model.

BALB/c mice are injected i.p. with PBS, LPS at about 100 µg/mouse/250 µl, or about 100 µg LPS plus various doses of peptides. Serum is collected at about 2 and about 6 hours after treatment and evaluated for the pro-inflammatory cytokines MIP-2 and TNF-α by ELISA, and for soluble ICAM-1.

Example 7

Effects of P13 on Mouse Middle Ear

Assay of Effects Caused by Peptide without Added Bacteria.

Five mice were injected in one ear with PBS and in the opposite ear with 10 µM peptide P13. Three days later the animals were killed, and the middle ears embedded, sectioned, stained and evaluated for fluid area, infiltrating cell number, and thickness of the tympanic membrane. Paired t-tests (2-tailed) were used to analyze each of the three parameters. In the absence of bacterial-induced inflammation, no differences were seen between the PBS-injected ear and P13-injected ear in 1) fluid area (p=0.104); 2) cell number (p=0.880); or 3) tympanic membrane thickness (p=0.891).

Assay of Effects Caused by Peptide with Added Bacteria.

To examine the effectiveness of the peptide to affect inflammation in vivo, twenty BALB/c mice were injected in the middle ear on one side with heat-inactivated *S. pneumoniae* plus PBS, and in the middle ear on the opposite side with heat-inactivated *S. pneumoniae* plus 10 µM peptide P13. Three days later the animals were killed, and evaluated for middle ear fluid area, infiltrating cell number, and thickness of the tympanic membrane. Disease development was defined as an increase over background controls (PBS injected ears n=18) of at least two standard deviations in two out of the three parameters quantified. A total of 7 out of 20 mice met the criteria for disease induction. Analysis of middle ears by paired t-tests from these 7 mice with disease showed that peptide treatment significantly reduced the amount of fluid (p=0.004), infiltrating cell number (p=0.02), and thickness of the tympanic membrane (p=0.002). Examination of these three parameters of inflammation for each individual mouse with disease illustrated the dramatic effect seen with a single treatment of peptide P13. Of interest, 6 of the 7 mice demonstrated reductions in all areas of inflammation, while one animal showed only modest reduction in fluid area and tympanic membrane thickness, and no reduction in cell number. Injection of heat-killed bacteria resulted in a marked inflammatory response in the middle ear after 3 days. This was characterized by mucosal and tympanic membrane swelling, cellular infiltration, and significant fluid (effusion) secretion and accumulation that filled the middle ear space. The inflammatory response led to significant mucosal cellular hypertrophy and active secretion of mucins and other fluids. When peptide P13 was injected with the bacteria, a significant reduction was seen in fluid accumulation into the middle ear space and reduced mucosal hypertrophy.

TABLE 5

Peptide Inhibition of Middle Ear Inflammation[a]

| Treatment | Fluid Area (microns$^2$ ± S.D.) | Cell Number (±S.D.) | Tympanic Membrane Thickness (microns ± S.D.) |
|---|---|---|---|
| PBS[b] | 1016 ± 1397 | 31 ± 41 | 44 ± 20 |
| S. pneumoniae[c] | 5771 ± 2077 | 252 ± 140 | 105 ± 33 |
| S. pneumoniae + peptide[c] | 1486 ± 1192 | 111 ± 119 | 44 ± 15 |
| p value (2-tailed)[d] | p = 0.004 | p = 0.020 | p = 0.002 |

[a]Middle ear inflammation is assessed by measuring three consecutive tissue sections for area of fluid in the middle ear, number of cells in the middle ear fluid, and thickness of the tympanic membrane measured at a point away from the injection site. Data represent the mean ± SD animals with middle ear inflammation. Statistical evaluation is done using a paired t-test.
[b]The PBS treated animals receive no bacteria or peptides.
[c]Animals are injected in one ear with S. pneumoniae + PBS and in the opposite ear with S. pneumoniae + peptide (about 10 µM).
[d]Statistical evaluation using a paired t-test is done using data collected from diseased animals injected with bacteria and comparing peptide vs. no peptide treatment.

Example 8

Assay for Crossing the Tympanic Membrane by FITC-labeled P13-R$^9$ (SEQ ID NO: 378)

BALB/c mice were injected through the bulla by the following protocol.

Three BALB/c mice at 8-12 weeks of age were anesthetized with ketamine (100 mg/kg) and xylazine (20 mg/kg) prior to administration of bacteria. A ventral midline incision was made in the neck, and the bulla exposed after blunt dissection. The middle ear was inoculated through the bony wall with approximately 3.5 µl of a bacterial suspension (heat inactivated *S. pneumoniae* 10$^{10}$ CFU/ml) with a thin needle. Both the right and left ears received bacteria by bulla injection.

After 24 hours, animals received an otoscopic exam using an operating microscope. Mice were anesthetized as described above, and the tympanic membrane was inspected for the presence or absence of the following three criteria for acute otitis media (AOM): 1) middle ear effusion behind the tympanic membrane; 2) change in color of the tympanic membrane from clear to red or white (indicating inflammation and/or purulence in the middle ear); 3) change in position of the tympanic membrane from neutral to bulging or retracted. Only animals demonstrating AOM by these criteria were used.

Four ears met the criteria for AOM. FITC labeled peptide P13-R$^9$ (SEQ ID NO: 378) (10 μg/30 μl) was dropped onto the middle ear. The peptide was allowed to absorb for 10 minutes. After 10 minutes, the external ear canal was flushed twice, and blotted to get rid of any remaining peptide. The middle ear fluid was then aspirated with a 10 μl Hamilton syringe with a 30 g needle, and the fluid smeared on a slide. FITC-labeled peptide was viewed under a fluorescent scope. The photograph demonstrates that FITC-labeled P13-R$^9$ (SEQ ID NO: 378) crosses the tympanic membrane and associates with cells in middle ear fluid.

FIG. 1 illustrates bright field microscopy of cells in middle ear fluid (Panel A). FIG. 1 illustrates fluorescent microscopy of FITC-labeled P13-R$^9$ (SEQ ID NO: 378) associated with cells in middle ear fluid (Panel B).

Example 9

Figure 2:
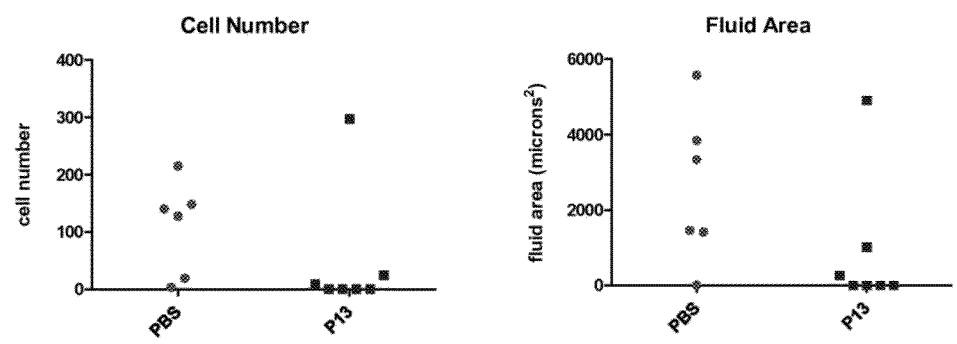
FIG. 2: P13 reduces middle ear inflammation. BALB/c mice (n=6 in PBS group and n=7 in P13 group) were injected with heat-killed S. pneumonia, treated 24 hours later with topical (ear drop) administration of P13 (1 µg), and histology was examined 72 hours after bacteria introduction. Panel A: cell number within middle ear; Panel B: fluid area within middle ear. Note: Animal with high cell number and high fluid area in the P13 treated group is the same animal.

Topical Administration of P13 Reduced Middle Ear Inflammation and Fluid Retention In this experiment, P13 was administered by ear drops to reduce inflammation and fluid retention in the pre-clinical AOM model. BALB/c mice (n=13) received an otoscopic exam using an operating microscope to establish the clinical symptoms of AOM. Mice were anesthetized and the tympanic membrane (TM) inspected for presence or absence of the following 3 criteria for AOM: 1) middle ear effusion behind the TM; 2) change in color of the TM from clear to red or white, indicating inflammation and/or purulence in the middle ear; and 3) change in position of the TM from neutral to bulging or retracted. An animal exhibiting any of these changes was scored positive for inflammation. All mice scored negative on pre-screen and were injected transtympanically with 5 μl heat inactivated S. pneumonia ($10^9$ CFU/ml) in both ears. Twenty-four hours post bacterial injection, mice were examined by otoscopic exam and those animals meeting the inflammation criteria described above remained in the study. Of the thirteen ears scored as positive; seven ears were treated topically with P13 (1 μg/30 μl), and six ears treated topically with PBS (30 μl). For topical treatment, animals were lightly anesthetized and P13 or PBS was dropped onto the external tympanic membrane. The animals remained sedated for 15-20 minutes. Seventy-two hours post bacterial injection, animals were sacrificed and tissue histologically processed to assess middle ear disease. Inflammation was quantified by measuring the area of fluid present in the middle ear and number of cells in the measured middle ear fluid area as follows. Mice were overdosed on anesthetic and perfused intracardially with 1.0 ml of saline, followed by 20 ml of fixative (1.5% paraformaldehyde-3% glutaraldehyde in 0.1 M phosphate buffer). Middle ears were decalcified, embedded in glycol methacrylate plastic, sectioned at 5 μm, mounted serially on glass slides stained, and cover-slipped. Three consecutive sections at the level of the umbo and promontory were selected for measures of 1) area of fluid present in the middle ear; and 2) number of cells in middle ear fluid. Each measurement was taken on the three sequential sections per specimen. The value presented for each parameter represents the mean of the three sections (FIG. 2). This experiment confirmed that ear drop administration of P13 dramatically reduced both the cellular infiltration and residual fluid in the pre-clinical AOM model. Of interest, the one animal in the P13 treatment group showing high cell number and high fluid area is the same animal.

Example 10

Topical Administration of P13 Significantly Reduced the Severity and Longevity of Hearing Impairment A. Topical Administration of P13 Demonstrated Efficacy in a Mouse Model of AOM.

Patients with AOM frequently experience residual middle ear fluid retention which can lead to impaired hearing, recurrent infections, and in extreme conditions the need for surgical placement of ear tubes. To determine whether topical administration of P13 would impact hearing in a pre-clinical model of AOM, BALB/c mice (n=8), 13 weeks of age, received a baseline auditory brainstem response (ABR) and otoscopic exam in both ears. ABR stimuli consisted of 20 tone-burst trains at 4 kHz, 8 kHz, 16 kHz and 32 kHz at five intensity levels in 10 dB steps. Each tone-burst had a two-ms duration, with tone burst onsets separated by 12 ms. Two separate trains offset by 5 dB were presented as stimuli, then combined in data analysis to determine threshold in 5 dB steps. Responses to 300 stimulus repetitions were averaged using a digital oscilloscope. Thresholds were based on the lowest intensity at which a response could be identified. The number of waves present at threshold varied somewhat, but the presence of at least two waves was considered a valid threshold. An otoscopic exam was performed using an operating microscope to establish the clinical symptoms of AOM, as previously described. All 8 animals remained in the study and were injected transtympanically with 5 μl heat inactivated S. pneumonia ($10^9$ CFU/ml) in both ears. Twenty-four hours post bacterial injection, mice were examined by otoscopic exam and those animals meeting the inflammation criteria remained in this study. After 24 hours, each animal was treated topically with P13 (1 μg/30 μl) in one ear, and PBS (30 ul) in the other. For topical treatment, animals were lightly anesthetized and P13 or PBS dropped onto the external tympanic membrane. The animals remained sedated for 15-20 minutes.

Figure 3:
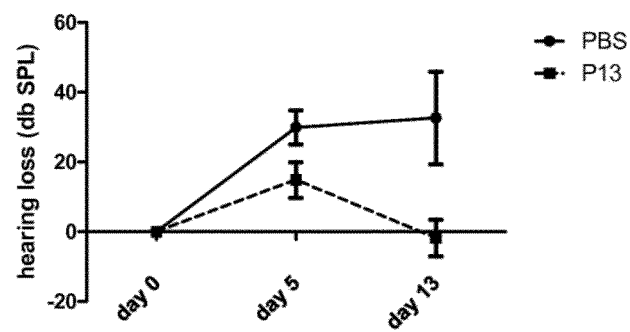
FIG. 3: Topical administration of P13 significantly improves hearing thresholds. BALB/c mice were administered heat-killed S. pneumonia, 24 hours later mice were treated topically (ear drops) with P13 (1 µg) or PBS. Panel A: Hearing thresholds at 4, 8, 16 and 32 kHz were quantified by ABR at days 5 and 13 days after administration of bacteria. Hearing loss was calculated by subtracting the background ABR from post-treatment ABR and summing across frequencies. Panel B: Number of animals with >20 DB hearing loss across all frequencies. Number of animals is in parentheses.
Figure 4:
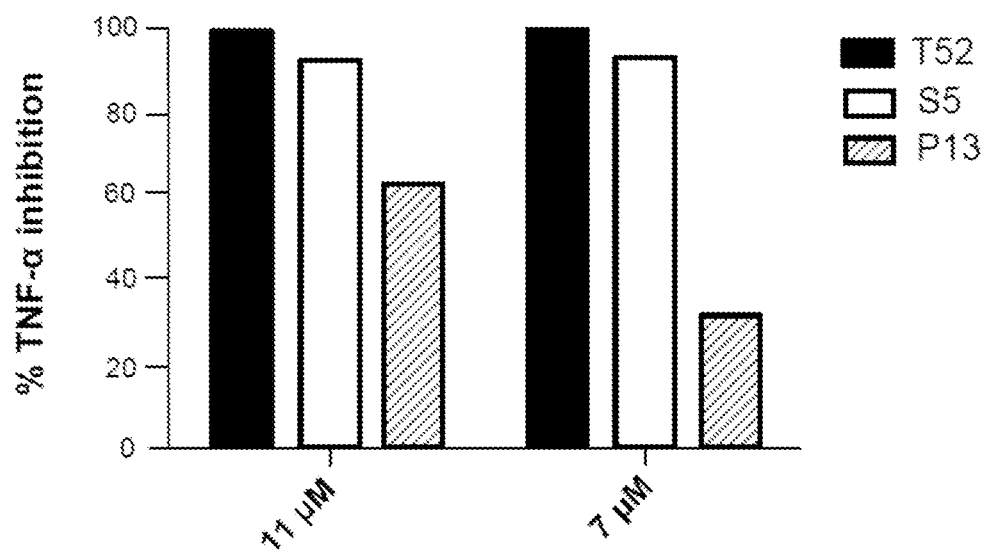
FIG. 4: Percent Inhibition of TNF-α secretion by peptides T52, S5 and P13. RAW264.7 cells were plated at $3\times10^5$ cells/well in 48-well plates. After 24 h the cells were incubated with peptide at various concentrations at room temperature in triplicate for 15 minutes and then stimulated with 1 µg/ml CpG-ODN. Cells were then incubated for 4 hours at 37° C., supernatants collected, and TNF-α measured by ELISA. Percent inhibition was calculated by comparing TNF-α secretion from cells incubated with peptide to control cells with no peptide treatment.

Five and 13 days after bacterial injection, all animals received ABR testing as described above. ABR data was calculated by subtracting the baseline ABR from the post-bacterial ABR for each frequency, and then summing all 4 frequencies (4, 8, 16 and 32 kHz). A two-way repeated measure ANOVA was done for data analysis using days 5 and 13. This experiment confirmed that ear drop administration of P13 significantly limited the hearing impairment seen in control treated animals. Treatment with P13 reduced the severity of hearing impairment and reduced the time to resolution to normal baseline hearing levels (FIG. 3A). P13 treatment dramatically reduced the number of animals with hearing loss as compared to PBS treatment (FIG. 3B). In summary, these data confirmed the efficacy of P13 in reducing the severity and longevity of hearing impairment.

B. Topical Administration of P13 Demonstrated Efficacy in a Mouse Model of Chronic Otitis Media.

Eight C3H/HeJ mice (12 months of age) were given a clinical ear examination. Those animals demonstrating middle ear inflammation (6 mice) were given two baseline ABRs, one week apart, and then each ear was treated topically with either PBS, or 1 μg P13. One and two weeks after P13/PBS treatment, animals again received an otoscopic exam and an ABR assessment. ABR data were calculated by subtracting the baseline ABR from the post-treatment ABR for each frequency, and then summing all 4 frequencies. Topical P13 treatment resulted in a statistically significant improvement in hearing thresholds as assessed by ABR measurements across all four frequencies at both weeks 1 and 2 post-treatment. This data showed a dramatic improvement in hearing thresholds at both time-points, with an approximate 40 db improvement at week 2. An examination of a single frequency (4 kHz) demonstrated the impact of P13 treatment on hearing, where at week 2 post-treatment, there was an approximate 12 db hearing improvement in P13 treated animals as compared to controls. No change was observed in the middle ear inflammatory status as assessed by otoscopic exam after peptide treatment at either time point.

C. Comparison of the D- and L-Isomer Forms of P13 in Treating COM

The biological half-life of peptides can be improved by using the D-isomer of amino acid residues in place of the L-isomer form. A stereoisomer of P13 containing all D-amino acid residues (D-P13) was therefore tested for efficacy in treating C3H/HeJ mice with COM, and the results were compared to those obtained with the stereoisomer containing all L-amino acid residues (L-P13). The D-P13 peptide was produced by standard methods and was purified to >95%. Three C3H/HeJ mice with COM were treated topically with D-P13 in both ears as described above and ABRs assessed at weeks 1 and 2 post-treatment. Similar to what was seen with L-P 13 treatment, treatment with D-P 13 also demonstrated efficacy in improving hearing thresholds in COM mice with clinically documented disease. At week 2 post-treatment, D-P13 improved hearing thresholds across all frequencies approximately 20 db as compared to an approximate 40 db improvement after treatment with L-P13. While the L-isomer of P13 showed a more pronounced improvement of hearing thresholds, the D- and L-isomer forms of P13 exhibited similar levels of statistical confidence in this experiment.

Example 11

Topical Administration of P13 Lacked Ototoxicity

P13 was investigated for possible negative impact on hearing in normal mice upon administration by ear drops. BALB/c mice, 16 weeks of age, (n=16) received two baseline auditory brainstem response (ABR) tests one week apart, and an otoscopic exam in both ears. ABR stimuli consisted of 20 tone-burst trains at 4 kHz, 8 kHz, 16 kHz and 32 kHz at five intensity levels in 10 dB steps, as previously described. An otoscopic exam was performed using an operating microscope to establish the clinical symptoms of AOM, as previously described. Any animal with an abnormal ABR or exam on pre-screen was not entered into the study.

All 16 animals remained in the study and were divided into five groups as follows:
  group 1: (n=6 ears) 1 µg P13/30 µl, topically, given once;
  group 2: (n=7 ears) 10 µg P13/30 µl, topically, given once;
  group 3: (n=7 ears) 10 µg P13/30 µl, topically, given twice, 24 hours apart;
  group 4: (n=6 ears) 60 µg P13/30 µl, topically, given once; and
  group 5: (n=6 ears) untreated mice.

ABRs were performed at one, two, three and four weeks post P13 treatment. The two baseline ABRs were averaged and compared to the ABRs post P13 treatment. This experiment demonstrated that topical administration of P13 did not negatively impact hearing thresholds in these normal mice.

Example 12

Evaluation of TNF-α Secretion in Mice Treated with Peptides

The effect of several peptides on TNF-α secretion in mice in response to stimulation by CpG-ODN and LPS is studied. Peptide compositions are prepared for each peptide-$R^9$ (SEQ ID NO: 379), at 3 concentrations, 37 µM, 22.2 µM, and 11.1 µM, and tested. Peptides demonstrating activity in this assay are further formulated into peptide compositions at 11.1 µM, 7.4 µM, and 3.7 µM for re-assay.

BALB/c (Bagg albino) mice, about 8-12 weeks of age, are anesthetized with a subcutaneous injection of xylazine & ketamine (about 0.1 mg/30 gm body weight). The mice are injected in both ears with either 1.25 ug/ml CpG-ODN or 1 ng/ml LPS. Twenty-four hours later the mice are treated topically (ear drop) with 1 µg peptide/30 µl in one ear and PBS (30 µl) in the other. Twenty-four hours post peptide/PBS treatment, middle ear fluid is collected and analyzed for TNF-α secretion by ELISA. Ears exhibiting lesser TNF-α secretion than the control ears identify peptides that effectively inhibit TNF-α secretion in the live mouse.

EMBODIMENTS

The following embodiments provide non-limiting examples of objects of the invention.

In some embodiments, the invention contemplates a pharmaceutical composition comprising a peptide comprising:
  a) a sequence of any one of SEQ ID NOS: 187-368; or
  b) a derivative of P13 comprising at least one D-amino acid residue.

In some embodiments, the pharmaceutical composition of claim 1, wherein the peptide further comprises a transducing sequence at the C-terminus.

In some embodiments, the transducing sequence is a polyarginine sequence.

In some embodiments, the transducing sequence comprises nine consecutive arginine residues (SEQ ID NO: 379).

In some embodiments, the transducing sequence consists of nine consecutive arginine residues (SEQ ID NO: 379).

In some embodiments, the peptide comprises a derivative of P13 comprising at least one D-amino acid residue.

In some embodiments, the amino acid residues of the peptide are D-amino acid residues.

In some embodiments, the amino acid residues that are not part of the transducing sequence are D-amino acid residues.

In some embodiments, at least one amino acid residue of the transducing sequence is a D-amino acid residue.

In some embodiments, all the amino acid residues of the transducing sequence are D-amino acid residues.

In some embodiments, the peptide is any one of SEQ ID NOS: 42-44, 68-77, 79-81, 83, 102-106, 133, 141, 151, 166, 167, 181, and 182.

In some embodiments, the peptide is any one of SEQ ID NOS: 228-230, 254-263, 265-267, 269, 288-292, 319, 327, 337, 352, 353, 367, and 368.

In some embodiments, the pharmaceutical composition further comprises a pharmaceutically acceptable excipient.

In some embodiments, the pharmaceutical composition is in the form of a drop.

In some embodiments, the pharmaceutical composition is in the form of an aerosol, vapor, spray, or mist.

In some embodiments, the invention contemplates a pharmaceutical composition comprising a peptide comprising a sequence of any one of SEQ ID NOS: 1-186.

In some embodiments, the invention contemplates a peptide comprising the sequence of any one of SEQ ID NOS: 1-368.

In some embodiments, the peptide comprises the sequence of any one of SEQ ID NOS: 42-44, 68-77, 79-81, 83, 102-106, 133, 141, 151, 166, 167, 181, 182, 228-230, 254-263, 265-267, 269, 288-292, 319, 327, 337, 352, 353, 367, and 368.

In some embodiments, the invention contemplates a derivative of a peptide comprising the sequence of any one of SEQ ID NOS: 1-369, wherein the derivative comprises at least one D-amino acid residue.

In some embodiments, the invention contemplates a method of regulating cellular activity, the method comprising administering to an organism in need or want thereof an effective amount of a pharmaceutical composition comprising a peptide comprising:
 a) a sequence of any one of SEQ ID NOS: 187-368; or
 b) a derivative of P13 comprising at least one D-amino acid residue, wherein the peptide optionally further comprises a transducing sequence at the C-terminus.

In some embodiments, the cellular activity is mediated by a toll-like receptor.

In some embodiments, the cellular activity mediated by a toll-like receptor is TNF-α secretion.

In some embodiments, the method provides 10%, 20%, 30%, 40%, 50%, 60%, 70%, 80% or 90% inhibition of TNF-α secretion following stimulation by LPS and/or CpG-ODN.

In some embodiments, the administering results in an inhibition of cytokine secretion.

In some embodiments, the invention contemplates a method of treating inflammation in an animal, the method comprising administering to an animal in need or want thereof a pharmaceutical composition comprising a peptide comprising:
 a) a sequence of any one of SEQ ID NOS: 187-368; or
 b) a derivative of P13 comprising at least one D-amino acid residue, wherein the peptide optionally further comprises a transducing sequence at the C-terminus.

In some embodiments, the inflammation is caused by a virus, bacteria, fungi, antigen, self-antigen, or a combination thereof.

In some embodiments, the inflammation is ear inflammation.

In some embodiments, the inflammation is otitis media.

In some embodiments, the administration reduces or eliminates a symptom of otitis media.

In some embodiments, the symptom is pain, otorrhea, fever, irritability, anorexia, vomiting or diarrhea.

In some embodiments, the symptom is pain.

In some embodiments, the inflammation is inflammation of the skin, joints, muscular tissue, brain, or connective tissue.

In some embodiments, the inflammation is arthritis, dermatitis, Lupus erythematosus, meningitis, or psoriasis.

In some embodiments, the arthritis is osteoarthritis, rheumatoid arthritis, septic arthritis, gout, pseudo-gout, juvenile idiopathic arthritis, Still's disease, or ankylosing spondylitis.

In some embodiments, the dermatitis is spongiotic dermatitis, childhood eczema, allergic contact dermatitis, seborrhoeic dermatitis, dyshidrotic dermatitis, urticaria, vesicular or bullous dermatitis, or papular urticaria.

In some embodiments, the psoriasis is plaque psoriasis, flexural psoriasis, guttate psoriasis, pustular psoriasis, nail psoriasis, psoriatic arthritis, or erythrodermic psoriasis.

In some embodiments, the pharmaceutical composition is administered via topical application.

In some embodiments, the topical application comprises application to the skin, hair, outer ear, tympanic membrane, buccal cavity, nasal cavity, or sublingual cavity.

In some embodiments, the topical application comprises application to the tympanic membrane.

In some embodiments, the application to the tympanic membrane comprises the application of drops to the tympanic membrane.

In some embodiments, the animal is a human.

In some embodiments, the invention contemplates a method of treating sinusitis, the method comprising administering an aerosol composition to an organism in need or want thereof, the aerosol composition comprising a therapeutically-effective amount of a peptide comprising:
 a) a sequence of any one of SEQ ID NOS: 187-369; or
 b) a derivative of P13 comprising at least one D-amino acid residue, wherein the peptide optionally further comprises a transducing sequence at the C-terminus.

In some embodiments, the invention contemplates a method of improving hearing in an animal, the method comprising administering to an animal having middle and/or inner ear inflammation and reduced hearing a therapeutically-effective amount of a peptide comprising:
 a) a sequence of any one of SEQ ID NOS: 187-369; or
 b) a derivative of P13 comprising at least one D-amino acid residue, wherein the peptide optionally further comprises a transducing sequence at the C-terminus, wherein the peptide is administered topically, wherein the hearing improves to a level no better than ordinary levels, and/or the hearing improves faster than the hearing would improve without administration of the peptide.

In some embodiments, the invention contemplates a method of treating middle and/or inner ear inflammation, the method comprising administering to a tympanic membrane of an animal in need or want thereof a therapeutically-effective amount of a peptide comprising:
 a) a sequence of any one of SEQ ID NOS: 187-369; or
 b) a derivative of P13 comprising at least one D-amino acid residue, wherein the peptide optionally further comprises a transducing sequence at the C-terminus.

In some embodiments, the invention contemplates a use of a peptide in the manufacture of a medicament for regulating cellular activity, the peptide comprising:
 a) a sequence of any one of SEQ ID NOS: 187-368; or
 b) a derivative of P13 comprising at least one D-amino acid residue, wherein the peptide optionally further comprises a transducing sequence at the C-terminus.

In some embodiments, the cellular activity is mediated by a toll-like receptor.

In some embodiments, the cellular activity mediated by a toll-like receptor is TNF-α secretion.

In some embodiments, the medicament provides 10%, 20%, 30%, 40%, 50%, 60%, 70%, 80% or 90% inhibition of TNF-α secretion following stimulation by LPS and/or CpG-ODN.

In some embodiments, the medicament is suitable to inhibit cytokine secretion.

In some embodiments, the invention contemplates a use of a peptide in the manufacture of a medicament for treating inflammation in an animal, the peptide comprising:
 a) a sequence of any one of SEQ ID NOS: 187-368; or
 b) a derivative of P13 comprising at least one D-amino acid residue, wherein the peptide optionally further comprises a transducing sequence at the C-terminus.

In some embodiments, the inflammation is caused by a virus, bacteria, fungi, antigen, self-antigen, or a combination thereof.

In some embodiments, the inflammation is ear inflammation.

In some embodiments, the inflammation is otitis media.

In some embodiments, the administration reduces or eliminates a symptom of otitis media.

In some embodiments, the symptom is pain, otorrhea, fever, irritability, anorexia, vomiting or diarrhea.

In some embodiments, the symptom is pain.

In some embodiments, the inflammation is inflammation of the skin, joints, muscular tissue, brain, or connective tissue.

In some embodiments, the inflammation is arthritis, dermatitis, Lupus erythematosus, meningitis, or psoriasis.

In some embodiments, the arthritis is osteoarthritis, rheumatoid arthritis, septic arthritis, gout, pseudo-gout, juvenile idiopathic arthritis, Still's disease, or ankylosing spondylitis.

In some embodiments, the dermatitis is spongiotic dermatitis, childhood eczema, allergic contact dermatitis, seborrhoeic dermatitis, dyshidrotic dermatitis, urticaria, vesicular or bullous dermatitis, or papular urticaria.

In some embodiments, the psoriasis is plaque psoriasis, flexural psoriasis, guttate psoriasis, pustular psoriasis, nail psoriasis, psoriatic arthritis, or erythrodermic psoriasis.

In some embodiments, the medicament is suitable for topical application.

In some embodiments, the topical application comprises application to the skin, hair, outer ear, tympanic membrane, buccal cavity, nasal cavity, or sublingual cavity.

In some embodiments, the topical application comprises application to the tympanic membrane.

In some embodiments, the application to the tympanic membrane comprises the application of drops to the tympanic membrane.

In some embodiments, the animal is a human.

In some embodiments, the invention contemplates a use of a peptide in the manufacture of a medicament for treating sinusitis, the medicament comprising an aerosol composition, the peptide comprising:
a) a sequence of any one of SEQ ID NOS: 187-369; or
b) a derivative of P13 comprising at least one D-amino acid residue, wherein the peptide optionally further comprises a transducing sequence at the C-terminus.

In some embodiments, the invention contemplates a use of a peptide in the manufacture of a medicament for improving hearing in an animal, wherein the animal has middle and/or inner ear inflammation and reduced hearing, the peptide comprising:
a) a sequence of any one of SEQ ID NOS: 187-369; or
b) a derivative of P13 comprising at least one D-amino acid residue, wherein the peptide optionally further comprises a transducing sequence at the C-terminus, wherein the medicament is a topical medicament.

In some embodiments, the invention contemplates a use of a peptide in the manufacture of a medicament for treating middle and/or inner ear inflammation, wherein the medicament is suitable for administration to a tympanic membrane of an animal in need or want thereof, the peptide comprising:
a) a sequence of any one of SEQ ID NOS: 187-369; or
b) a derivative of P13 comprising at least one D-amino acid residue, wherein the peptide optionally further comprises a transducing sequence at the C-terminus.

Embodiment 101. A composition comprising a peptide comprising the amino acid sequence FTILEEYFMY (SEQ ID NO: 371).

Embodiment 102. The composition of embodiment 101, wherein the peptide is selected from the group consisting of S1-S17.

Embodiment 103. The composition of embodiment 101, wherein peptide further comprises a transducing sequence.

Embodiment 104. The composition of embodiment 103, wherein the transducing sequence comprises a 9-arginine sequence positioned at the C-terminus.

Embodiment 105. A method of regulating cellular activity comprising administering a peptide to a cell, said peptide comprising the amino acid sequence FTILEEYFMY (SEQ ID NO: 371).

Embodiment 106. The method of embodiment 105, wherein the peptide is selected from the group consisting of S1-S17.

Embodiment 107. The method of embodiment 105, wherein the peptide further comprises a transducing sequence.

Embodiment 108. The method of embodiment 106, wherein the transducing sequence comprises a 9-arginine sequence positioned at the C-terminus.

Embodiment 109. The method of embodiment 105, wherein the activity is mediated by toll-like receptor.

Embodiment 110. The method of embodiment 105, wherein the administration results in an inhibition of cytokine secretion.

Embodiment 111. The method of embodiment 106, wherein the peptide is used in the treatment of inflammation.

Embodiment 112. The method of embodiment 111, wherein the inflammation is caused by a virus, bacteria, fungi, antigen, self-antigen, or a combination thereof.

Embodiment 113. The method of embodiment 105, wherein the administration of said peptide to said cell results in a 10%, 20%, 30%, 40%, 50%, 60%, 70%, 80% or 90% inhibition of TNF-α secretion following stimulation by CpG-ODN.

Embodiment 114. A method of decreasing TNF-α secretion in response to toll-like receptor signaling comprising administering a therapeutically effective dose of a peptide derived from A52R.

Embodiment 115. A pharmaceutical composition comprising:
a peptide comprising the amino acid sequence set forth in any one of the peptides selected from S1-S17;
a 9-arginine sequence (SEQ ID NO: 379) positioned at the C-terminus of the said peptide; and
a pharmaceutically-acceptable excipient,
wherein said composition is used for the treatment inflammation.

Embodiment 201. A composition comprising a peptide comprising the amino acid sequence LEEYFMY (SEQ ID NO: 370).

Embodiment 202. The composition of embodiment 201, wherein the peptide is selected from the group consisting of S1-S22.

Embodiment 203. The composition of embodiments 201 or 202, wherein peptide further comprises a transducing sequence.

Embodiment 204. The composition of embodiment 203, wherein the transducing sequence comprises a 9-arginine sequence (SEQ ID NO: 379) positioned at the C-terminus.

Embodiment 205. The composition of embodiments 201 or 202, wherein the peptide comprises a L-isomer amino acid or a D-isomer amino acid or L- and D-isomer amino acids.

Embodiment 206. The composition of embodiment 203, wherein the peptide and/or the transducing sequence comprises a L-isomer amino acid or a D-isomer amino acid or L- and D-isomer amino acids.

Embodiment 207. A method of regulating cellular activity comprising administering a peptide to a cell, said peptide comprising the amino acid sequence LEEYFMY (SEQ ID NO: 370).

Embodiment 208. The method of embodiment 207, wherein the peptide is selected from the group consisting of S1-S22.

Embodiment 209. The method of embodiments 207 or 208, wherein the peptide further comprises a transducing sequence.

Embodiment 210. The method of embodiment 209, wherein the transducing sequence comprises a 9-arginine sequence (SEQ ID NO: 379) positioned at the C-terminus.

Embodiment 211. The method of embodiments 207 or 208, wherein the peptide comprises a L-isomer amino acid or a D-isomer amino acid or L- and D-isomer amino acids.

Embodiment 212. The method of embodiment 209, wherein the peptide and/or the transducing sequence comprises a L-isomer amino acid or a D-isomer amino acid or L- and D-isomer amino acids.

Embodiment 213. The method of embodiment 207, wherein the activity is mediated by toll-like receptor.

Embodiment 214. The method of embodiment 207, wherein the administration results in an inhibition of cytokine secretion.

Embodiment 215. The method of embodiment 208, wherein the peptide is used in the treatment of inflammation.

Embodiment 216. The method of embodiment 215, wherein the inflammation is caused by a virus, bacteria, fungi, antigen, self-antigen, or a combination thereof.

Embodiment 217. The method of embodiment 207, wherein the administration of said peptide to said cell results in a 10%, 20%, 30%, 40%, 50%, 60%, 70%, 80% or 90% inhibition of TNF-α secretion following stimulation by CpG-ODN.

Embodiment 218. A method of decreasing TNF-α secretion in response to toll-like receptor signaling comprising administering a therapeutically effective dose of a peptide derived from A52R.

Embodiment 219. A pharmaceutical composition comprising: (a) a peptide comprising the amino acid sequence set forth in any one of the peptides selected from S1-S22; (b) a 9-arginine sequence (SEQ ID NO: 379) positioned at the C-terminus of the said peptide; and a pharmaceutically-acceptable excipient, wherein said composition is used for the treatment inflammation.

Embodiment 301. A composition comprising a peptide comprising the amino acid sequence VYDCI (SEQ ID NO: 372), VYACI (SEQ ID NO: 373), KLTVY (SEQ ID NO: 374), KLYVY (SEQ ID NO: 375), or KVYVY (SEQ ID NO: 376).

Embodiment 302. The composition of embodiment 301, wherein the peptide is selected from the group consisting of the peptides presented in Table 1.

Embodiment 303. The composition of embodiment 301, wherein peptide further comprises a transducing sequence.

Embodiment 304. The composition of embodiment 303, wherein the transducing sequence comprises a 9-arginine sequence (SEQ ID NO: 379) positioned at the C-terminus.

Embodiment 305. A method of regulating cellular activity comprising administering a peptide to a cell, said peptide comprising the amino acid sequence VYDCI (SEQ ID NO: 372), VYACI (SEQ ID NO: 373), KLTVY (SEQ ID NO: 374), KLYVY (SEQ ID NO: 375), or KVYVY (SEQ ID NO: 376).

Embodiment 306. The method of embodiment 305, wherein the peptide is selected from the group consisting of the peptides presented in Table 1.

Embodiment 307. The method of embodiment 305, wherein the peptide further comprises a transducing sequence.

Embodiment 308. The method of embodiment 306, wherein the transducing sequence comprises a 9-arginine sequence (SEQ ID NO: 379) positioned at the C-terminus.

Embodiment 309. The method of embodiment 305, wherein the activity is mediated by toll-like receptor.

Embodiment 310. The method of embodiment 305, wherein the administration results in an inhibition of cytokine secretion.

Embodiment 311. The method of embodiment 306, wherein the peptide is used in the treatment of inflammation.

Embodiment 312. The method of embodiment 311, wherein the inflammation is caused by a virus, bacteria, fungi, antigen, self-antigen, or a combination thereof.

Embodiment 313. The method of embodiment 305, wherein the administration of said peptide to said cell results in a 10%, 20%, 30%, 40%, 50%, 60%, 70%, 80% or 90% inhibition of TNF-α secretion following stimulation by CpG-ODN.

Embodiment 314. The method of embodiment 305, wherein the administration of said peptide to said cell results in a 10%, 20%, 30%, 40%, 50%, 60%, 70%, 80% or 90% inhibition of TNF-α secretion following stimulation by LPS.

Embodiment 315. A method of decreasing TNF-α secretion in response to toll-like receptor signaling comprising administering a therapeutically effective dose of a peptide derived from P13.

Embodiment 316. A pharmaceutical composition comprising:
a peptide comprising the amino acid sequence set forth in any one of the peptides selected from the peptides listed in Table 1;
a 9-arginine sequence positioned at the C-terminus of the said peptide; and
a pharmaceutically-acceptable excipient,
wherein said composition is used for the treatment inflammation.

Embodiment 401. A composition comprising a peptide comprising the amino acid sequence VYACI (SEQ ID NO: 373), KLYVY (SEQ ID NO: 375), or KVYVY (SEQ ID NO: 376).

Embodiment 402. The composition of embodiment 401, wherein the peptide is selected from the group consisting of the peptides presented in Table 1.

Embodiment 403. The composition of embodiments 401 or 402, wherein the peptide further comprises a transducing sequence.

Embodiment 404. The composition of embodiment 403, wherein the transducing sequence comprises a 9-arginine sequence (SEQ ID NO: 379) positioned at the C-terminus.

Embodiment 405. The composition of embodiments 401 or 402, wherein the peptide comprises a L-isomer amino acid or a D-isomer amino acid or L- and D-isomer amino acids.

Embodiment 406. The composition of embodiment 403, wherein the peptide and/or the transducing sequence comprises a L-isomer amino acid or a D-isomer amino acid or L- and D-isomer amino acids.

Embodiment 407. A method of regulating cellular activity comprising administering a peptide to a cell, said peptide comprising the amino acid sequence VYACI (SEQ ID NO: 373), KLYVY (SEQ ID NO: 375), or KVYVY (SEQ ID NO: 376).

Embodiment 408. The method of embodiment 407, wherein the peptide is selected from the group consisting of the peptides presented in Table 1.

Embodiment 409. The method of embodiments 407 or 408, wherein the peptide further comprises a transducing sequence.

Embodiment 410. The method of embodiment 409, wherein the transducing sequence comprises a 9-arginine sequence (SEQ ID NO: 379) positioned at the C-terminus.

Embodiment 411. The method of embodiments 407 or 408, wherein the peptide comprises a L-isomer amino acid or a D-isomer amino acid or L- and D-isomer amino acids.

Embodiment 412. The method of embodiment 409, wherein the peptide and/or the transducing sequence comprises a L-isomer amino acid or a D-isomer amino acid or L- and D-isomer amino acids.

Embodiment 413. The method of embodiment 407, wherein the activity is mediated by toll-like receptor.

Embodiment 414. The method of embodiment 407, wherein the administration results in an inhibition of cytokine secretion.

Embodiment 415. The method of embodiment 408, wherein the peptide is used in the treatment of inflammation.

Embodiment 416. The method of embodiment 415, wherein the inflammation is caused by a virus, bacteria, fungi, antigen, self-antigen, or a combination thereof.

Embodiment 417. The method of embodiment 407, wherein the administration of said peptide to said cell results in a 10%, 20%, 30%, 40%, 50%, 60%, 70%, 80% or 90% inhibition of TNF-α secretion following stimulation by CpG-ODN.

Embodiment 418. The method of embodiment 407, wherein the administration of said peptide to said cell results in a 10%, 20%, 30%, 40%, 50%, 60%, 70%, 80% or 90% inhibition of TNF-α secretion following stimulation by LPS.

Embodiment 419. A method of decreasing TNF-α secretion in response to toll-like receptor signaling comprising administering a therapeutically effective dose of a peptide derived from P13.

Embodiment 420. A pharmaceutical composition comprising:
a peptide comprising the amino acid sequence set forth in any one of the peptides selected from the peptides listed in Table 1;
a 9-arginine sequence (SEQ ID NO: 379) positioned at the C-terminus of the said peptide; and
a pharmaceutically-acceptable excipient,
wherein said composition is used for the treatment inflammation.

Embodiment 501. A pharmaceutical composition comprising:
a peptide comprising the amino acid sequence set forth in any one of the peptides selected from P13, a P13 variant, derivative, stereoisomer, or analogue, or a peptide of Table 1;
a 9-arginine sequence (SEQ ID NO: 379) positioned at the C-terminus of the said peptide; and
a pharmaceutically-acceptable excipient,
wherein said composition is used for the treatment of inflammation.

Embodiment 502. The pharmaceutical composition of embodiment 501, wherein the inflammation comprises otitis media.

Embodiment 503. The pharmaceutical composition of embodiment 502, further comprising wherein the pharmaceutical composition is applied via topical application.

Embodiment 504. The pharmaceutical composition of embodiment 503, wherein the topical application comprises application to the skin, hair, outer ear, tympanic membrane, buccal cavity, or sublingual cavity.

Embodiment 505. The pharmaceutical composition of embodiment 504, wherein the topical application comprises application to the tympanic membrane.

Embodiment 506. The pharmaceutical composition of embodiment 505, wherein the application to the tympanic membrane comprises the application of ear drops to the tympanic membrane.

Embodiment 507. A pharmaceutical composition effective to:
decrease the amount of middle ear fluid by about 30-80 percent;
decrease an infiltrating cell number in middle ear fluid by about 30-80 percent; and
decrease the thickness of a tympanic membrane by about 30-80 percent in a mouse comprising inflammation of the ear, wherein the composition is administered to the mouse in an amount of about 0.01 ug to 60 ug.

Embodiment 508. The pharmaceutical composition of embodiment 507, comprising a peptide.

Embodiment 509. The pharmaceutical composition of embodiment 508, wherein the peptide comprises P13 or a variant, derivative, stereoisomer, or analogue thereof.

Embodiment 510. The pharmaceutical composition of embodiment 509, wherein the peptide comprises P13, a peptide comprising P13 and a poly-argenine domain, or a peptide of Table 1.

Embodiment 511. The pharmaceutical composition of embodiment 509, wherein the peptide comprises P13.

Embodiment 512. The pharmaceutical composition of embodiment 509, wherein the peptide comprises a stereoisomer of P13, wherein one or more amino acid residues of the stereoisomer comprise the D-configuration.

Embodiment 513. The pharmaceutical composition of embodiment 512, wherein the peptide comprises a stereoisomer of P13 wherein all the amino acid residues of the stereoisomer comprise the D-configuration.

Embodiment 514. The pharmaceutical composition of embodiment 507, wherein the inflammation comprises otitis media.

Embodiment 515. The pharmaceutical composition of embodiment 514, comprising a peptide.

Embodiment 516. The pharmaceutical composition of embodiment 515, wherein the peptide comprises P13 or a variant, derivative, stereoisomer, or analogue thereof.

Embodiment 517. The pharmaceutical composition of embodiment 516, wherein the peptide comprises P13, a peptide comprising P13 and a poly-argenine domain, or a peptide of Table 1.

Embodiment 518. The pharmaceutical composition of embodiment 516, wherein the peptide comprises P13.

Embodiment 519. The pharmaceutical composition of embodiment 516, wherein the peptide comprises a stereoisomer of P13, wherein one or more amino acid residues of the stereoisomer comprise the D-configuration.

Embodiment 520. The pharmaceutical composition of embodiment 519, wherein the peptide comprises a stereoisomer of P13 wherein all the amino acid residues of the stereoisomer comprise the D-configuration.

Embodiment 521. The pharmaceutical composition of embodiment 514, further comprising wherein the pharmaceutical composition is applied via topical application.

Embodiment 522. The pharmaceutical composition of embodiment 521, comprising a peptide.

Embodiment 523. The pharmaceutical composition of embodiment 522, wherein the peptide comprises P13 or a variant, derivative, stereoisomer, or analogue thereof.

Embodiment 524. The pharmaceutical composition of embodiment 523, wherein the peptide comprises P13, a peptide comprising P13 and a poly-argenine domain, or a peptide of Table 1.

Embodiment 525. The pharmaceutical composition of embodiment 523, wherein the peptide comprises P13.

Embodiment 526. The pharmaceutical composition of embodiment 523, wherein the peptide comprises a stereoisomer of P13, wherein one or more amino acid residues of the stereoisomer comprise the D-configuration.

Embodiment 527. The pharmaceutical composition of embodiment 526, wherein the peptide comprises a stereoisomer of P13 wherein all the amino acid residues of the stereoisomer comprise the D-configuration.

Embodiment 528. The pharmaceutical composition of embodiment 521, wherein the topical application comprises application to the skin, hair, outer ear, tympanic membrane, buccal cavity, or sublingual cavity.

Embodiment 529. The pharmaceutical composition of embodiment 528, comprising a peptide.

Embodiment 530. The pharmaceutical composition of embodiment 529, wherein the peptide comprises P13 or a variant, derivative, stereoisomer, or analogue thereof.

Embodiment 531. The pharmaceutical composition of embodiment 530, wherein the peptide comprises P13, a peptide comprising P13 and a poly-argenine domain, or a peptide of Table 1.

Embodiment 532. The pharmaceutical composition of embodiment 530, wherein the peptide comprises P13.

Embodiment 533. The pharmaceutical composition of embodiment 530, wherein the peptide comprises a stereoisomer of P13, wherein one or more amino acid residues of the stereoisomer comprise the D-configuration.

Embodiment 534. The pharmaceutical composition of embodiment 533, wherein the peptide comprises a stereoisomer of P13 wherein all the amino acid residues of the stereoisomer comprise the D-configuration.

Embodiment 535. The pharmaceutical composition of embodiment 528, wherein the topical application comprises application to the tympanic membrane.

Embodiment 536. The pharmaceutical composition of embodiment 535, comprising a peptide.

Embodiment 537. The pharmaceutical composition of embodiment 536, wherein the peptide comprises P13 or a variant, derivative, stereoisomer, or analogue thereof.

Embodiment 538. The pharmaceutical composition of embodiment 537, wherein the peptide comprises P13, a peptide comprising P13 and a poly-argenine domain, or a peptide of Table 1.

Embodiment 539. The pharmaceutical composition of embodiment 537, wherein the peptide comprises P13.

Embodiment 540. The pharmaceutical composition of embodiment 537, wherein the peptide comprises a stereoisomer of P13, wherein one or more amino acid residues of the stereoisomer comprise the D-configuration.

Embodiment 541. The pharmaceutical composition of embodiment 540, wherein the peptide comprises a stereoisomer of P13 wherein all the amino acid residues of the stereoisomer comprise the D-configuration.

Embodiment 542. The pharmaceutical composition of embodiment 535, wherein the application to the tympanic membrane comprises the application of ear drops to the tympanic membrane.

Embodiment 543. The pharmaceutical composition of embodiment 542, comprising a peptide.

Embodiment 544. The pharmaceutical composition of embodiment 543, wherein the peptide comprises P13 or a variant, derivative, stereoisomer, or analogue thereof.

Embodiment 545. The pharmaceutical composition of embodiment 544, wherein the peptide comprises P13, a peptide comprising P13 and a poly-argenine domain, or a peptide of Table 1.

Embodiment 546. The pharmaceutical composition of embodiment 544, wherein the peptide comprises P13.

Embodiment 547. The pharmaceutical composition of embodiment 544, wherein the peptide comprises a stereoisomer of P13, wherein one or more amino acid residues of the stereoisomer comprise the D-configuration.

Embodiment 548. The pharmaceutical composition of embodiment 547, wherein the peptide comprises a stereoisomer of P13 wherein all the amino acid residues of the stereoisomer comprise the D-configuration.

Embodiment 549. A method of treating ear inflammation in an animal in need or want thereof, the method comprising administering to the animal the pharmaceutical composition of embodiment 507.

Embodiment 550. The method of embodiment 549, wherein the ear inflammation comprises otitis media.

Embodiment 551. The method of embodiment 550, further comprising wherein the pharmaceutical composition is applied via topical application.

Embodiment 552. The method of embodiment 551, wherein the topical application comprises application to the skin, hair, outer ear, tympanic membrane, buccal cavity, or sublingual cavity.

Embodiment 553. The method of embodiment 552, wherein the topical application comprises application to the tympanic membrane.

Embodiment 554. The method of embodiment 553, wherein the application to the tympanic membrane comprises the application of ear drops to the tympanic membrane.

Embodiment 555. The method of embodiment 549, 550, 551, 552, 553, or 554, wherein the pharmaceutical composition comprises P13, a P13 variant, derivative, stereoisomer, or analogue, or a peptide of Table 1.

Embodiment 556. The method of embodiment 555, wherein the P13 variant, derivative, stereoisomer, or analogue comprises P13 and a poly-argenine domain.

Embodiment 557. The method of embodiment 555, wherein the pharmaceutical composition comprises P13.

Embodiment 558. The pharmaceutical composition of embodiment 555, wherein the peptide comprises a stereoisomer of P13, wherein one or more amino acid residues of the stereoisomer comprise the D-configuration.

Embodiment 559. The method of embodiment 558, wherein the peptide comprises a stereoisomer of P13 wherein all the amino acid residues of the stereoisomer comprise the D-configuration.

Embodiment 560. A method of treating ear inflammation in an animal, the method comprising administering a peptide to the animal, wherein the peptide comprises P13, a P13 variant, derivative, stereoisomer, or analogue, or a peptide of Table 1.

Embodiment 561. The method of embodiment 560, wherein the ear inflammation comprises otitis media.

Embodiment 562. The method of embodiment 561, wherein the administering of the peptide comprises application to the skin, hair, outer ear, tympanic membrane, buccal cavity, or sublingual cavity.

Embodiment 563. The method of embodiment 562, wherein the topical application comprises application to the tympanic membrane, optionally via ear drops.

Embodiment 564. The method of embodiment 563, wherein the peptide comprises P13.

Embodiment 565. The method of embodiment 564, wherein the animal is human.

Embodiment 566. The method of embodiment 563, wherein the peptide comprises P13 and a poly-argenine domain.

Embodiment 567. The method of embodiment 566, wherein the animal is human.

Embodiment 568. The method of embodiment 563, wherein the peptide comprises DIVKLTVYDCIR-RRRRRRRR (SEQ ID NO: 378).

Embodiment 569. The method of embodiment 568, wherein the animal is human.

Embodiment 570. The method of embodiment 563, wherein the peptide comprises a stereoisomer of P13, wherein one or more amino acid residues of the stereoisomer comprise the D-configuration.

Embodiment 571. The method of embodiment 570, wherein the peptide comprises a stereoisomer of P13 wherein all the amino acid residues of the stereoisomer comprise the D-configuration.

Embodiment 572. The method of embodiment 571, wherein the animal is human.

Embodiment 573. The method of embodiment 563, wherein the peptide comprises an analogue of P13, wherein one or more amino acid residues of the analogue comprise the D-configuration.

Embodiment 574. The method of embodiment 573, wherein the peptide comprises an analogue of P13, wherein all the amino acid residues of the analogue corresponding to a residue of P13 comprise the D-configuration, and a poly-argenine domain.

Embodiment 575. The method of embodiment 574, wherein the animal is human.

Embodiment 576. The method of embodiment 563, wherein the peptide comprises: D-Asp-D-Ile-D-Val-D-Lys-D-Leu-D-Thr-D-Val-D-Tyr-D-Asp-D-Cys-D-Ile-Arg-Arg-Arg-Arg-Arg-Arg-Arg-Arg-Arg (SEQ ID NO: 183).

Embodiment 577. The method of embodiment 576, wherein the animal is human.

Embodiment 578. The method of embodiment 573, wherein the peptide comprises an analogue of P13, wherein all the amino acid residues of the analogue corresponding to a residue of P13 comprise the D-configuration, and a poly-argenine domain comprising at least one amino acid residue of the D-configuration.

Embodiment 579. The method of embodiment 578, wherein the animal is human.

Embodiment 580. The method of embodiment 563, wherein the peptide comprises: D-Asp-D-Ile-D-Val-D-Lys-D-Leu-D-Thr-D-Val-D-Tyr-D-Asp-D-Cys-D-Ile-D-Arg-D-Arg-D-Arg-D-Arg-D-Arg-D-Arg-D-Arg-D-Arg-D-Arg (SEQ ID NO: 184).

Embodiment 581. The method of embodiment 580, wherein the animal is human.

Embodiment 582. A peptide comprising the amino acid sequence: D-Asp-D-Ile-D-Val-D-Lys-D-Leu-D-Thr-D-Val-D-Tyr-D-Asp-D-Cys-D-Ile-Arg-Arg-Arg-Arg-Arg-Arg-Arg-Arg-Arg (SEQ ID NO: 183).

Embodiment 583. A peptide comprising the amino acid sequence: D-Asp-D-Ile-D-Val-D-Lys-D-Leu-D-Thr-D-Val-D-Tyr-D-Asp-D-Cys-D-Ile-D-Arg-D-Arg-D-Arg-D-Arg-D-Arg-D-Arg-D-Arg-D-Arg-D-Arg (SEQ ID NO: 184).

Embodiment 584. A peptide comprising the amino acid sequence: D-Asp-D-Ile-D-Val-D-Lys-D-Leu-D-Thr-D-Val-D-Tyr-D-Asp-D-Cys-D-Ile (SEQ ID NO: 185).

Embodiment 585. A peptide comprising the amino acid sequence: Asp-Ile-Val-Lys-Leu-Thr-Val-Tyr-Asp-Cys-Ile-D-Arg-D-Arg-D-Arg-D-Arg-D-Arg-D-Arg-D-Arg-D-Arg-D-Arg (SEQ ID NO: 186).

Embodiment 586. A pharmaceutical composition comprising a peptide, the peptide comprising:
P13 or a variant, derivative, stereoisomer, or analogue thereof; or
a peptide of Table 1,
wherein the composition is used for the treatment of inflammation of the skin, joints, muscular tissue, or connective tissue in a subject.

Embodiment 587. The pharmaceutical composition of embodiment 586, wherein the inflammation comprises arthritis, dermatitis, Lupus erythematosus, or psoriasis.

Embodiment 588. The pharmaceutical composition of embodiment 587, wherein the arthritis comprises osteoarthritis, rheumatoid arthritis, septic arthritis, gout, pseudo-gout, juvenile idiopathic arthritis, Still's disease, or ankylosing spondylitis.

Embodiment 589. The pharmaceutical composition of embodiment 587, wherein the dermatitis comprises spongiotic dermatitis, childhood eczema, allergic contact dermatitis, seborrhoeic dermatitis, dyshidrotic dermatitis, urticaria, vesicular or bullous dermatitis, or papular urticaria.

Embodiment 590. The pharmaceutical composition of embodiment 587, wherein the psoriasis comprises plaque psoriasis, flexural psoriasis, guttate psoriasis, pustular psoriasis, nail psoriasis, psoriatic arthritis, or erythrodermic psoriasis.

Embodiment 591. The pharmaceutical composition of embodiment 586, further comprising one or more pharmaceutically-acceptable excipients.

Embodiment 592. The pharmaceutical composition of embodiment 586, wherein the peptide comprises P13 or a variant, derivative, stereoisomer, or analogue thereof.

Embodiment 593. The pharmaceutical composition of embodiment 592, wherein the peptide comprises P13, or a peptide comprising P13 and a poly-argenine domain.

Embodiment 594. The pharmaceutical composition of embodiment 592, wherein the peptide comprises P13.

Embodiment 595. The pharmaceutical composition of embodiment 592, wherein the peptide comprises a stereoisomer of P13, wherein one or more amino acid residues of the stereoisomer comprise the D-configuration.

Embodiment 596. The pharmaceutical composition of embodiment 595, wherein the peptide comprises a stereoisomer of P13 wherein all the amino acid residues of the stereoisomer comprise the D-configuration.

Embodiment 597. The pharmaceutical composition of embodiment 592, wherein the peptide comprises P13 and a poly-argenine domain.

Embodiment 598. The pharmaceutical composition of embodiment 597, wherein the peptide comprises DIVKLTVYDCIRRRRRRRRR (SEQ ID NO: 378).

Embodiment 599. The pharmaceutical composition of embodiment 592, wherein the peptide comprises an analogue of P13, wherein one or more amino acid residues of the analogue comprise the D-configuration.

Embodiment 600. The pharmaceutical composition of embodiment 599, wherein the peptide comprises an analogue of P13, wherein all the amino acid residues of the analogue corresponding to a residue of P13 comprise the D-configuration, and a poly-argenine domain.

Embodiment 601. The pharmaceutical composition of embodiment 599, wherein the peptide comprises: D-Asp-D-Ile-D-Val-D-Lys-D-Leu-D-Thr-D-Val-D-Tyr-D-Asp-D-Cys-D-Ile-Arg-Arg-Arg-Arg-Arg-Arg-Arg-Arg-Arg (SEQ ID NO: 183).

Embodiment 602. The pharmaceutical composition of embodiment 599, wherein the peptide comprises: D-Asp-D-Ile-D-Val-D-Lys-D-Leu-D-Thr-D-Val-D-Tyr-D-Asp-D-Cys-D-Ile-D-Arg-D-Arg-D-Arg-D-Arg-D-Arg-D-Arg-D-Arg-D-Arg-D-Arg (SEQ ID NO: 184).

Embodiment 603. A method of treating inflammation in an animal, the method comprising administering a peptide to the animal, wherein the peptide comprises P13, a P13 variant, derivative, stereoisomer, or analogue, or a peptide of Table 1.

Embodiment 604. The method of embodiment 603, wherein the inflammation comprises arthritis, dermatitis, Lupus erythematosus, meningitis, or psoriasis.

Embodiment 605. The method of embodiment 604, wherein the arthritis comprises osteoarthritis, rheumatoid arthritis, septic arthritis, gout, pseudo-gout, juvenile idiopathic arthritis, Still's disease, or ankylosing spondylitis.

Embodiment 606. The method of embodiment 604, wherein the dermatitis comprises spongiotic dermatitis, childhood eczema, allergic contact dermatitis, seborrhoeic dermatitis, dyshidrotic dermatitis, urticaria, vesicular or bullous dermatitis, or papular urticaria.

Embodiment 607. The method of embodiment 604, wherein the psoriasis comprises plaque psoriasis, flexural psoriasis, guttate psoriasis, pustular psoriasis, nail psoriasis, psoriatic arthritis, or erythrodermic psoriasis.

Embodiment 608. The method of embodiment 603, wherein the peptide comprises P13 or a variant, derivative, stereoisomer, or analogue thereof.

Embodiment 609. The method of embodiment 608, wherein the peptide comprises P13, or a peptide comprising P13 and a poly-argenine domain.

Embodiment 610. The method of embodiment 608, wherein the peptide comprises P13.

Embodiment 611. The method of embodiment 608, wherein the peptide comprises a stereoisomer of P13, wherein one or more amino acid residues of the stereoisomer comprise the D-configuration.

Embodiment 612. The method of embodiment 611, wherein the peptide comprises a stereoisomer of P13 wherein all the amino acid residues of the stereoisomer comprise the D-configuration.

Embodiment 613. The method of embodiment 608, wherein the peptide comprises P13 and a poly-argenine domain.

Embodiment 614. The method of embodiment 613, wherein the peptide comprises DIVKLTVYDCIR-RRRRRRRR (SEQ ID NO: 378).

Embodiment 615. The method of embodiment 608, wherein the peptide comprises an analogue of P13, wherein one or more amino acid residues of the analogue comprise the D-configuration.

Embodiment 616. The method of embodiment 615, wherein the peptide comprises an analogue of P13, wherein all the amino acid residues of the analogue corresponding to a residue of P13 comprise the D-configuration, and a poly-argenine domain.

Embodiment 617. The method of embodiment 615, wherein the peptide comprises: D-Asp-D-Ile-D-Val-D-Lys-D-Leu-D-Thr-D-Val-D-Tyr-D-Asp-D-Cys-D-Ile-Arg-Arg-Arg-Arg-Arg-Arg-Arg-Arg-Arg (SEQ ID NO: 183).

Embodiment 618. The method of embodiment 615, wherein the peptide comprises: D-Asp-D-Ile-D-Val-D-Lys-D-Leu-D-Thr-D-Val-D-Tyr-D-Asp-D-Cys-D-Ile-D-Arg-D-Arg-D-Arg-D-Arg-D-Arg-D-Arg-D-Arg-D-Arg-D-Arg (SEQ ID NO: 184).

Embodiment 619. The method of any of embodiments 603-618, wherein the animal is a human.

Embodiment 6120. The method of any of embodiments 603-618, wherein the administering comprises topical application.

REFERENCES

The following references, and those cited in the disclosure herein, are hereby incorporated herein in their entirety by reference.

1. Takeda, K., and S. Akira 2004. TLR signaling pathways. Seminars in Immunology 16:3.
2. Schnare M., G. M. Barton, A. C. Holt, K. Takeda, S. Akira, and R. Medzhitov. 2001. Toll-like receptor control activation of adaptive immune responses. Nat. Immuno. 2:947.
3. Granucci, F., C. Vizzardelli, N. Pavelka, S. Feau, M. Persico, E. Virzi, M. Rescigno, G. Moro, and P. Ricciardi-Castagnoli. 2001. Inducible 11-2 production by dendritic cells revealed by global gene expression analysis. Nat. Immunol. 2:882.
4. Krieg, A. M. 2002. CpG motifs in bacterial DNA and their immune effects. Ann. Rev. Immunol. 20:709.
5. Trinchieri, G. 1998. Interleukin-12: a cytokine at the interface of inflammation and immunity. Adv. Immunol. 70:83.
6. Ozato, K., H. Tsujimura, and T Tamura. 2002. Toll-like receptor signaling and regulation of cytokine gene expression in the immune system. BioTechniques Oct Suppl: 66.
7. Yi, A. K., J. G. Yoon, S. J. Yeo, S.C. Hong, B. K. English, and A. M. Krieg. 2002. Role of mitogen-activated protein kinases in CpG DNA-mediated IL-10 and IL-12 production: central role of extracellular signal-regulated kinase in the negative feedback loop of the CpG DNA-mediated Th1 response. J. Immunol. 168:4711.
8. Fan, J. and A. B. Malik. 2003. Toll-like receptor-4(TLR4) signaling augments chemokine-induced neutrophil migration by modulating cell surface expression of chemokine receptors. Nat. Med. 9:315.
9. McCoy, S. L., S. E. Kurtz, F. A. Hausman, S. R. Trune, R. M. Bennett, and S. H. Hefeneider. 2004. Activation of RAW264.7 macrophages by bacterial DNA and lipopolysaccharide increases cell surface DNA binding and internalization. J. Biol. Chem. 279:17217.
10. Hoshino, K., O. Takeuchi, T. Kawai, H. Sanjo, T. Ogawa, Y. Takeda, K. Takeda, and S. Akira 1999. Cutting Edge: Toll-like receptor 4 (TLR4)-deficient mice are hyporesponsive to lipopolysaccharide: evidence for TLR4 as the Lps gene product. J. Immunol. 162:3749.
11. Hemmi, H., O. Takeuchi, T. Kawai, T. Kaisho, S. Sato, H. Sanjo, M. Matsumo, K. Hoshino, H. Wagner, K. Takeda, and S. Akira 2000. A Toll-like receptor recognizes bacterial DNA. Nature 408:740.
12. Hayashi, F., K. D. Smith, A. Ozinsky, T. R. Hawn, E. C. Yi, D. R. Goodlett, J. K. Eng, S. Akira, D, M. Underhill, and A. Aderem. 2001. The innate immune response to bacterial flagellin is mediated by Toll-like receptor 5. Nature 410:1099.
13. Takeda, K., T. Kaisho, and S. Akira 2003. Toll-like receptors. Ann. Rev. Immunol. 21:335.
14. Akira, S. 2003. Mammalian Toll-like receptors. Curr. Opin. Immunol. 15:5.
15. Bowie, A., E. Kiss-Toth, J. A. Symons, G. L. Smith, S. K. Dower, and L. A. J. O'Neill. 2000. A46R and A52R from vaccinia virus are antagonists of host IL-1 and toll-like receptor signaling. Proc. Natl. Acad. Sci. U.S.A. 97:10162.
16. O'Neill L. 2000. The Toll/interleukin-1 receptor domain: a molecular switch for inflammation and host defence. Biochem. Soc. Trans. 28:557.
17. Bellows, C. F., R. F. Garry, and B. M. Jaffe. 2003. Vaccinia virus-induced inhibition of nitric oxide production. J. Surg. Res. 111:127.
18. Harte, M. T., I. R. Haga, G. Maloney, P. Gray, P. C. Reading, N. W. Bartlett, G. L. Smith, A. Bowie, and L. A. J. O'Neill. 2003. The poxvirus protein A52R targets Toll-like receptor signaling complexes to suppress host defense. J. Exp. Med. 197:343.

19. Yi, A. K., and A. M. Krieg. 1998. Cutting Edge: Rapid induction of mitogen-activated protein kinases by immune stimulatory CpG DNA. J. Immunol. 161:4493.
20. Wender, P. A., D. J. Mitchell, K. Pattabiraman, E. T. Pelkey, and L. Steinman. 2000. The design, synthesis, and evaluation of molecules that enable or enhance cellular uptake: Peptoid molecular transporters. Proc. Natl. Acad. Sci. U.S.A. 97:13003.
21. Barzilai A., B. Dekel, R. Dagan, and E. Leibovitz. 2000. Middle ear effusion 11-6 concentration in bacterial and non-bacterial acute otitis media. Acta Paediatr 89:1068.
22. Takeda, K. and S. Akira. 2004. TLR signaling pathways. Semin. Immunol. 16:3.
23. Janssens, S., and R. Beyaert. 2003. Functional diversity and regulation of different interleukin-1 receptor-associated kinase (IRAK) family members. Mol. Cell. 11:293.
24. Daun, J. M., and M. J. Fenton. 2000. Interleukin-1/Toll receptor family members: receptor structure and signal transduction pathways. J. Interferon Cytokine Res. 20:843.
25. Barton, G. M., and R. Medzhitov. 2003 Linking Toll-like receptors to IFN-α/β expression. Nat. Immunol. 4:432.
26. Karasen R. M., Y. Sutbeyaz, B. Aktan, H. Ozdemir, and C. Gundogu. 2000. Effect of web 2170 BS, platelet activating factor receptor inhibitor, in the guinea pig model of middle ear inflammation. Ann 0 to 1 Rhinol Laryngol 109:549.
27. Daly, K. A., L. L. Hunter, and G. S. Giebink. 1999. Chronic Otitis Media with Effusion. Pediatrics in Review 20:85.
28. Kubba H., J. P. Pearson, and J. P. Birchall. 2000. The aetiology of otitis media with effusion: a review. Clin Otolaryngol 25:181.
29. O'Neill, L. A. J. 2003. Therapeutic targeting of Toll-like receptors for inflammatory and infectious diseases. Curr. Opin. Pharm. 3:396.
30. Zuany-Amorim, C., J. Hastewell, and C. Walker. 2002. Toll-like receptors as potential therapeutic targets for multiple diseases. Nat. Rev. Drug Discov. 1:797.
31. Ikezoe, T., Y. Yang, D. Heber, H. Taguchi, and H. P. Koeffler. 2003. PC-SPES: A potent inhibitor of nuclear factor-KB rescues mice from lipopolysaccharide-induced septic shock. Mol. Pharmacol. 64:1521.
32. Delgado, M., C. Abad, C. Martinez, M. G. Juarranz, J. Leceta, D. Ganea, and R. P. Gomariz. 2003. PACAP in immunity and inflammation. Ann. N.Y. Acad. Sci. 992:141.
33. Basu, S., and M. J. Fenton. 2004. Toll-like receptors: function and roles in lung disease. Am. J. Physiol. Lung Cell Mol. Physiol. 286:L887.
34. Kopp, E., and S. Ghosh. 1994. Inhibition of NF-kappa B by sodium salicylate and aspirin. Science 265:956.
35. Almawi, W. Y., and O. K. Melemedjian. 2002. Negative regulation of nuclear factor-kappaB activation and function by glucocorticoids. J. Mol. Endocrinol. 28:69.
36. Andreakos, E. T., B. M. Foxwell, F. M. Brennan, R. N. Maini, and M. Feldmann. 2002. Cytokines and anti-cytokine biologicals in autoimmunity: present and future. Cytokine Growth Factor Rev. 13:299.
37. Meng, G., M. Rutz, M. Schiemann, J. Metzger, A. Grabiec, R. Schwandner, P. B. Luppa, F. Ebel, D. H. Busch, S. Bauer, H. Wagner, and C. J. Kirschning 2004. Antagonistic antibody prevents Toll-like receptor 2-driven lethal shock-like syndromes. J. Clin. Invest. 113:1473.
38. Sweet, M. J., B. P. Leung, D. Kang, M. Sogaard, K. Schulz, V. Trajkovic, C. C. Campbell, D. Xu, and F. Y. Liew. 2001. A novel pathway regulating lipopolysaccharide-induced shock by ST2/T1 via inhibition of Toll-like receptor 4 expression. J. Immunol. 166:6633.
39. Brint, E. K., D. Xu, H. Liu, A. Dunne, A. N. McKenzie, L. A. O'Neill, and F. Y. Liew. 2004. ST2 is an inhibitor of interleukin 1 receptor and Toll-like receptor 4 signaling and maintains endotoxin tolerance. Nat. Immunol. 5:373.
40. Chuang, T. H., and R. J. Ulevitch. 2004. Triad3A, an E3 ubiquitin-protein ligase regulating Toll-like receptors. Nat. Immunol. 5:495.
41. Bartfai, T., M. M. Behrens, S. Gaidarova, J. Pemberton, A. Shivanyuk, and J. Rebek, Jr. 2003. A low molecular weight mimic of the Toll/IL-1 receptor/resistance domain inhibits IL-1 receptor-mediated responses. Proc. Natl. Acad. Sci. U.S.A. 100:7971.
42. McCoy, S. L., Kurtz, S. E., MacArthur, C. J., Trune, D. R, and Hefeneider, S. H.2005. Identification of a Peptide Derived from Vaccinia Virus A52R Protein That Inhibits Cytokine Secretion in Response to TLR-Dependent Signaling and Reduces In Vivo Bacterial-induced Inflammation. Journal of Immunology, 174: 3006-3014.

What is claimed is:

1. A pharmaceutical peptide composition comprising: a peptide, wherein the peptide comprises SEQ ID NO: 337; and a pharmaceutically-acceptable excipient, wherein the pharmaceutical composition is in a unit dosage form.

2. The pharmaceutical peptide composition of claim 1, wherein the peptide is SEQ ID NO: 337.

3. The pharmaceutical peptide composition of claim 1, wherein the pharmaceutical peptide composition is in the form of an ointment, cream, liquid, gel, or salve.

4. The pharmaceutical peptide composition of claim 1, wherein the pharmaceutical peptide composition is in the form of a drop.

5. The pharmaceutical peptide composition of claim 1, wherein the pharmaceutical peptide composition is in the form of an aerosol, vapor, spray, or mist.

6. A synthetic peptide of SEQ ID NO: 337, wherein at least one amino acid residue of the synthetic peptide is in the D-configuration.

7. A synthetic peptide comprising SEQ ID NO: 337.

8. The synthetic peptide of claim 7, wherein the synthetic peptide is SEQ ID NO: 337.

* * * * *

SEQUENCE LISTING

```
<160> NUMBER OF SEQ ID NOS: 379

<210> SEQ ID NO 1
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Tyr Ile Lys Val Gln Lys Gln Asp Ile Val Lys Leu Thr Val Tyr Asp
1               5                   10                  15

Cys Ile Ser Met Ile Gly Leu Cys Ala Arg Arg Arg Arg Arg Arg
                20                  25                  30

Arg Arg

<210> SEQ ID NO 2
<211> LENGTH: 33
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 2

Ile Lys Val Gln Lys Gln Asp Ile Val Lys Leu Thr Val Tyr Asp Cys
1               5                   10                  15

Ile Ser Met Ile Gly Leu Cys Ala Arg Arg Arg Arg Arg Arg Arg
                20                  25                  30

Arg

<210> SEQ ID NO 3
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Lys Val Gln Lys Gln Asp Ile Val Lys Leu Thr Val Tyr Asp Cys Ile
1               5                   10                  15

Ser Met Ile Gly Leu Cys Ala Arg Arg Arg Arg Arg Arg Arg Arg
                20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Val Gln Lys Gln Asp Ile Val Lys Leu Thr Val Tyr Asp Cys Ile Ser
1               5                   10                  15

Met Ile Gly Leu Cys Ala Arg Arg Arg Arg Arg Arg Arg Arg Arg
                20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Lys Gln Asp Ile Val Lys Leu Thr Val Tyr Asp Cys Ile Ser Met
1               5                   10                  15

Ile Gly Leu Cys Ala Arg Arg Arg Arg Arg Arg Arg Arg Arg
                20                  25                  30

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Gln Asp Ile Val Lys Leu Thr Val Tyr Asp Cys Ile Ser Met Ile
1               5                   10                  15

```
Gly Leu Cys Ala Arg Arg Arg Arg Arg Arg Arg Arg
            20                  25

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Asp Ile Val Lys Leu Thr Val Tyr Asp Cys Ile Ser Met Ile Gly
1               5                   10                  15

Leu Cys Ala Arg Arg Arg Arg Arg Arg Arg Arg
            20                  25

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Ile Val Lys Leu Thr Val Tyr Asp Cys Ile Ser Met Ile Gly Leu
1               5                   10                  15

Cys Ala Arg Arg Arg Arg Arg Arg Arg Arg
            20                  25

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Val Lys Leu Thr Val Tyr Asp Cys Ile Ser Met Ile Gly Leu Cys
1               5                   10                  15

Ala Arg Arg Arg Arg Arg Arg Arg Arg
            20                  25

<210> SEQ ID NO 10
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Lys Leu Thr Val Tyr Asp Cys Ile Ser Met Ile Gly Leu Cys Ala
1               5                   10                  15

Arg Arg Arg Arg Arg Arg Arg Arg Arg
            20                  25

<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 11

Lys Leu Thr Val Tyr Asp Cys Ile Ser Met Ile Gly Leu Cys Ala Arg
1               5                   10                  15
Arg Arg Arg Arg Arg Arg Arg
            20

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Thr Val Tyr Asp Cys Ile Ser Met Ile Gly Leu Cys Ala Arg Arg
1               5                   10                  15
Arg Arg Arg Arg Arg Arg Arg
            20

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Val Tyr Asp Cys Ile Ser Met Ile Gly Leu Cys Ala Arg Arg Arg
1               5                   10                  15
Arg Arg Arg Arg Arg Arg
            20

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Tyr Asp Cys Ile Ser Met Ile Gly Leu Cys Ala Arg Arg Arg Arg
1               5                   10                  15
Arg Arg Arg Arg Arg
            20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Asp Cys Ile Ser Met Ile Gly Leu Cys Ala Arg Arg Arg Arg Arg
1               5                   10                  15
Arg Arg Arg Arg
            20

```
<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Cys Ile Ser Met Ile Gly Leu Cys Ala Arg Arg Arg Arg Arg
1               5                   10                  15

Arg Arg Arg

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Ile Ser Met Ile Gly Leu Cys Ala Arg Arg Arg Arg Arg Arg
1               5                   10                  15

Arg Arg

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Ser Met Ile Gly Leu Cys Ala Arg Arg Arg Arg Arg Arg Arg
1               5                   10                  15

Arg

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Met Ile Gly Leu Cys Ala Arg Arg Arg Arg Arg Arg Arg Arg
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Ile Gly Leu Cys Ala Arg Arg Arg Arg Arg Arg Arg Arg
1               5                   10                  15

<210> SEQ ID NO 21
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 21

Ile Gly Leu Cys Ala Arg Arg Arg Arg Arg Arg Arg Arg
1               5                   10

<210> SEQ ID NO 22
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Tyr Ile Lys Val Gln Lys Gln Asp Ile Val Lys Leu Thr Val Tyr Asp
1               5                   10                  15

Cys Ile Ser Met Ile Gly Leu Cys Arg Arg Arg Arg Arg Arg Arg
            20                  25                  30

Arg

<210> SEQ ID NO 23
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Tyr Ile Lys Val Gln Lys Gln Asp Ile Val Lys Leu Thr Val Tyr Asp
1               5                   10                  15

Cys Ile Ser Met Ile Gly Leu Arg Arg Arg Arg Arg Arg Arg Arg
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Tyr Ile Lys Val Gln Lys Gln Asp Ile Val Lys Leu Thr Val Tyr Asp
1               5                   10                  15

Cys Ile Ser Met Ile Gly Arg Arg Arg Arg Arg Arg Arg Arg
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Tyr Ile Lys Val Gln Lys Gln Asp Ile Val Lys Leu Thr Val Tyr Asp
1               5                   10                  15

Cys Ile Ser Met Ile Arg Arg Arg Arg Arg Arg Arg Arg
            20                  25                  30
```

```
<210> SEQ ID NO 26
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Ile Lys Val Gln Lys Gln Asp Ile Val Lys Leu Thr Val Tyr Asp
 1               5                  10                  15

Cys Ile Ser Met Arg Arg Arg Arg Arg Arg Arg Arg Arg
             20                  25

<210> SEQ ID NO 27
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Ile Lys Val Gln Lys Gln Asp Ile Val Lys Leu Thr Val Tyr Asp
 1               5                  10                  15

Cys Ile Ser Arg Arg Arg Arg Arg Arg Arg Arg Arg
             20                  25

<210> SEQ ID NO 28
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Ile Lys Val Gln Lys Gln Asp Ile Val Lys Leu Thr Val Tyr Asp
 1               5                  10                  15

Cys Ile Arg Arg Arg Arg Arg Arg Arg Arg Arg
             20                  25

<210> SEQ ID NO 29
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Ile Lys Val Gln Lys Gln Asp Ile Val Lys Leu Thr Val Tyr Asp
 1               5                  10                  15

Cys Arg Arg Arg Arg Arg Arg Arg Arg Arg
             20                  25

<210> SEQ ID NO 30
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30
```

```
Tyr Ile Lys Val Gln Lys Gln Asp Ile Val Lys Leu Thr Val Tyr Asp
1               5                   10                  15

Arg Arg Arg Arg Arg Arg Arg Arg Arg
            20                  25

<210> SEQ ID NO 31
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Ile Lys Val Gln Lys Gln Asp Ile Val Lys Leu Thr Val Tyr Arg
1               5                   10                  15

Arg Arg Arg Arg Arg Arg Arg Arg
            20

<210> SEQ ID NO 32
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Ile Lys Val Gln Lys Gln Asp Ile Val Lys Leu Thr Val Arg Arg
1               5                   10                  15

Arg Arg Arg Arg Arg Arg Arg
            20

<210> SEQ ID NO 33
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Ile Lys Val Gln Lys Gln Asp Ile Val Lys Leu Thr Arg Arg Arg
1               5                   10                  15

Arg Arg Arg Arg Arg Arg
            20

<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Ile Lys Val Gln Lys Gln Asp Ile Val Lys Leu Arg Arg Arg Arg
1               5                   10                  15

Arg Arg Arg Arg Arg
            20

<210> SEQ ID NO 35
<211> LENGTH: 20
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 35

Tyr Ile Lys Val Gln Lys Gln Asp Ile Val Lys Arg Arg Arg Arg
1               5                   10                  15

Arg Arg Arg Arg
            20

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Ile Lys Val Gln Lys Gln Asp Ile Val Arg Arg Arg Arg Arg
1               5                   10                  15

Arg Arg Arg

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Ile Lys Val Gln Lys Gln Asp Ile Arg Arg Arg Arg Arg Arg
1               5                   10                  15

Arg Arg

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Tyr Ile Lys Val Gln Lys Gln Asp Arg Arg Arg Arg Arg Arg Arg
1               5                   10                  15

Arg

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Ile Lys Val Gln Lys Gln Arg Arg Arg Arg Arg Arg Arg Arg
1               5                   10                  15

<210> SEQ ID NO 40
<211> LENGTH: 15
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 40

Tyr Ile Lys Val Gln Lys Arg Arg Arg Arg Arg Arg Arg Arg Arg Arg
1               5                   10                  15

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Ile Lys Val Gln Arg Arg Arg Arg Arg Arg Arg Arg Arg
1               5                   10

<210> SEQ ID NO 42
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Met Phe Thr Ile Leu Glu Glu Tyr Phe Met Tyr Arg Gly Leu Leu
1               5                   10                  15

Gly Leu Arg Ile Lys Tyr Gly Arg Leu Phe Asn Glu Ile Arg Arg Arg
            20                  25                  30

Arg Arg Arg Arg Arg Arg
        35

<210> SEQ ID NO 43
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Phe Thr Ile Leu Glu Glu Tyr Phe Met Tyr Arg Gly Leu Leu Gly
1               5                   10                  15

Leu Arg Ile Lys Tyr Gly Arg Leu Phe Asn Glu Ile Arg Arg Arg Arg
            20                  25                  30

Arg Arg Arg Arg Arg
        35

<210> SEQ ID NO 44
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Phe Thr Ile Leu Glu Glu Tyr Phe Met Tyr Arg Gly Leu Leu Gly Leu
1               5                   10                  15

Arg Ile Lys Tyr Gly Arg Leu Phe Asn Glu Ile Arg Arg Arg Arg Arg
```

```
                20                  25                  30

Arg Arg Arg Arg
        35

<210> SEQ ID NO 45
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Thr Ile Leu Glu Glu Tyr Phe Met Tyr Arg Gly Leu Leu Gly Leu Arg
1               5                   10                  15

Ile Lys Tyr Gly Arg Leu Phe Asn Glu Ile Arg Arg Arg Arg Arg Arg
                20                  25                  30

Arg Arg Arg
        35

<210> SEQ ID NO 46
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ile Leu Glu Glu Tyr Phe Met Tyr Arg Gly Leu Leu Gly Leu Arg Ile
1               5                   10                  15

Lys Tyr Gly Arg Leu Phe Asn Glu Ile Arg Arg Arg Arg Arg Arg Arg
                20                  25                  30

Arg Arg

<210> SEQ ID NO 47
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Leu Glu Glu Tyr Phe Met Tyr Arg Gly Leu Leu Gly Leu Arg Ile Lys
1               5                   10                  15

Tyr Gly Arg Leu Phe Asn Glu Ile Arg Arg Arg Arg Arg Arg Arg Arg
                20                  25                  30

Arg

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Glu Tyr Phe Met Tyr Arg Gly Leu Leu Gly Leu Arg Ile Lys Tyr
1               5                   10                  15

Gly Arg Leu Phe Asn Glu Ile Arg Arg Arg Arg Arg Arg Arg Arg Arg
                20                  25                  30
```

<210> SEQ ID NO 49
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Tyr Phe Met Tyr Arg Gly Leu Leu Gly Leu Arg Ile Lys Tyr Gly
1               5                   10                  15

Arg Leu Phe Asn Glu Ile Arg Arg Arg Arg Arg Arg Arg Arg Arg
            20                  25                  30

<210> SEQ ID NO 50
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Tyr Phe Met Tyr Arg Gly Leu Leu Gly Leu Arg Ile Lys Tyr Gly Arg
1               5                   10                  15

Leu Phe Asn Glu Ile Arg Arg Arg Arg Arg Arg Arg Arg Arg
            20                  25                  30

<210> SEQ ID NO 51
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Phe Met Tyr Arg Gly Leu Leu Gly Leu Arg Ile Lys Tyr Gly Arg Leu
1               5                   10                  15

Phe Asn Glu Ile Arg Arg Arg Arg Arg Arg Arg Arg Arg
            20                  25

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Met Tyr Arg Gly Leu Leu Gly Leu Arg Ile Lys Tyr Gly Arg Leu Phe
1               5                   10                  15

Asn Glu Ile Arg Arg Arg Arg Arg Arg Arg Arg
            20                  25

<210> SEQ ID NO 53
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Tyr Arg Gly Leu Leu Gly Leu Arg Ile Lys Tyr Gly Arg Leu Phe Asn
1               5                   10                  15

Glu Ile Arg Arg Arg Arg Arg Arg Arg
            20                  25

<210> SEQ ID NO 54
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Gly Leu Leu Gly Leu Arg Ile Lys Tyr Gly Arg Leu Phe Asn Glu
1               5                   10                  15

Ile Arg Arg Arg Arg Arg Arg Arg Arg
            20                  25

<210> SEQ ID NO 55
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Leu Leu Gly Leu Arg Ile Lys Tyr Gly Arg Leu Phe Asn Glu Ile
1               5                   10                  15

Arg Arg Arg Arg Arg Arg Arg Arg Arg
            20                  25

<210> SEQ ID NO 56
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Leu Gly Leu Arg Ile Lys Tyr Gly Arg Leu Phe Asn Glu Ile Arg
1               5                   10                  15

Arg Arg Arg Arg Arg Arg Arg Arg
            20

<210> SEQ ID NO 57
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Gly Leu Arg Ile Lys Tyr Gly Arg Leu Phe Asn Glu Ile Arg Arg
1               5                   10                  15

Arg Arg Arg Arg Arg Arg Arg
            20

<210> SEQ ID NO 58
<211> LENGTH: 22
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 58

Gly Leu Arg Ile Lys Tyr Gly Arg Leu Phe Asn Glu Ile Arg Arg
1               5                   10                  15

Arg Arg Arg Arg Arg Arg
            20

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Leu Arg Ile Lys Tyr Gly Arg Leu Phe Asn Glu Ile Arg Arg Arg
1               5                   10                  15

Arg Arg Arg Arg Arg
            20

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Arg Ile Lys Tyr Gly Arg Leu Phe Asn Glu Ile Arg Arg Arg Arg
1               5                   10                  15

Arg Arg Arg Arg
            20

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Ile Lys Tyr Gly Arg Leu Phe Asn Glu Ile Arg Arg Arg Arg Arg
1               5                   10                  15

Arg Arg Arg

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Lys Tyr Gly Arg Leu Phe Asn Glu Ile Arg Arg Arg Arg Arg Arg
1               5                   10                  15

Arg Arg

```
<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Gly Arg Leu Phe Asn Glu Ile Arg Arg Arg Arg Arg Arg Arg
1               5                   10                  15

Arg

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Arg Leu Phe Asn Glu Ile Arg Arg Arg Arg Arg Arg Arg Arg
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Leu Phe Asn Glu Ile Arg Arg Arg Arg Arg Arg Arg Arg
1               5                   10                  15

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Phe Asn Glu Ile Arg Arg Arg Arg Arg Arg Arg Arg
1               5                   10

<210> SEQ ID NO 67
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Met Phe Thr Ile Leu Glu Glu Tyr Phe Met Tyr Arg Gly Leu Leu
1               5                   10                  15

Gly Leu Arg Ile Lys Tyr Gly Arg Leu Phe Asn Glu Arg Arg Arg
                20                  25                  30

Arg Arg Arg Arg Arg
            35
```

```
<210> SEQ ID NO 68
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Met Phe Thr Ile Leu Glu Glu Tyr Phe Met Tyr Arg Gly Leu Leu
1               5                   10                  15

Gly Leu Arg Ile Lys Tyr Gly Arg Leu Phe Asn Arg Arg Arg Arg Arg
            20                  25                  30

Arg Arg Arg Arg
        35

<210> SEQ ID NO 69
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Met Phe Thr Ile Leu Glu Glu Tyr Phe Met Tyr Arg Gly Leu Leu
1               5                   10                  15

Gly Leu Arg Ile Lys Tyr Gly Arg Leu Phe Arg Arg Arg Arg Arg Arg
            20                  25                  30

Arg Arg Arg
        35

<210> SEQ ID NO 70
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Met Phe Thr Ile Leu Glu Glu Tyr Phe Met Tyr Arg Gly Leu Leu
1               5                   10                  15

Gly Leu Arg Ile Lys Tyr Gly Arg Leu Arg Arg Arg Arg Arg Arg Arg
            20                  25                  30

Arg Arg

<210> SEQ ID NO 71
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Met Phe Thr Ile Leu Glu Glu Tyr Phe Met Tyr Arg Gly Leu Leu
1               5                   10                  15

Gly Leu Arg Ile Lys Tyr Gly Arg Arg Arg Arg Arg Arg Arg Arg Arg
            20                  25                  30

Arg

<210> SEQ ID NO 72
```

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Met Phe Thr Ile Leu Glu Glu Tyr Phe Met Tyr Arg Gly Leu Leu
1               5                   10                  15

Gly Leu Arg Ile Lys Tyr Gly Arg Arg Arg Arg Arg Arg Arg Arg Arg
            20                  25                  30

<210> SEQ ID NO 73
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Met Phe Thr Ile Leu Glu Glu Tyr Phe Met Tyr Arg Gly Leu Leu
1               5                   10                  15

Gly Leu Arg Ile Lys Tyr Arg Arg Arg Arg Arg Arg Arg Arg Arg
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Met Phe Thr Ile Leu Glu Glu Tyr Phe Met Tyr Arg Gly Leu Leu
1               5                   10                  15

Gly Leu Arg Ile Lys Arg Arg Arg Arg Arg Arg Arg Arg Arg
            20                  25                  30

<210> SEQ ID NO 75
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Met Phe Thr Ile Leu Glu Glu Tyr Phe Met Tyr Arg Gly Leu Leu
1               5                   10                  15

Gly Leu Arg Ile Arg Arg Arg Arg Arg Arg Arg Arg Arg
            20                  25

<210> SEQ ID NO 76
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Met Phe Thr Ile Leu Glu Glu Tyr Phe Met Tyr Arg Gly Leu Leu
1               5                   10                  15
```

```
Gly Leu Arg Arg Arg Arg Arg Arg Arg Arg Arg
            20                  25

<210> SEQ ID NO 77
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Met Phe Thr Ile Leu Glu Glu Tyr Phe Met Tyr Arg Gly Leu Leu
1               5                   10                  15

Gly Leu Arg Arg Arg Arg Arg Arg Arg Arg Arg
            20                  25

<210> SEQ ID NO 78
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Glu Met Phe Thr Ile Leu Glu Glu Tyr Phe Met Tyr Arg Gly Leu Leu
1               5                   10                  15

Gly Arg Arg Arg Arg Arg Arg Arg Arg Arg
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Met Phe Thr Ile Leu Glu Glu Tyr Phe Met Tyr Arg Gly Leu Leu
1               5                   10                  15

Arg Arg Arg Arg Arg Arg Arg Arg Arg
            20                  25

<210> SEQ ID NO 80
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Met Phe Thr Ile Leu Glu Glu Tyr Phe Met Tyr Arg Gly Leu Arg
1               5                   10                  15

Arg Arg Arg Arg Arg Arg Arg Arg
            20

<210> SEQ ID NO 81
<211> LENGTH: 23
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 81

Glu Met Phe Thr Ile Leu Glu Glu Tyr Phe Met Tyr Arg Gly Arg Arg
1               5                   10                  15

Arg Arg Arg Arg Arg Arg Arg
            20

<210> SEQ ID NO 82
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Met Phe Thr Ile Leu Glu Glu Tyr Phe Met Tyr Arg Arg Arg Arg
1               5                   10                  15

Arg Arg Arg Arg Arg Arg
            20

<210> SEQ ID NO 83
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Glu Met Phe Thr Ile Leu Glu Glu Tyr Phe Met Tyr Arg Arg Arg Arg
1               5                   10                  15

Arg Arg Arg Arg Arg
            20

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Met Phe Thr Ile Leu Glu Glu Tyr Phe Met Arg Arg Arg Arg Arg
1               5                   10                  15

Arg Arg Arg Arg
            20

<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Glu Met Phe Thr Ile Leu Glu Glu Tyr Phe Arg Arg Arg Arg Arg Arg
1               5                   10                  15

Arg Arg Arg

<210> SEQ ID NO 86

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Glu Met Phe Thr Ile Leu Glu Glu Tyr Arg Arg Arg Arg Arg Arg
1               5                   10                  15

Arg Arg

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Glu Met Phe Thr Ile Leu Glu Glu Arg Arg Arg Arg Arg Arg Arg
1               5                   10                  15

Arg

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Glu Met Phe Thr Ile Leu Glu Arg Arg Arg Arg Arg Arg Arg Arg
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Glu Met Phe Thr Ile Leu Arg Arg Arg Arg Arg Arg Arg Arg
1               5                   10                  15

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Glu Met Phe Thr Ile Arg Arg Arg Arg Arg Arg Arg Arg Arg
1               5                   10

<210> SEQ ID NO 91
<211> LENGTH: 25
<212> TYPE: PRT
<213> ORGANISM: Artificial Sequence
<220> FEATURE:
<223> OTHER INFORMATION: Description of Artificial Sequence: Synthetic
```

```
                       peptide

<400> SEQUENCE: 91

Met Phe Thr Ile Leu Leu Glu Glu Tyr Phe Met Tyr Arg Gly Leu Leu
1               5                   10                  15

Arg Arg Arg Arg Arg Arg Arg Arg Arg
            20                  25

<210> SEQ ID NO 92
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Phe Thr Ile Leu Leu Glu Glu Tyr Phe Met Tyr Arg Gly Leu Leu Arg
1               5                   10                  15

Arg Arg Arg Arg Arg Arg Arg Arg
            20

<210> SEQ ID NO 93
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Ile Leu Leu Glu Glu Tyr Phe Met Tyr Arg Gly Leu Leu Arg Arg
1               5                   10                  15

Arg Arg Arg Arg Arg Arg Arg
            20

<210> SEQ ID NO 94
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ile Leu Leu Glu Glu Tyr Phe Met Tyr Arg Gly Leu Leu Arg Arg Arg
1               5                   10                  15

Arg Arg Arg Arg Arg Arg
            20

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Leu Leu Glu Glu Tyr Phe Met Tyr Arg Gly Leu Leu Arg Arg Arg Arg
1               5                   10                  15

Arg Arg Arg Arg Arg
            20
```

```
<210> SEQ ID NO 96
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Glu Glu Tyr Phe Met Tyr Arg Gly Leu Leu Arg Arg Arg Arg Arg
1               5                   10                  15

Arg Arg Arg Arg
            20

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Glu Tyr Phe Met Tyr Arg Gly Leu Leu Arg Arg Arg Arg Arg Arg Arg
1               5                   10                  15

Arg Arg

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Tyr Phe Met Tyr Arg Gly Leu Leu Arg Arg Arg Arg Arg Arg Arg Arg
1               5                   10                  15

Arg

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Phe Met Tyr Arg Gly Leu Leu Arg Arg Arg Arg Arg Arg Arg Arg Arg
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Met Tyr Arg Gly Leu Leu Arg Arg Arg Arg Arg Arg Arg Arg Arg
1               5                   10                  15

<210> SEQ ID NO 101
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Tyr Arg Gly Leu Leu Arg Arg Arg Arg Arg Arg Arg Arg
1               5                   10

<210> SEQ ID NO 102
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Met Phe Thr Ile Leu Glu Glu Tyr Phe Met Tyr Arg Gly Leu Leu Gly
1               5                   10                  15

Leu Arg Ile Arg Arg Arg Arg Arg Arg Arg Arg Arg
            20                  25

<210> SEQ ID NO 103
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Phe Thr Ile Leu Leu Glu Glu Tyr Phe Met Tyr Arg Gly Leu Leu Gly
1               5                   10                  15

Leu Arg Ile Arg Arg Arg Arg Arg Arg Arg Arg Arg
            20                  25

<210> SEQ ID NO 104
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Thr Ile Leu Leu Glu Glu Tyr Phe Met Tyr Arg Gly Leu Leu Gly Leu
1               5                   10                  15

Arg Ile Arg Arg Arg Arg Arg Arg Arg Arg Arg
            20                  25

<210> SEQ ID NO 105
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ile Leu Leu Glu Glu Tyr Phe Met Tyr Arg Gly Leu Leu Gly Leu Arg
1               5                   10                  15

Ile Arg Arg Arg Arg Arg Arg Arg Arg Arg
            20                  25
```

<210> SEQ ID NO 106
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Leu Leu Glu Glu Tyr Phe Met Tyr Gly Leu Leu Gly Leu Arg Ile Arg
1               5                   10                  15

Arg Arg Arg Arg Arg Arg Arg Arg
            20

<210> SEQ ID NO 107
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Glu Tyr Phe Met Tyr Arg Gly Leu Leu Gly Leu Arg Ile Lys Tyr Gly
1               5                   10                  15

Arg Arg Arg Arg Arg Arg Arg Arg Arg
            20                  25

<210> SEQ ID NO 108
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Tyr Phe Met Tyr Arg Gly Leu Leu Gly Leu Arg Ile Lys Tyr Gly Arg
1               5                   10                  15

Arg Arg Arg Arg Arg Arg Arg Arg
            20

<210> SEQ ID NO 109
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Phe Met Tyr Arg Gly Leu Leu Gly Leu Arg Ile Lys Tyr Gly Arg Arg
1               5                   10                  15

Arg Arg Arg Arg Arg Arg Arg
            20

<210> SEQ ID NO 110
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Met Tyr Arg Gly Leu Leu Gly Leu Arg Ile Lys Tyr Gly Arg Arg
1               5                   10                  15

Arg Arg Arg Arg Arg Arg
            20

<210> SEQ ID NO 111
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Tyr Arg Gly Leu Leu Gly Leu Arg Ile Lys Tyr Gly Arg Arg Arg
1               5                   10                  15

Arg Arg Arg Arg Arg
            20

<210> SEQ ID NO 112
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Gly Leu Leu Gly Leu Arg Ile Lys Tyr Gly Arg Arg Arg Arg
1               5                   10                  15

Arg Arg Arg Arg
            20

<210> SEQ ID NO 113
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Leu Leu Gly Leu Arg Ile Lys Tyr Gly Arg Arg Arg Arg Arg
1               5                   10                  15

Arg Arg Arg

<210> SEQ ID NO 114
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Leu Leu Gly Leu Arg Ile Lys Tyr Gly Arg Arg Arg Arg Arg Arg
1               5                   10                  15

Arg Arg

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Leu Gly Leu Arg Ile Lys Tyr Gly Arg Arg Arg Arg Arg Arg Arg
1               5                   10                  15

Arg

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Leu Arg Ile Lys Tyr Gly Arg Arg Arg Arg Arg Arg Arg Arg
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Leu Arg Ile Lys Tyr Gly Arg Arg Arg Arg Arg Arg Arg Arg
1               5                   10                  15

<210> SEQ ID NO 118
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Ile Lys Tyr Gly Arg Arg Arg Arg Arg Arg Arg Arg
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Glu Glu Tyr Phe Met Arg Arg Arg Arg Arg Arg Arg Arg
1               5                   10

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Glu Glu Tyr Phe Met Tyr Arg Arg Arg Arg Arg Arg Arg Arg
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Glu Glu Tyr Phe Met Tyr Arg Arg Arg Arg Arg Arg Arg Arg Arg Arg
1               5                   10                  15

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Glu Glu Tyr Phe Met Tyr Arg Gly Arg Arg Arg Arg Arg Arg Arg Arg
1               5                   10                  15

Arg

<210> SEQ ID NO 123
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Glu Glu Tyr Phe Met Tyr Arg Gly Leu Arg Arg Arg Arg Arg Arg Arg
1               5                   10                  15

Arg Arg

<210> SEQ ID NO 124
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Glu Glu Tyr Phe Met Tyr Arg Gly Leu Leu Arg Arg Arg Arg Arg Arg
1               5                   10                  15

Arg Arg Arg

<210> SEQ ID NO 125
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Glu Glu Tyr Phe Met Tyr Arg Gly Leu Leu Gly Arg Arg Arg Arg Arg
1               5                   10                  15

Arg Arg Arg Arg
            20

<210> SEQ ID NO 126
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 126

Glu Glu Tyr Phe Met Tyr Arg Gly Leu Leu Gly Leu Arg Arg Arg
1               5                   10                  15

Arg Arg Arg Arg Arg
            20

<210> SEQ ID NO 127
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 127

Glu Glu Tyr Phe Met Tyr Arg Gly Leu Leu Gly Leu Arg Arg Arg
1               5                   10                  15

Arg Arg Arg Arg Arg Arg
            20

<210> SEQ ID NO 128
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Glu Glu Tyr Phe Met Tyr Arg Gly Leu Leu Gly Leu Arg Ile Arg Arg
1               5                   10                  15

Arg Arg Arg Arg Arg Arg Arg
            20

<210> SEQ ID NO 129
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Glu Glu Tyr Phe Met Tyr Arg Gly Leu Leu Gly Leu Arg Ile Lys Arg
1               5                   10                  15

Arg Arg Arg Arg Arg Arg Arg Arg
            20

<210> SEQ ID NO 130
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

```
Glu Glu Tyr Phe Met Tyr Arg Gly Leu Leu Gly Leu Arg Ile Lys Tyr
1               5                   10                  15

Arg Arg Arg Arg Arg Arg Arg Arg Arg
            20                  25
```

<210> SEQ ID NO 131
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

```
Ile Val Lys Leu Thr Val Tyr Asp Cys Ile Arg Arg Arg Arg Arg
1               5                   10                  15

Arg Arg Arg
```

<210> SEQ ID NO 132
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

```
Asp Ile Val Lys Leu Thr Val Tyr Asp Cys Arg Arg Arg Arg Arg
1               5                   10                  15

Arg Arg Arg
```

<210> SEQ ID NO 133
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

```
Ala Ile Val Lys Leu Thr Val Tyr Asp Cys Ile Arg Arg Arg Arg
1               5                   10                  15

Arg Arg Arg Arg
            20
```

<210> SEQ ID NO 134
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

```
Asp Ala Val Lys Leu Thr Val Tyr Asp Cys Ile Arg Arg Arg Arg
1               5                   10                  15

Arg Arg Arg Arg
            20
```

<210> SEQ ID NO 135
<211> LENGTH: 20
<212> TYPE: PRT
<213> ORGANISM: Artificial Sequence
<220> FEATURE:
<223> OTHER INFORMATION: Description of Artificial Sequence: Synthetic

```
                   peptide

<400> SEQUENCE: 135

Asp Ile Ala Lys Leu Thr Val Tyr Asp Cys Ile Arg Arg Arg Arg
1               5                   10                  15

Arg Arg Arg Arg
            20

<210> SEQ ID NO 136
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asp Ile Val Ala Leu Thr Val Tyr Asp Cys Ile Arg Arg Arg Arg
1               5                   10                  15

Arg Arg Arg Arg
            20

<210> SEQ ID NO 137
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asp Ile Val Lys Ala Thr Val Tyr Asp Cys Ile Arg Arg Arg Arg
1               5                   10                  15

Arg Arg Arg Arg
            20

<210> SEQ ID NO 138
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asp Ile Val Lys Leu Ala Val Tyr Asp Cys Ile Arg Arg Arg Arg
1               5                   10                  15

Arg Arg Arg Arg
            20

<210> SEQ ID NO 139
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Ile Val Lys Leu Thr Ala Tyr Asp Cys Ile Arg Arg Arg Arg
1               5                   10                  15

Arg Arg Arg Arg
            20
```

```
<210> SEQ ID NO 140
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Asp Ile Val Lys Leu Thr Val Ala Asp Cys Ile Arg Arg Arg Arg Arg
1               5                   10                  15

Arg Arg Arg Arg
            20

<210> SEQ ID NO 141
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Asp Ile Val Lys Leu Thr Val Tyr Ala Cys Ile Arg Arg Arg Arg Arg
1               5                   10                  15

Arg Arg Arg Arg
            20

<210> SEQ ID NO 142
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp Ile Val Lys Leu Thr Val Tyr Asp Ala Ile Arg Arg Arg Arg Arg
1               5                   10                  15

Arg Arg Arg Arg
            20

<210> SEQ ID NO 143
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asp Ile Val Lys Leu Thr Val Tyr Asp Cys Ala Arg Arg Arg Arg Arg
1               5                   10                  15

Arg Arg Arg Arg
            20

<210> SEQ ID NO 144
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Glu Ile Val Lys Leu Thr Val Tyr Asp Cys Ile Arg Arg Arg Arg Arg
```

```
1               5                   10                  15
Arg Arg Arg Arg
        20

<210> SEQ ID NO 145
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Asp Ile Val Lys Leu Thr Val Tyr Glu Cys Ile Arg Arg Arg Arg
1               5                   10                  15
Arg Arg Arg Arg
        20

<210> SEQ ID NO 146
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asp Ile Val Arg Leu Thr Val Tyr Asp Cys Ile Arg Arg Arg Arg
1               5                   10                  15
Arg Arg Arg Arg
        20

<210> SEQ ID NO 147
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asp Ile Val His Leu Thr Val Tyr Asp Cys Ile Arg Arg Arg Arg
1               5                   10                  15
Arg Arg Arg Arg
        20

<210> SEQ ID NO 148
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Lys Ile Val Lys Leu Thr Val Tyr Lys Cys Ile Arg Arg Arg Arg
1               5                   10                  15
Arg Arg Arg Arg
        20

<210> SEQ ID NO 149
<211> LENGTH: 20
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 149

Asp Ile Val Glu Leu Thr Val Tyr Asp Cys Ile Arg Arg Arg Arg
1               5                   10                  15

Arg Arg Arg Arg
            20

<210> SEQ ID NO 150
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asp Ile Val Lys Leu Ser Val Tyr Asp Cys Ile Arg Arg Arg Arg
1               5                   10                  15

Arg Arg Arg Arg
            20

<210> SEQ ID NO 151
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asp Ile Val Lys Leu Tyr Val Tyr Asp Cys Ile Arg Arg Arg Arg
1               5                   10                  15

Arg Arg Arg Arg
            20

<210> SEQ ID NO 152
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asp Ile Val Lys Leu Thr Val Ser Asp Cys Ile Arg Arg Arg Arg
1               5                   10                  15

Arg Arg Arg Arg
            20

<210> SEQ ID NO 153
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asp Ile Val Lys Leu Thr Val Thr Asp Cys Ile Arg Arg Arg Arg
1               5                   10                  15

Arg Arg Arg Arg
            20

<210> SEQ ID NO 154
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Asp Ile Val Lys Leu Thr Val Trp Asp Cys Ile Arg Arg Arg Arg Arg
1               5                   10                  15

Arg Arg Arg Arg
            20

<210> SEQ ID NO 155
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp Ile Val Lys Leu Thr Val Phe Asp Cys Ile Arg Arg Arg Arg Arg
1               5                   10                  15

Arg Arg Arg Arg
            20

<210> SEQ ID NO 156
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asp Ile Val Lys Leu Thr Val Tyr Asp Met Ile Arg Arg Arg Arg Arg
1               5                   10                  15

Arg Arg Arg Arg
            20

<210> SEQ ID NO 157
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asp Ile Val Lys Leu Thr Val Tyr Asp Ser Ile Arg Arg Arg Arg Arg
1               5                   10                  15

Arg Arg Arg Arg
            20

<210> SEQ ID NO 158
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)

<223> OTHER INFORMATION: L-Cysteine(S-carboxymethyl)

<400> SEQUENCE: 158

Asp Ile Val Lys Leu Thr Val Tyr Asp Cys Ile Arg Arg Arg Arg
1               5                   10                  15

Arg Arg Arg Arg
            20

<210> SEQ ID NO 159
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: L-Cysteine(S-carbamidomethyl)

<400> SEQUENCE: 159

Asp Ile Val Lys Leu Thr Val Tyr Asp Cys Ile Arg Arg Arg Arg
1               5                   10                  15

Arg Arg Arg Arg
            20

<210> SEQ ID NO 160
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: L-Cysteine(S-Acm)

<400> SEQUENCE: 160

Asp Ile Val Lys Leu Thr Val Tyr Asp Cys Ile Arg Arg Arg Arg
1               5                   10                  15

Arg Arg Arg Arg
            20

<210> SEQ ID NO 161
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Alpha-Aminobutyric acid

<400> SEQUENCE: 161

Asp Ile Val Lys Leu Thr Val Tyr Asp Xaa Ile Arg Arg Arg Arg
1               5                   10                  15

Arg Arg Arg Arg
            20

<210> SEQ ID NO 162
<211> LENGTH: 20
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: L-Norvaline

<400> SEQUENCE: 162

Asp Ile Val Lys Leu Thr Val Tyr Asp Val Ile Arg Arg Arg Arg
1               5                   10                  15

Arg Arg Arg Arg
            20

<210> SEQ ID NO 163
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Asp Leu Val Lys Leu Thr Val Tyr Asp Cys Ile Arg Arg Arg Arg
1               5                   10                  15

Arg Arg Arg Arg
            20

<210> SEQ ID NO 164
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Asp Val Val Lys Leu Thr Val Tyr Asp Cys Ile Arg Arg Arg Arg
1               5                   10                  15

Arg Arg Arg Arg
            20

<210> SEQ ID NO 165
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Asp Ile Leu Lys Leu Thr Val Tyr Asp Cys Ile Arg Arg Arg Arg
1               5                   10                  15

Arg Arg Arg Arg
            20

<210> SEQ ID NO 166
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Asp Ile Ile Lys Leu Thr Val Tyr Asp Cys Ile Arg Arg Arg Arg
1               5                   10                  15
```

Arg Arg Arg Arg
            20

<210> SEQ ID NO 167
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Asp Ile Val Lys Val Thr Val Tyr Asp Cys Ile Arg Arg Arg Arg
1               5                   10                  15

Arg Arg Arg Arg
            20

<210> SEQ ID NO 168
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Asp Ile Val Lys Ile Thr Val Tyr Asp Cys Ile Arg Arg Arg Arg
1               5                   10                  15

Arg Arg Arg Arg
            20

<210> SEQ ID NO 169
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Asp Ile Val Lys Leu Thr Leu Tyr Asp Cys Ile Arg Arg Arg Arg
1               5                   10                  15

Arg Arg Arg Arg
            20

<210> SEQ ID NO 170
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Asp Ile Val Lys Leu Thr Ile Tyr Asp Cys Ile Arg Arg Arg Arg
1               5                   10                  15

Arg Arg Arg Arg
            20

<210> SEQ ID NO 171
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Asp Ile Val Lys Leu Thr Val Tyr Asp Cys Leu Arg Arg Arg Arg
1               5                   10                  15

Arg Arg Arg Arg
            20

<210> SEQ ID NO 172
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Asp Ile Val Lys Leu Thr Val Tyr Asp Cys Val Arg Arg Arg Arg
1               5                   10                  15

Arg Arg Arg Arg
            20

<210> SEQ ID NO 173
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Asp Ile Asp Lys Leu Thr Glu Tyr Asp Ser Ile Arg Arg Arg Arg
1               5                   10                  15

Arg Arg Arg Arg
            20

<210> SEQ ID NO 174
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Asp Ile Pro Lys Leu Gly Val Pro Asp Cys Ile Arg Arg Arg Arg
1               5                   10                  15

Arg Arg Arg Arg
            20

<210> SEQ ID NO 175
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ile Cys Asp Tyr Val Thr Leu Lys Val Ile Asp Arg Arg Arg Arg
1               5                   10                  15

Arg Arg Arg Arg
            20

```
<210> SEQ ID NO 176
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Val Asp Leu Val Ile Asp Cys Ile Tyr Lys Thr Arg Arg Arg Arg
1               5                   10                  15

Arg Arg Arg Arg
            20

<210> SEQ ID NO 177
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Asp Ile Val Lys Leu Thr Val Tyr Asp Cys Ile Asp Ile Val Lys Leu
1               5                   10                  15

Thr Val Tyr Asp Cys Ile Arg Arg Arg Arg Arg Arg Arg Arg Arg
            20                  25                  30

<210> SEQ ID NO 178
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ile Val Lys Leu Thr Val Tyr Asp Cys Ile Arg Arg Arg Arg Arg Arg
1               5                   10                  15

Arg Arg Arg

<210> SEQ ID NO 179
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asp Ile Val Lys Leu Thr Val Tyr Asp Cys Ile Gly Arg Arg Arg Arg
1               5                   10                  15

Arg Arg Arg Arg Arg
            20

<210> SEQ ID NO 180
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Asp Ile Val Lys Leu Thr Val Tyr Asp Cys Ile Arg Arg Arg Arg Arg
1               5                   10                  15
```

Arg Arg Arg Arg
            20

<210> SEQ ID NO 181
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Ile Val Lys Leu Thr Val Tyr Ala Cys Ile Arg Arg Arg Arg Arg
1               5                   10                  15

Arg Arg Arg Arg
            20

<210> SEQ ID NO 182
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ala Ile Ile Lys Val Tyr Val Tyr Ala Cys Ile Arg Arg Arg Arg Arg
1               5                   10                  15

Arg Arg Arg Arg
            20

<210> SEQ ID NO 183
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Asp
<220> FEATURE:
<221> NAME/KEY: MOD_RES
<222> LOCATION: (2)..(2)
<223> OTHER INFORMATION: D-Ile
<220> FEATURE:
<221> NAME/KEY: MOD_RES
<222> LOCATION: (3)..(3)
<223> OTHER INFORMATION: D-Val
<220> FEATURE:
<221> NAME/KEY: MOD_RES
<222> LOCATION: (4)..(4)
<223> OTHER INFORMATION: D-Lys
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (6)..(6)
<223> OTHER INFORMATION: D-Thr
<220> FEATURE:
<221> NAME/KEY: MOD_RES
<222> LOCATION: (7)..(7)
<223> OTHER INFORMATION: D-Val
<220> FEATURE:
<221> NAME/KEY: MOD_RES
<222> LOCATION: (8)..(8)
<223> OTHER INFORMATION: D-Tyr
<220> FEATURE:

```
<221> NAME/KEY: MOD_RES
<222> LOCATION: (9)..(9)
<223> OTHER INFORMATION: D-Asp
<220> FEATURE:
<221> NAME/KEY: MOD_RES
<222> LOCATION: (10)..(10)
<223> OTHER INFORMATION: D-Cys
<220> FEATURE:
<221> NAME/KEY: MOD_RES
<222> LOCATION: (11)..(11)
<223> OTHER INFORMATION: D-Ile

<400> SEQUENCE: 183

Asp Ile Val Lys Leu Thr Val Tyr Asp Cys Ile Arg Arg Arg Arg
1               5                   10                  15

Arg Arg Arg Arg
            20

<210> SEQ ID NO 184
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Asp
<220> FEATURE:
<221> NAME/KEY: MOD_RES
<222> LOCATION: (2)..(2)
<223> OTHER INFORMATION: D-Ile
<220> FEATURE:
<221> NAME/KEY: MOD_RES
<222> LOCATION: (3)..(3)
<223> OTHER INFORMATION: D-Val
<220> FEATURE:
<221> NAME/KEY: MOD_RES
<222> LOCATION: (4)..(4)
<223> OTHER INFORMATION: D-Lys
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (6)..(6)
<223> OTHER INFORMATION: D-Thr
<220> FEATURE:
<221> NAME/KEY: MOD_RES
<222> LOCATION: (7)..(7)
<223> OTHER INFORMATION: D-Val
<220> FEATURE:
<221> NAME/KEY: MOD_RES
<222> LOCATION: (8)..(8)
<223> OTHER INFORMATION: D-Tyr
<220> FEATURE:
<221> NAME/KEY: MOD_RES
<222> LOCATION: (9)..(9)
<223> OTHER INFORMATION: D-Asp
<220> FEATURE:
<221> NAME/KEY: MOD_RES
<222> LOCATION: (10)..(10)
<223> OTHER INFORMATION: D-Cys
<220> FEATURE:
<221> NAME/KEY: MOD_RES
<222> LOCATION: (11)..(11)
<223> OTHER INFORMATION: D-Ile
<220> FEATURE:
<221> NAME/KEY: MOD_RES
<222> LOCATION: (12)..(20)
<223> OTHER INFORMATION: D-Arg

<400> SEQUENCE: 184
```

-continued

```
Asp Ile Val Lys Leu Thr Val Tyr Asp Cys Ile Arg Arg Arg Arg
1               5                   10                  15

Arg Arg Arg Arg
            20

<210> SEQ ID NO 185
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Asp
<220> FEATURE:
<221> NAME/KEY: MOD_RES
<222> LOCATION: (2)..(2)
<223> OTHER INFORMATION: D-Ile
<220> FEATURE:
<221> NAME/KEY: MOD_RES
<222> LOCATION: (3)..(3)
<223> OTHER INFORMATION: D-Val
<220> FEATURE:
<221> NAME/KEY: MOD_RES
<222> LOCATION: (4)..(4)
<223> OTHER INFORMATION: D-Lys
<220> FEATURE:
<221> NAME/KEY: MOD_RES
<222> LOCATION: (5)..(5)
<223> OTHER INFORMATION: D-Leu
<220> FEATURE:
<221> NAME/KEY: MOD_RES
<222> LOCATION: (6)..(6)
<223> OTHER INFORMATION: D-Thr
<220> FEATURE:
<221> NAME/KEY: MOD_RES
<222> LOCATION: (7)..(7)
<223> OTHER INFORMATION: D-Val
<220> FEATURE:
<221> NAME/KEY: MOD_RES
<222> LOCATION: (8)..(8)
<223> OTHER INFORMATION: D-Tyr
<220> FEATURE:
<221> NAME/KEY: MOD_RES
<222> LOCATION: (9)..(9)
<223> OTHER INFORMATION: D-Asp
<220> FEATURE:
<221> NAME/KEY: MOD_RES
<222> LOCATION: (10)..(10)
<223> OTHER INFORMATION: D-Cys
<220> FEATURE:
<221> NAME/KEY: MOD_RES
<222> LOCATION: (11)..(11)
<223> OTHER INFORMATION: D-Ile

<400> SEQUENCE: 185

Asp Ile Val Lys Leu Thr Val Tyr Asp Cys Ile
1               5                   10

<210> SEQ ID NO 186
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(20)
<223> OTHER INFORMATION: D-Arg

<400> SEQUENCE: 186
```

```
Asp Ile Val Lys Leu Thr Val Tyr Asp Cys Ile Arg Arg Arg Arg
1               5                   10                  15

Arg Arg Arg Arg
            20
```

<210> SEQ ID NO 187
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

```
Tyr Ile Lys Val Gln Lys Gln Asp Ile Val Lys Leu Thr Val Tyr Asp
1               5                   10                  15

Cys Ile Ser Met Ile Gly Leu Cys Ala
            20                  25
```

<210> SEQ ID NO 188
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

```
Ile Lys Val Gln Lys Gln Asp Ile Val Lys Leu Thr Val Tyr Asp Cys
1               5                   10                  15

Ile Ser Met Ile Gly Leu Cys Ala
            20
```

<210> SEQ ID NO 189
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

```
Lys Val Gln Lys Gln Asp Ile Val Lys Leu Thr Val Tyr Asp Cys Ile
1               5                   10                  15

Ser Met Ile Gly Leu Cys Ala
            20
```

<210> SEQ ID NO 190
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

```
Val Gln Lys Gln Asp Ile Val Lys Leu Thr Val Tyr Asp Cys Ile Ser
1               5                   10                  15

Met Ile Gly Leu Cys Ala
            20
```

<210> SEQ ID NO 191
<211> LENGTH: 21
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 191

Gln Lys Gln Asp Ile Val Lys Leu Thr Val Tyr Asp Cys Ile Ser Met
1               5                   10                  15

Ile Gly Leu Cys Ala
            20

<210> SEQ ID NO 192
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Lys Gln Asp Ile Val Lys Leu Thr Val Tyr Asp Cys Ile Ser Met Ile
1               5                   10                  15

Gly Leu Cys Ala
            20

<210> SEQ ID NO 193
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gln Asp Ile Val Lys Leu Thr Val Tyr Asp Cys Ile Ser Met Ile Gly
1               5                   10                  15

Leu Cys Ala

<210> SEQ ID NO 194
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Asp Ile Val Lys Leu Thr Val Tyr Asp Cys Ile Ser Met Ile Gly Leu
1               5                   10                  15

Cys Ala

<210> SEQ ID NO 195
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ile Val Lys Leu Thr Val Tyr Asp Cys Ile Ser Met Ile Gly Leu Cys
1               5                   10                  15

Ala

<210> SEQ ID NO 196
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Val Lys Leu Thr Val Tyr Asp Cys Ile Ser Met Ile Gly Leu Cys Ala
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Lys Leu Thr Val Tyr Asp Cys Ile Ser Met Ile Gly Leu Cys Ala
1               5                   10                  15

<210> SEQ ID NO 198
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Leu Thr Val Tyr Asp Cys Ile Ser Met Ile Gly Leu Cys Ala
1               5                   10

<210> SEQ ID NO 199
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Thr Val Tyr Asp Cys Ile Ser Met Ile Gly Leu Cys Ala
1               5                   10

<210> SEQ ID NO 200
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Val Tyr Asp Cys Ile Ser Met Ile Gly Leu Cys Ala
1               5                   10

<210> SEQ ID NO 201
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201
```

Tyr Asp Cys Ile Ser Met Ile Gly Leu Cys Ala
1               5                   10

<210> SEQ ID NO 202
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Asp Cys Ile Ser Met Ile Gly Leu Cys Ala
1               5                   10

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Cys Ile Ser Met Ile Gly Leu Cys Ala
1               5

<210> SEQ ID NO 204
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ile Ser Met Ile Gly Leu Cys Ala
1               5

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ser Met Ile Gly Leu Cys Ala
1               5

<210> SEQ ID NO 206
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Met Ile Gly Leu Cys Ala
1               5

<210> SEQ ID NO 207
<211> LENGTH: 5
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 207

Ile Gly Leu Cys Ala
1               5

<210> SEQ ID NO 208
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Tyr Ile Lys Val Gln Lys Gln Asp Ile Val Lys Leu Thr Val Tyr Asp
1               5                   10                  15

Cys Ile Ser Met Ile Gly Leu Cys
            20

<210> SEQ ID NO 209
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Tyr Ile Lys Val Gln Lys Gln Asp Ile Val Lys Leu Thr Val Tyr Asp
1               5                   10                  15

Cys Ile Ser Met Ile Gly Leu
            20

<210> SEQ ID NO 210
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Tyr Ile Lys Val Gln Lys Gln Asp Ile Val Lys Leu Thr Val Tyr Asp
1               5                   10                  15

Cys Ile Ser Met Ile Gly
            20

<210> SEQ ID NO 211
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Tyr Ile Lys Val Gln Lys Gln Asp Ile Val Lys Leu Thr Val Tyr Asp
1               5                   10                  15

Cys Ile Ser Met Ile
            20

<210> SEQ ID NO 212
<211> LENGTH: 20

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Tyr Ile Lys Val Gln Lys Gln Asp Ile Val Lys Leu Thr Val Tyr Asp
1               5                   10                  15

Cys Ile Ser Met
            20

<210> SEQ ID NO 213
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Tyr Ile Lys Val Gln Lys Gln Asp Ile Val Lys Leu Thr Val Tyr Asp
1               5                   10                  15

Cys Ile Ser

<210> SEQ ID NO 214
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Tyr Ile Lys Val Gln Lys Gln Asp Ile Val Lys Leu Thr Val Tyr Asp
1               5                   10                  15

Cys Ile

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Tyr Ile Lys Val Gln Lys Gln Asp Ile Val Lys Leu Thr Val Tyr Asp
1               5                   10                  15

Cys

<210> SEQ ID NO 216
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Tyr Ile Lys Val Gln Lys Gln Asp Ile Val Lys Leu Thr Val Tyr Asp
1               5                   10                  15

<210> SEQ ID NO 217
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Tyr Ile Lys Val Gln Lys Gln Asp Ile Val Lys Leu Thr Val Tyr
1               5                   10                  15

<210> SEQ ID NO 218
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Tyr Ile Lys Val Gln Lys Gln Asp Ile Val Lys Leu Thr Val
1               5                   10

<210> SEQ ID NO 219
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Tyr Ile Lys Val Gln Lys Gln Asp Ile Val Lys Leu Thr
1               5                   10

<210> SEQ ID NO 220
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Tyr Ile Lys Val Gln Lys Gln Asp Ile Val Lys Leu
1               5                   10

<210> SEQ ID NO 221
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Tyr Ile Lys Val Gln Lys Gln Asp Ile Val Lys
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Tyr Ile Lys Val Gln Lys Gln Asp Ile Val
```

```
1               5              10
```

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Tyr Ile Lys Val Gln Lys Gln Asp Ile
1               5

<210> SEQ ID NO 224
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Tyr Ile Lys Val Gln Lys Gln Asp
1               5

<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Tyr Ile Lys Val Gln Lys Gln
1               5

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Tyr Ile Lys Val Gln Lys
1               5

<210> SEQ ID NO 227
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Tyr Ile Lys Val Gln
1               5

<210> SEQ ID NO 228
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 228

Glu Met Phe Thr Ile Leu Glu Glu Tyr Phe Met Tyr Arg Gly Leu Leu
1               5                   10                  15

Gly Leu Arg Ile Lys Tyr Gly Arg Leu Phe Asn Glu Ile
            20                  25

<210> SEQ ID NO 229
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Met Phe Thr Ile Leu Glu Glu Tyr Phe Met Tyr Arg Gly Leu Leu Gly
1               5                   10                  15

Leu Arg Ile Lys Tyr Gly Arg Leu Phe Asn Glu Ile
            20                  25

<210> SEQ ID NO 230
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Phe Thr Ile Leu Glu Glu Tyr Phe Met Tyr Arg Gly Leu Leu Gly Leu
1               5                   10                  15

Arg Ile Lys Tyr Gly Arg Leu Phe Asn Glu Ile
            20                  25

<210> SEQ ID NO 231
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Thr Ile Leu Glu Glu Tyr Phe Met Tyr Arg Gly Leu Leu Gly Leu Arg
1               5                   10                  15

Ile Lys Tyr Gly Arg Leu Phe Asn Glu Ile
            20                  25

<210> SEQ ID NO 232
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ile Leu Glu Glu Tyr Phe Met Tyr Arg Gly Leu Leu Gly Leu Arg Ile
1               5                   10                  15

Lys Tyr Gly Arg Leu Phe Asn Glu Ile
            20                  25

```
<210> SEQ ID NO 233
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Leu Glu Glu Tyr Phe Met Tyr Arg Gly Leu Leu Gly Leu Arg Ile Lys
1               5                   10                  15

Tyr Gly Arg Leu Phe Asn Glu Ile
            20

<210> SEQ ID NO 234
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Glu Glu Tyr Phe Met Tyr Arg Gly Leu Leu Gly Leu Arg Ile Lys Tyr
1               5                   10                  15

Gly Arg Leu Phe Asn Glu Ile
            20

<210> SEQ ID NO 235
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Glu Tyr Phe Met Tyr Arg Gly Leu Leu Gly Leu Arg Ile Lys Tyr Gly
1               5                   10                  15

Arg Leu Phe Asn Glu Ile
            20

<210> SEQ ID NO 236
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Tyr Phe Met Tyr Arg Gly Leu Leu Gly Leu Arg Ile Lys Tyr Gly Arg
1               5                   10                  15

Leu Phe Asn Glu Ile
            20

<210> SEQ ID NO 237
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Phe Met Tyr Arg Gly Leu Leu Gly Leu Arg Ile Lys Tyr Gly Arg Leu
```

```
1               5                  10                 15
Phe Asn Glu Ile
            20

<210> SEQ ID NO 238
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Met Tyr Arg Gly Leu Leu Gly Leu Arg Ile Lys Tyr Gly Arg Leu Phe
1               5                  10                 15

Asn Glu Ile

<210> SEQ ID NO 239
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Tyr Arg Gly Leu Leu Gly Leu Arg Ile Lys Tyr Gly Arg Leu Phe Asn
1               5                  10                 15

Glu Ile

<210> SEQ ID NO 240
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Arg Gly Leu Leu Gly Leu Arg Ile Lys Tyr Gly Arg Leu Phe Asn Glu
1               5                  10                 15

Ile

<210> SEQ ID NO 241
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Leu Leu Gly Leu Arg Ile Lys Tyr Gly Arg Leu Phe Asn Glu Ile
1               5                  10                 15

<210> SEQ ID NO 242
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Leu Leu Gly Leu Arg Ile Lys Tyr Gly Arg Leu Phe Asn Glu Ile
```

```
                  1               5               10              15
```

<210> SEQ ID NO 243
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

```
Leu Gly Leu Arg Ile Lys Tyr Gly Arg Leu Phe Asn Glu Ile
1               5                   10
```

<210> SEQ ID NO 244
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

```
Gly Leu Arg Ile Lys Tyr Gly Arg Leu Phe Asn Glu Ile
1               5                   10
```

<210> SEQ ID NO 245
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

```
Leu Arg Ile Lys Tyr Gly Arg Leu Phe Asn Glu Ile
1               5                   10
```

<210> SEQ ID NO 246
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

```
Arg Ile Lys Tyr Gly Arg Leu Phe Asn Glu Ile
1               5                   10
```

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

```
Ile Lys Tyr Gly Arg Leu Phe Asn Glu Ile
1               5                   10
```

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 248

Lys Tyr Gly Arg Leu Phe Asn Glu Ile
1               5

<210> SEQ ID NO 249
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Tyr Gly Arg Leu Phe Asn Glu Ile
1               5

<210> SEQ ID NO 250
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gly Arg Leu Phe Asn Glu Ile
1               5

<210> SEQ ID NO 251
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Arg Leu Phe Asn Glu Ile
1               5

<210> SEQ ID NO 252
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Leu Phe Asn Glu Ile
1               5

<210> SEQ ID NO 253
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Glu Met Phe Thr Ile Leu Glu Glu Tyr Phe Met Tyr Arg Gly Leu Leu
1               5                   10                  15

Gly Leu Arg Ile Lys Tyr Gly Arg Leu Phe Asn Glu
            20                  25

<210> SEQ ID NO 254
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Glu Met Phe Thr Ile Leu Glu Glu Tyr Phe Met Tyr Arg Gly Leu Leu
1               5                   10                  15

Gly Leu Arg Ile Lys Tyr Gly Arg Leu Phe Asn
            20                  25

<210> SEQ ID NO 255
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Glu Met Phe Thr Ile Leu Glu Glu Tyr Phe Met Tyr Arg Gly Leu Leu
1               5                   10                  15

Gly Leu Arg Ile Lys Tyr Gly Arg Leu Phe
            20                  25

<210> SEQ ID NO 256
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Glu Met Phe Thr Ile Leu Glu Glu Tyr Phe Met Tyr Arg Gly Leu Leu
1               5                   10                  15

Gly Leu Arg Ile Lys Tyr Gly Arg Leu
            20                  25

<210> SEQ ID NO 257
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Glu Met Phe Thr Ile Leu Glu Glu Tyr Phe Met Tyr Arg Gly Leu Leu
1               5                   10                  15

Gly Leu Arg Ile Lys Tyr Gly Arg
            20

<210> SEQ ID NO 258
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

```
Glu Met Phe Thr Ile Leu Glu Glu Tyr Phe Met Tyr Arg Gly Leu Leu
1               5                   10                  15

Gly Leu Arg Ile Lys Tyr Gly
            20

<210> SEQ ID NO 259
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Glu Met Phe Thr Ile Leu Glu Glu Tyr Phe Met Tyr Arg Gly Leu Leu
1               5                   10                  15

Gly Leu Arg Ile Lys Tyr
            20

<210> SEQ ID NO 260
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Glu Met Phe Thr Ile Leu Glu Glu Tyr Phe Met Tyr Arg Gly Leu Leu
1               5                   10                  15

Gly Leu Arg Ile Lys
            20

<210> SEQ ID NO 261
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Glu Met Phe Thr Ile Leu Glu Glu Tyr Phe Met Tyr Arg Gly Leu Leu
1               5                   10                  15

Gly Leu Arg Ile
            20

<210> SEQ ID NO 262
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Glu Met Phe Thr Ile Leu Glu Glu Tyr Phe Met Tyr Arg Gly Leu Leu
1               5                   10                  15

Gly Leu Arg

<210> SEQ ID NO 263
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 263

Glu Met Phe Thr Ile Leu Glu Glu Tyr Phe Met Tyr Arg Gly Leu Leu
1               5                   10                  15

Gly Leu

<210> SEQ ID NO 264
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Glu Met Phe Thr Ile Leu Glu Glu Tyr Phe Met Tyr Arg Gly Leu Leu
1               5                   10                  15

Gly

<210> SEQ ID NO 265
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Glu Met Phe Thr Ile Leu Glu Glu Tyr Phe Met Tyr Arg Gly Leu Leu
1               5                   10                  15

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Glu Met Phe Thr Ile Leu Glu Glu Tyr Phe Met Tyr Arg Gly Leu
1               5                   10                  15

<210> SEQ ID NO 267
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Glu Met Phe Thr Ile Leu Glu Glu Tyr Phe Met Tyr Arg Gly
1               5                   10

<210> SEQ ID NO 268
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268
```

```
Glu Met Phe Thr Ile Leu Glu Glu Tyr Phe Met Tyr Arg
1               5                   10

<210> SEQ ID NO 269
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Glu Met Phe Thr Ile Leu Glu Glu Tyr Phe Met Tyr
1               5                   10

<210> SEQ ID NO 270
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Glu Met Phe Thr Ile Leu Glu Glu Tyr Phe Met
1               5                   10

<210> SEQ ID NO 271
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Glu Met Phe Thr Ile Leu Glu Glu Tyr Phe
1               5                   10

<210> SEQ ID NO 272
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Glu Met Phe Thr Ile Leu Glu Glu Tyr
1               5

<210> SEQ ID NO 273
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Glu Met Phe Thr Ile Leu Glu Glu
1               5

<210> SEQ ID NO 274
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 274

Glu Met Phe Thr Ile Leu Glu
1               5

<210> SEQ ID NO 275
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Glu Met Phe Thr Ile Leu
1               5

<210> SEQ ID NO 276
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Glu Met Phe Thr Ile
1               5

<210> SEQ ID NO 277
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Met Phe Thr Ile Leu Leu Glu Glu Tyr Phe Met Tyr Arg Gly Leu Leu
1               5                   10                  15

<210> SEQ ID NO 278
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Phe Thr Ile Leu Leu Glu Glu Tyr Phe Met Tyr Arg Gly Leu Leu
1               5                   10                  15

<210> SEQ ID NO 279
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Thr Ile Leu Leu Glu Glu Tyr Phe Met Tyr Arg Gly Leu Leu
1               5                   10
```

<210> SEQ ID NO 280
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ile Leu Leu Glu Glu Tyr Phe Met Tyr Arg Gly Leu Leu
1               5                   10

<210> SEQ ID NO 281
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Leu Leu Glu Glu Tyr Phe Met Tyr Arg Gly Leu Leu
1               5                   10

<210> SEQ ID NO 282
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Leu Glu Glu Tyr Phe Met Tyr Arg Gly Leu Leu
1               5                   10

<210> SEQ ID NO 283
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Glu Tyr Phe Met Tyr Arg Gly Leu Leu
1               5

<210> SEQ ID NO 284
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Tyr Phe Met Tyr Arg Gly Leu Leu
1               5

<210> SEQ ID NO 285
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 285

Phe Met Tyr Arg Gly Leu Leu
1               5

<210> SEQ ID NO 286
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Met Tyr Arg Gly Leu Leu
1               5

<210> SEQ ID NO 287
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Tyr Arg Gly Leu Leu
1               5

<210> SEQ ID NO 288
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Met Phe Thr Ile Leu Glu Glu Tyr Phe Met Tyr Arg Gly Leu Leu Gly
1               5                   10                  15

Leu Arg Ile

<210> SEQ ID NO 289
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Phe Thr Ile Leu Glu Glu Tyr Phe Met Tyr Arg Gly Leu Leu Gly
1               5                   10                  15

Leu Arg Ile

<210> SEQ ID NO 290
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Thr Ile Leu Leu Glu Glu Tyr Phe Met Tyr Arg Gly Leu Leu Gly Leu
1               5                   10                  15
```

Arg Ile

<210> SEQ ID NO 291
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ile Leu Leu Glu Glu Tyr Phe Met Tyr Arg Gly Leu Leu Gly Leu Arg
1               5                   10                  15

Ile

<210> SEQ ID NO 292
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Leu Leu Glu Glu Tyr Phe Met Tyr Gly Leu Leu Gly Leu Arg Ile
1               5                   10                  15

<210> SEQ ID NO 293
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Glu Tyr Phe Met Tyr Arg Gly Leu Leu Gly Leu Arg Ile Lys Tyr Gly
1               5                   10                  15

<210> SEQ ID NO 294
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Tyr Phe Met Tyr Arg Gly Leu Leu Gly Leu Arg Ile Lys Tyr Gly
1               5                   10                  15

<210> SEQ ID NO 295
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Phe Met Tyr Arg Gly Leu Leu Gly Leu Arg Ile Lys Tyr Gly
1               5                   10

<210> SEQ ID NO 296
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 296

Met Tyr Arg Gly Leu Leu Gly Leu Arg Ile Lys Tyr Gly
1               5                   10

<210> SEQ ID NO 297
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Tyr Arg Gly Leu Leu Gly Leu Arg Ile Lys Tyr Gly
1               5                   10

<210> SEQ ID NO 298
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Arg Gly Leu Leu Gly Leu Arg Ile Lys Tyr Gly
1               5                   10

<210> SEQ ID NO 299
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gly Leu Leu Gly Leu Arg Ile Lys Tyr Gly
1               5                   10

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Leu Leu Gly Leu Arg Ile Lys Tyr Gly
1               5

<210> SEQ ID NO 301
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Leu Gly Leu Arg Ile Lys Tyr Gly
1               5
```

```
<210> SEQ ID NO 302
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Gly Leu Arg Ile Lys Tyr Gly
1               5

<210> SEQ ID NO 303
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Leu Arg Ile Lys Tyr Gly
1               5

<210> SEQ ID NO 304
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Arg Ile Lys Tyr Gly
1               5

<210> SEQ ID NO 305
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Glu Glu Tyr Phe Met
1               5

<210> SEQ ID NO 306
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Glu Glu Tyr Phe Met Tyr
1               5

<210> SEQ ID NO 307
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 307

Glu Glu Tyr Phe Met Tyr Arg
1               5

<210> SEQ ID NO 308
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Glu Glu Tyr Phe Met Tyr Arg Gly
1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Glu Glu Tyr Phe Met Tyr Arg Gly Leu
1               5

<210> SEQ ID NO 310
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Glu Glu Tyr Phe Met Tyr Arg Gly Leu Leu
1               5                   10

<210> SEQ ID NO 311
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Glu Glu Tyr Phe Met Tyr Arg Gly Leu Leu Gly
1               5                   10

<210> SEQ ID NO 312
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Glu Glu Tyr Phe Met Tyr Arg Gly Leu Leu Gly Leu
1               5                   10

<210> SEQ ID NO 313
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 313

Glu Glu Tyr Phe Met Tyr Arg Gly Leu Leu Gly Leu Arg
1               5                   10

<210> SEQ ID NO 314
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Glu Glu Tyr Phe Met Tyr Arg Gly Leu Leu Gly Leu Arg Ile
1               5                   10

<210> SEQ ID NO 315
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Glu Glu Tyr Phe Met Tyr Arg Gly Leu Leu Gly Leu Arg Ile Lys
1               5                   10                  15

<210> SEQ ID NO 316
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Glu Glu Tyr Phe Met Tyr Arg Gly Leu Leu Gly Leu Arg Ile Lys Tyr
1               5                   10                  15

<210> SEQ ID NO 317
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Ile Val Lys Leu Thr Val Tyr Asp Cys Ile
1               5                   10

<210> SEQ ID NO 318
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Asp Ile Val Lys Leu Thr Val Tyr Asp Cys
1               5                   10
```

<210> SEQ ID NO 319
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Ala Ile Val Lys Leu Thr Val Tyr Asp Cys Ile
1               5                   10

<210> SEQ ID NO 320
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Asp Ala Val Lys Leu Thr Val Tyr Asp Cys Ile
1               5                   10

<210> SEQ ID NO 321
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Asp Ile Ala Lys Leu Thr Val Tyr Asp Cys Ile
1               5                   10

<210> SEQ ID NO 322
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Asp Ile Val Ala Leu Thr Val Tyr Asp Cys Ile
1               5                   10

<210> SEQ ID NO 323
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Asp Ile Val Lys Ala Thr Val Tyr Asp Cys Ile
1               5                   10

<210> SEQ ID NO 324
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 324

Asp Ile Val Lys Leu Ala Val Tyr Asp Cys Ile
1               5                   10

<210> SEQ ID NO 325
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Asp Ile Val Lys Leu Thr Ala Tyr Asp Cys Ile
1               5                   10

<210> SEQ ID NO 326
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Asp Ile Val Lys Leu Thr Val Ala Asp Cys Ile
1               5                   10

<210> SEQ ID NO 327
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Asp Ile Val Lys Leu Thr Val Tyr Ala Cys Ile
1               5                   10

<210> SEQ ID NO 328
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Asp Ile Val Lys Leu Thr Val Tyr Asp Ala Ile
1               5                   10

<210> SEQ ID NO 329
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Asp Ile Val Lys Leu Thr Val Tyr Asp Cys Ala
1               5                   10

<210> SEQ ID NO 330
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Glu Ile Val Lys Leu Thr Val Tyr Asp Cys Ile
1               5                   10

<210> SEQ ID NO 331
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Asp Ile Val Lys Leu Thr Val Tyr Glu Cys Ile
1               5                   10

<210> SEQ ID NO 332
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Asp Ile Val Arg Leu Thr Val Tyr Asp Cys Ile
1               5                   10

<210> SEQ ID NO 333
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Asp Ile Val His Leu Thr Val Tyr Asp Cys Ile
1               5                   10

<210> SEQ ID NO 334
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Lys Ile Val Lys Leu Thr Val Tyr Lys Cys Ile
1               5                   10

<210> SEQ ID NO 335
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Asp Ile Val Glu Leu Thr Val Tyr Asp Cys Ile
```

```
<210> SEQ ID NO 336
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Asp Ile Val Lys Leu Ser Val Tyr Asp Cys Ile
1               5                   10

<210> SEQ ID NO 337
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Asp Ile Val Lys Leu Tyr Val Tyr Asp Cys Ile
1               5                   10

<210> SEQ ID NO 338
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Asp Ile Val Lys Leu Thr Val Ser Asp Cys Ile
1               5                   10

<210> SEQ ID NO 339
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Asp Ile Val Lys Leu Thr Val Thr Asp Cys Ile
1               5                   10

<210> SEQ ID NO 340
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Asp Ile Val Lys Leu Thr Val Trp Asp Cys Ile
1               5                   10

<210> SEQ ID NO 341
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 341

Asp Ile Val Lys Leu Thr Val Phe Asp Cys Ile
1               5                   10

<210> SEQ ID NO 342
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Asp Ile Val Lys Leu Thr Val Tyr Asp Met Ile
1               5                   10

<210> SEQ ID NO 343
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Asp Ile Val Lys Leu Thr Val Tyr Asp Ser Ile
1               5                   10

<210> SEQ ID NO 344
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: L-Cysteine(S-carboxymethyl)

<400> SEQUENCE: 344

Asp Ile Val Lys Leu Thr Val Tyr Asp Cys Ile
1               5                   10

<210> SEQ ID NO 345
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: L-Cysteine(S-carbamidomethyl)

<400> SEQUENCE: 345

Asp Ile Val Lys Leu Thr Val Tyr Asp Cys Ile
1               5                   10

<210> SEQ ID NO 346
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (10)..(10)
<223> OTHER INFORMATION: L-Cysteine(S-Acm)

<400> SEQUENCE: 346

Asp Ile Val Lys Leu Thr Val Tyr Asp Cys Ile
1               5                   10

<210> SEQ ID NO 347
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Alpha-Aminobutyric acid

<400> SEQUENCE: 347

Asp Ile Val Lys Leu Thr Val Tyr Asp Xaa Ile
1               5                   10

<210> SEQ ID NO 348
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: L-Norvaline

<400> SEQUENCE: 348

Asp Ile Val Lys Leu Thr Val Tyr Asp Val Ile
1               5                   10

<210> SEQ ID NO 349
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Asp Leu Val Lys Leu Thr Val Tyr Asp Cys Ile
1               5                   10

<210> SEQ ID NO 350
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Asp Val Val Lys Leu Thr Val Tyr Asp Cys Ile
1               5                   10

<210> SEQ ID NO 351
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 351

Asp Ile Leu Lys Leu Thr Val Tyr Asp Cys Ile
1               5                   10

<210> SEQ ID NO 352
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Asp Ile Ile Lys Leu Thr Val Tyr Asp Cys Ile
1               5                   10

<210> SEQ ID NO 353
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Asp Ile Val Lys Val Thr Val Tyr Asp Cys Ile
1               5                   10

<210> SEQ ID NO 354
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Asp Ile Val Lys Ile Thr Val Tyr Asp Cys Ile
1               5                   10

<210> SEQ ID NO 355
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Asp Ile Val Lys Leu Thr Leu Tyr Asp Cys Ile
1               5                   10

<210> SEQ ID NO 356
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Asp Ile Val Lys Leu Thr Ile Tyr Asp Cys Ile
1               5                   10
```

<210> SEQ ID NO 357
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Asp Ile Val Lys Leu Thr Val Tyr Asp Cys Leu
1               5                   10

<210> SEQ ID NO 358
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Asp Ile Val Lys Leu Thr Val Tyr Asp Cys Val
1               5                   10

<210> SEQ ID NO 359
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Asp Ile Asp Lys Leu Thr Glu Tyr Asp Ser Ile
1               5                   10

<210> SEQ ID NO 360
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Asp Ile Pro Lys Leu Gly Val Pro Asp Cys Ile
1               5                   10

<210> SEQ ID NO 361
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Ile Cys Asp Tyr Val Thr Leu Lys Val Ile Asp
1               5                   10

<210> SEQ ID NO 362
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 362

Val Asp Leu Val Ile Asp Cys Ile Tyr Lys Thr
1               5                   10

<210> SEQ ID NO 363
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Asp Ile Val Lys Leu Thr Val Tyr Asp Cys Ile Asp Ile Val Lys Leu
1               5                   10                  15

Thr Val Tyr Asp Cys Ile
            20

<210> SEQ ID NO 364
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ile Val Lys Leu Thr Val Tyr Asp Cys Ile
1               5                   10

<210> SEQ ID NO 365
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Asp Ile Val Lys Leu Thr Val Tyr Asp Cys Ile Gly
1               5                   10

<210> SEQ ID NO 366
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Asp Ile Val Lys Leu Thr Val Tyr Asp Cys Ile
1               5                   10

<210> SEQ ID NO 367
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Ala Ile Val Lys Leu Thr Val Tyr Ala Cys Ile
1               5                   10
```

```
<210> SEQ ID NO 368
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Ala Ile Ile Lys Val Tyr Val Tyr Ala Cys Ile
1               5                   10

<210> SEQ ID NO 369
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Asp Ile Val Lys Leu Thr Val Tyr Asp Cys Ile
1               5                   10

<210> SEQ ID NO 370
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Leu Glu Glu Tyr Phe Met Tyr
1               5

<210> SEQ ID NO 371
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Phe Thr Ile Leu Glu Glu Tyr Phe Met Tyr
1               5                   10

<210> SEQ ID NO 372
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Val Tyr Asp Cys Ile
1               5

<210> SEQ ID NO 373
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373
```

Val Tyr Ala Cys Ile
1               5

<210> SEQ ID NO 374
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Lys Leu Thr Val Tyr
1               5

<210> SEQ ID NO 375
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Lys Leu Tyr Val Tyr
1               5

<210> SEQ ID NO 376
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Lys Val Tyr Val Tyr
1               5

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
tccatgacgt tcctgacgtt                                              20

<210> SEQ ID NO 378
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Asp Ile Val Lys Leu Thr Val Tyr Asp Cys Ile Arg Arg Arg Arg
1               5                   10                  15

Arg Arg Arg Arg
            20

<210> SEQ ID NO 379
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Arg Arg Arg Arg Arg Arg Arg Arg Arg
1               5
```